(12) United States Patent
Hayoz et al.

(10) Patent No.: US 8,067,643 B2
(45) Date of Patent: Nov. 29, 2011

(54) SULPHONIUM SALT INITIATORS

(75) Inventors: Pascal Hayoz, Hofstetten (CH); Stephan Ilg, Giebenach (CH)

(73) Assignee: BASF SE, Ludwigshafen (DE)

( * ) Notice: Subject to any disclaimer, the term of this patent is extended or adjusted under 35 U.S.C. 154(b) by 442 days.

(21) Appl. No.: 12/226,116

(22) PCT Filed: Apr. 4, 2007

(86) PCT No.: PCT/EP2007/053280
§ 371 (c)(1),
(2), (4) Date: Oct. 8, 2008

(87) PCT Pub. No.: WO2007/118794
PCT Pub. Date: Apr. 4, 2007

(65) Prior Publication Data
US 2009/0197987 A1    Aug. 6, 2009

(30) Foreign Application Priority Data

Apr. 13, 2006   (EP) .................................. 06112602

(51) Int. Cl.
*C07C 381/00* (2006.01)
*C08F 2/50* (2006.01)

(52) U.S. Cl. ............. 568/77; 568/18; 568/19; 568/74; 568/57; 549/1; 549/29; 549/62; 549/64; 522/31

(58) Field of Classification Search ............ 522/31; 568/18, 19, 57, 74, 77; 549/1, 29, 62, 64
See application file for complete search history.

(56) References Cited

U.S. PATENT DOCUMENTS

| | | | |
|---|---|---|---|
| 4,197,174 A * | 4/1980 | Chang ............................. | 522/55 |
| 4,201,640 A * | 5/1980 | Watt ............................... | 522/31 |
| 4,451,409 A | 5/1984 | Buske et al. ................... | 260/513 |
| 4,694,029 A | 9/1987 | Land .............................. | 522/8 |
| 5,446,172 A * | 8/1995 | Crivello et al. ................ | 549/62 |
| 6,368,769 B1 | 4/2002 | Ohkawa et al. ............. | 430/270.1 |
| 6,696,216 B2 * | 2/2004 | Li et al. ....................... | 430/270.1 |
| 7,060,858 B2 * | 6/2006 | Date et al. ...................... | 568/18 |
| 7,101,998 B2 | 9/2006 | Herlihy et al. .................. | 544/38 |
| 7,230,121 B2 | 6/2007 | Norcini et al. .................... | 549/3 |
| 7,405,308 B2 * | 7/2008 | Crivello .......................... | 549/17 |
| 7,592,376 B2 * | 9/2009 | Crivello .......................... | 522/15 |
| 7,611,817 B2 * | 11/2009 | Nakayashiki et al. ....... | 430/270.1 |
| 7,795,323 B2 * | 9/2010 | Takabayashi .................... | 522/31 |
| 2002/0193619 A1 * | 12/2002 | Crivello et al. ................... | 556/1 |
| 2005/0064333 A1 * | 3/2005 | Crivello ..................... | 430/270.1 |
| 2006/0055088 A1 | 3/2006 | Nakayashiki et al. ........ | 264/425 |
| 2007/0225395 A1 | 9/2007 | Wolf et al. ...................... | 522/36 |
| 2010/0297542 A1 * | 11/2010 | Hayoz et al. .................... | 430/7 |

FOREIGN PATENT DOCUMENTS

| | | |
|---|---|---|
| EP | 1 036 789 | 9/2000 |
| EP | 1 557 413 | 7/2005 |
| GB | 2 061 280 | 5/1981 |
| WO | 03/008404 | 1/2003 |
| WO | 03/072567 | 9/2003 |

* cited by examiner

*Primary Examiner* — Sanza McClendon
(74) *Attorney, Agent, or Firm* — Qi Zhuo

(57) ABSTRACT

Compounds of the formula (I), L, L', L", $L_1$, $L'_1$, $L"_1$, $L_2$, $L'_2$, $L"_2$, $L_3$, $L'_3$, $L"_3$, $L_4$, $L'_4$, $L"_4$, $L_5$, $L'_5$, $L"_5$, $L_6$, $L'_6$, $L"_6$, $L_7$, $L'_7$, $L"_7$, $L_8$, $L'_8$ and $L"_8$ independently of one another are hydrogen or an organic substituent; and/or one or more of the pairs $L_3$ and $L_5$, $L'_3$ and $L'_5$ or $L"_3$ and $L"_5$ together denote a single bond, provided that the respective X, X' or X" is not a single bond; and/or $L_3$ and $L_5$, $L'_3$ and $L'_5$ or $L"_3$ and $L"_5$ together denote an organic linking group; and/or one or more of the pairs $L_1$ and $L_3$, $L_1$ and L, $L_5$ and $L_7$, $L'_1$ and $L'_3$, $L'_1$ and $L'$, $L'_5$ and $L'_7$, $L"_1$ and $L"_3$, $L"_1$ and $L"$, or $L"_5$ and $L"_7$, together denote an organic linking group; provided that at least one of L, L', L", $L_1$, $L'_1$, $L"_1$, $L_2$, $L'_2$, $L"_2$, $L_3$, $L'_3$, $L"_3$, $L_4$, $L'_4$, $L"_4$, $L_5$, $L'_5$, $L"_5$, $L_6$, $L'_6$, $L"_6$, $L_7$, $L'_7$, $L"_7$, $L_8$, $L'_8$ and $L"_8$ is other than hydrogen; X, X' and X" independently of one another are a single bond, $CR_aR_b$, O, S, $NR_c$ or $NCOR_c$; $R_a$, $R_b$ and $R_c$ independently of one another are hydrogen or an organic substituent; and Y is an inorganic or organic anion; are suitable as photolatent acid generators.

(I)

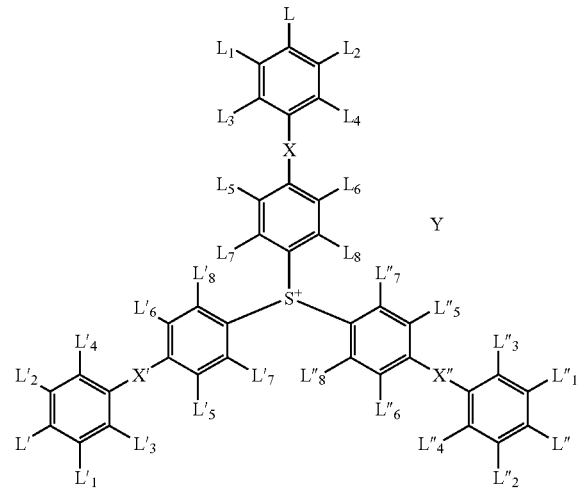

10 Claims, No Drawings

SULPHONIUM SALT INITIATORS

The invention pertains to novel sulphonium salt photoinitiators and their use in photocurable compositions.

Sulphonium salts are known in the art as photoinitiators. In GB 2061280 triarylsulphonium salts, comprising a phenylythio moiety, are disclosed. Other compounds of this type, inter alia with phenoxy groups, are known from U.S. Pat. No. 4,451,409 and U.S. Pat. No. 4,694,029, for example tris(4-phenoxyphenyl)sulphonium hexafluorophosphate. WO 03/072567 and WO 03/008404 disclose sulphonium salts, wherein the sulphonium ion is located in a condensed ring system, for example in the thioxanthyl moiety.

One major problem of commercially available sulphonium salt photoinitiators is the formation of toxic and/or odorous break down products like diphenyl sulfide or benzene. In technique there is a need for effective cationic photoinitiators, which are reactive, in particular in both clear and pigmented coatings, thin and thick layers, with and without the addition of sensitizers as co-initiators, non toxic and which generate non toxic and odorless break down products and which further are low-yellowing.

It now has been found, that compounds of the formula I,

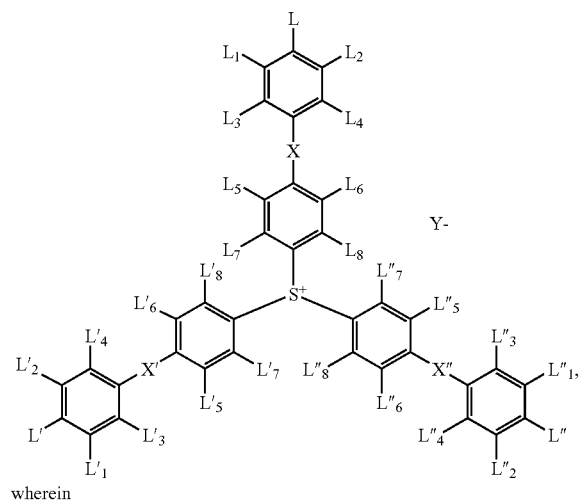

(I)

wherein

L, L', L", $L_1$, $L'_1$, $L''_1$, $L_2$, $L'_2$, $L''_2$, $L_3$, $L'_3$, $L''_3$, $L_4$, $L'_4$, $L''_4$, $L_5$, $L'_5$, $L''_5$, $L_6$, $L'_6$, $L''_6$, $L_7$, $L'_7$, $L''_7$, $L_8$, $L'_8$ and $L''_8$ independently of one another are hydrogen or an organic substituent; and/or one or more of the pairs $L_3$ and $L_5$, $L'_3$ and $L'_5$ or $L''_3$ and $L''_5$ together denote a single bond, provided that the respective X, X' or X" is not a single bond; and/or $L_3$ and $L_5$, $L'_3$ and $L'_5$ or $L''_3$ and $L''_5$ together denote an organic linking group; and/or one or more of the pairs $L_1$ and $L_3$, $L_1$ and L, $L_5$ and $L_7$, $L'_1$ and $L'_3$, $L'_1$ and L', $L'_5$ and $L'_7$, $L''_1$ and $L''_3$, $L''_1$ and L", or $L''_5$ and $L''_7$, together denote an organic linking group;

provided that at least one of L, L', L", $L_1$, $L'_1$, $L''_1$, $L_2$, $L'_2$, $L''_2$, $L_3$, $L'_3$, $L''_3$, $L_4$, $L'_4$, $L''_4$, $L_5$, $L'_5$, $L''_5$, $L_6$, $L'_6$, $L''_6$, $L_7$, $L'_7$, $L''_7$, $L_8$, $L'_8$ and $L''_8$ is other than hydrogen;

X, X' and X" independently of one another are a single bond, $CR_aR_b$, O, S, $NR_c$ or $NCOR_c$;

$R_a$, $R_b$ and $R_c$ independently of one another are hydrogen or an organic substituent; and Y is an inorganic or organic anion; are effective, low-yellowing photolatent sulphonium salts.

The compounds according to the invention are characterized in that at least one of the phenyl rings bears a substituent other than hydrogen.

Said compounds excel at a good reactivity in combination with low yellowing, low odor and good solubility in the photocurable formulation. The photolatent acid sulphonium salt compounds of formula I exhibit a very satisfactory reactivity combined with good solubility and low yellowing properties. A very important advantage in view of environmental aspects is the fact that the compounds according to the present invention do not release benzene.

Preferred are compounds of the formula I, wherein L, L' and L" are identical and $L_1$, $L'_1$ and $L''_1$ are identical and $L_2$, $L'_2$ and $L''_2$ are identical and $L_3$, $L'_3$ and $L''_3$ are identical and $L_4$, $L'_4$ and $L''_4$ are identical and $L_5$, $L'_5$ and $L''_5$ are identical and $L_6$, $L'_6$ and $L''_6$ are identical and $L_7$, $L'_7$ and $L''_7$ are identical and $L_8$, $L'_8$ and $L''_8$ are identical and X, X' and X" are identical, namely a compound of the formula Ia

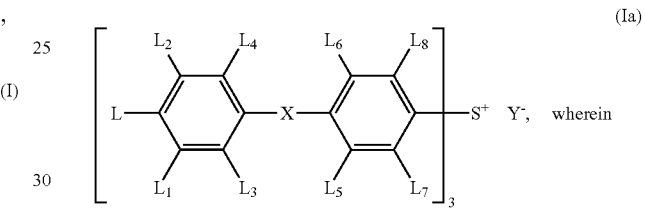

(Ia)

L, $L_1$, $L_2$, $L_3$, $L_4$, $L_5$, $L_6$, $L_7$ and $L_8$ independently of one another are hydrogen, $R_1$, $OR_1$, $SR_1$, $NR_1R_2$, halogen, $NO_2$, CN, $NR_1COR_2$, $COOR_1$, $OCOR_1$, $CONR_1R_2$, $OCOOR_1$, $OCONR_1R_2$, $NR_1COOR_2$, $SO_3H$, $SO_3M$, $SOR_1$, $SO_2R_1$ or are COT;

and/or one or more of the pairs $L_3$ and $L_5$ together are a single bond, $CR_aR_b$, CO, O, S, $NR_c$ or $NCOR_C$; provided that $L_3$ and $L_5$ together are no single bond, when the respective X denotes a single bond; and/or one or more of the pairs $L_1$ and $L_3$, $L_1$ and L, $L_5$ and $L_7$ together are $C_3$-$C_4$alkylene, $CR_1$=$CR_2$—$CR_3$=$CR_4$, $CR_1$=$CR_2$—O, $CR_1$=$CR_2$—S, $CR_1$=$CR_2$—$NR_1$, CO—O—CO, $CONR_1CO$, CO-(o-phenylene)-S, CO-(o-phenylene)-S substituted by one or more D, or are $C_1$-$C_3$alkylene interrupted by O, S, $NR_1$ or $NCOR_1$;

provided that at least one of L, $L_1$, $L_2$, $L_3$, $L_4$, $L_5$, $L_6$, $L_7$, $L_8$ is other than hydrogen;

$T_1$ and $T_2$ independently of one another are hydrogen, $C_1$-$C_{20}$alkyl, $C_5$-$C_{12}$cycloalkyl, $C_2$-$C_{20}$alkenyl, $C_5$-$C_{12}$cycloalkenyl, $C_6$-$C_{14}$aryl, $C_1$-$C_{20}$alkyl substituted by one or more D, $C_2$-$C_{20}$alkyl interrupted by one or more E, $C_2$-$C_{20}$alkyl substituted by one or more D and interrupted by one or more E, $C_5$-$C_{12}$cycloalkyl substituted by one or more D, $C_2$-$C_{12}$cycloalkyl interrupted by one or more E, $C_2$-$C_{12}$cycloalkyl substituted by one or more D and interrupted by one or more E, $C_2$-$C_{20}$alkenyl substituted by one or more D, $C_3$-$C_{20}$alkenyl interrupted by one or more E, $C_3$-$C_{20}$alkenyl substituted by one or more D and interrupted by one or more E, $C_5$-$C_{12}$cycloalkenyl substituted by one or more D, $C_3$-$C_{12}$cycloalkenyl interrupted by one or more E, $C_3$-$C_{12}$cycloalkenyl substituted by one or more D and interrupted by one or more E, or $C_6$-$C_{14}$aryl substituted by one or more D;

$R_1$, $R_2$, $R_3$, $R_4$, $R_a$, $R_b$ and $R_c$ independently of one another have the meaning of $T_1$;

T denotes $T_1$ or O-$T_2$;

X, X' and X" independently of one another are a single bond, $CR_aR_b$, O, S, $NR_c$ or $NCOR_c$;

D is hydrogen, $R_5$, $OR_5$, $SR_5$, $NR_5R_6$, halogen, $NO_2$, CN, O-glycidyl, O-vinyl, O-allyl, $COR_5$, $NR_5COR_6$, $COOR_5$, $OCOR_5$, $CONR_5R_6$, $OCOOR_5$, $OCONR_5R_6$, $NR_5COOR_6$, $SO_3H$ or $SO_3M$;

E is O, S, COO, OCO, CO, $NR_5$, $NCOR_5$, $NR_5CO$, $CONR_5$, OCOO, $OCONR_5$, $NR_5COO$, $SO_2$, SO, $CR_5=CR_6$ or

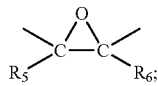

$R_5$ and $R_6$ independently of one another are hydrogen, $C_1$-$C_{12}$alkyl or phenyl;

Y is an inorganic or organic anion; and

M is an inorganic or organic cation.

$C_1$-$C_{20}$alkyl is linear or branched and is, for example, $C_1$-$C_{18}$-, $C_1$-$C_{14}$-, $C_1$-$C_{12}$-, $C_1$-$C_8$-, $C_1$-$C_6$- or $C_1$-$C_4$alkyl. Examples are methyl, ethyl, propyl, isopropyl, n-butyl, sec-butyl, isobutyl, tert-butyl, pentyl, hexyl, heptyl, 2,4,4-trimethylpentyl, 2-ethylhexyl, octyl, nonyl, decyl, dodecyl, tetradecyl, pentadecyl, hexadecyl, octadecyl and icosyl.

$C_1$-$C_{18}$alkyl, $C_1$-$C_{14}$alkyl, $C_1$-$C_{12}$alkyl, $C_1$-$C_8$alkyl, $C_1$-$C_6$alkyl and $C_1$-$C_4$alkyl have the same meanings as given above for $C_1$-$C_{20}$alkyl up to the corresponding number of C-atoms.

$C_2$-$C_{20}$alkyl interrupted by one or more E, with E defined as O, S, COO, OCO, CO, $NR_5$, $NCOR_5$, $NR_5CO$, $CONR_5$, OCOO, $OCONR_5$, $NR_5COO$, $SO_2$, SO, $CR_5=CR_6$,

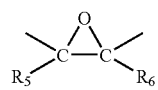

is for example interrupted 1-9, 1-7 or once or twice by E. In case the groups are interrupted by more than one E, said E preferably are seperated from one another by at least one carbon atom, i.e. the E preferably are non-consecutive, in particular if E denotes O. Examples are the following structural units —$CH_2$—O—$CH_3$, —$CH_2CH_2$—O—$CH_2CH_3$, —[$CH_2CH_2O$]$_y$—$CH_3$, with y=1-9, —($CH_2CH_2O$)$_7$$CH_2CH_3$, —$CH_2$—CH($CH_3$)—O—$CH_2$—$CH_2CH_3$, —$CH_2$—CH($CH_3$)—O—$CH_2CH_3$, —$CH_2$—S—$CH_3$, —$CH_2CH_2$—S—$CH_2CH_3$, —$CH_2$—(CO)O—$CH_3$, —$CH_2$—(CO)—$CH_3$, —$CH_2$—$NR_5$—$CH_3$, —$CH_2CH_2$—$NR_5$—$CH_2CH_3$, —$CH_2$—COO—$CH_2$—$CH_2$—O—$CH_3$ etc.

$C_2$-$C_{10}$alkenyl is mono or polyunsaturated, linear or branched and is for example $C_2$-$C_8$—, $C_2$-$C_6$— or $C_2$-$C_4$alkenyl. Examples are allyl, methallyl, vinyl, 1,1-dimethylallyl, 1-butenyl, 3-butenyl, 2-butenyl, 1,3-pentadienyl, 5-hexenyl or 7-octenyl, especially allyl or vinyl.

$C_5$-$C_{12}$cycloalkyl is for example cyclopentyl, cyclohexyl, cyclooctyl, cyclo-dodecyl, especially cyclopentyl and cyclohexyl, preferably cyclohexyl. $C_3$-$C_{12}$Cycloalkyl in the context of the present application is to be understood as alkyl which at least comprises one ring. For example methyl-cyclopentyl, cyclopentyl, cyclohexyl, methyl- or dimethylcyclohexyl, cyclooctyl, especially cyclopentyl and cyclohexyl, preferably cyclohexyl are also meant. Further examples are structures like

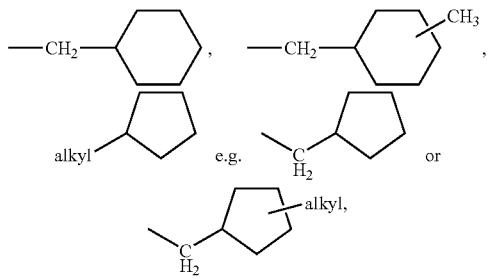

as well as bridged or fused ring systems, e.g.

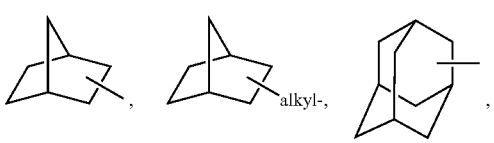

etc. are also meant to be covered by the term.

$C_2$-$C_{12}$cycloalkyl interrupted by one or more E with E defined as O, S, COO, OCO, CO, $NR_5$, $NCOR_5$, $NR_5CO$, $CONR_5$, OCOO, $OCONR_5$, $NR_5COO$, $SO_2$, SO, $CR_5=CR_6$,

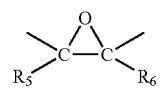

is for example

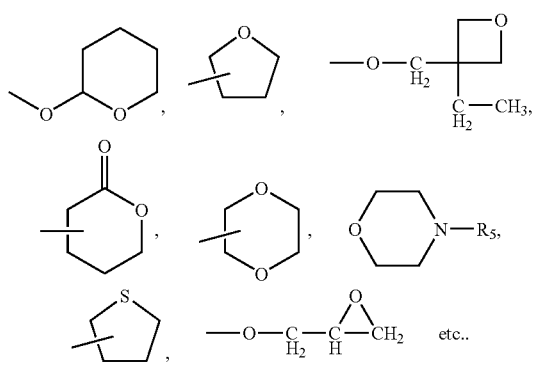

$C_5$-$C_{12}$cycloalkenyl, has one or more double bonds and is for example $C_4$-$C_6$-cycloalkenyl or $C_6$-$C_8$-cycloalkenyl. Examples are cyclopentenyl, cyclohexenyl or cyclooctenyl, especially cyclopentenyl and cyclohexenyl, preferably cyclohexenyl. $C_5$-$C_{12}$cycloalkenyl in the context of the present application is to be understood as alkenyl which at least comprises one ring. For example methyl-cyclopentenyl, dimethylcyclohexenyl etc. are also meant.

$C_6$-$C_{14}$aryl is for example phenyl, 1-naphthyl, 2-naphthyl, anthryl or phenanthryl, in particular phenyl.

Substituted $C_6$-$C_{14}$aryl is for example substituted one to four times, e.g. once, twice or three times, especially once or twice. Substituents on the phenyl ring are in position 2-, 3- or 4-, or in position 2,4-, 2,6-, 2,3-, 3,4-, 3,5-, 2,4,6—especially in position 2- or 4- of the phenyl ring. Substituted naphthyl, anthryl or phenanthryl is for example substituted one to four times, e.g. once, twice or three times, preferably once.

Glycidyl is

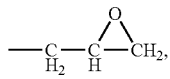

O-glycidyl denotes

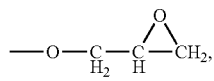

O-vinyl is

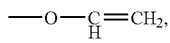

O-allyl means

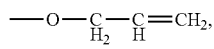

Halogen is fluorine, chlorine, bromine or iodine, especially chlorine or fluorine, preferably fluorine.

Phenylene is

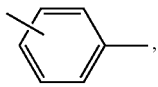

o-phenylene means, ortho-phenylene

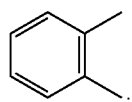

If $L_3$ and $L_5$, $L'_3$ and $L'_5$ or $L''_3$ and $L''_5$ together denote a single bond or an organic linking group, the organic linking group for example is $CR_aR_b$, CO, O, S, $NR_c$ or $NCOR_c$, and for example the following structural units are formed, provided that $L_3$ and $L_5$, $L'_3$ and $L'_5$ or $L''_3$ and $L''_5$ together denote no single bond if the respective X, X' or X" is a single bond,

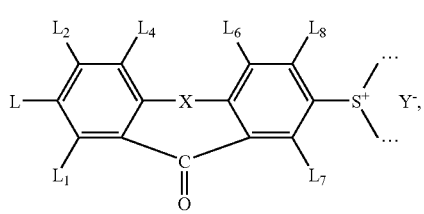

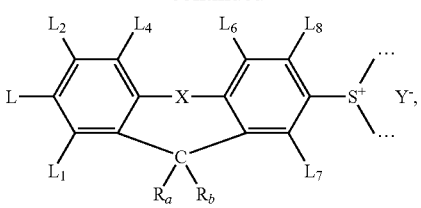

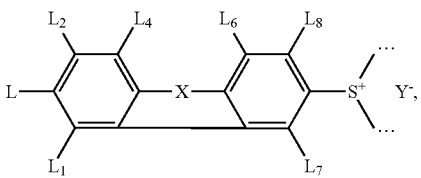

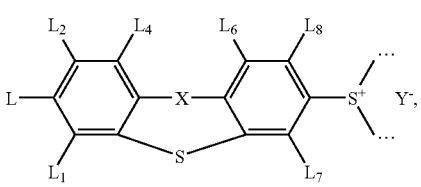

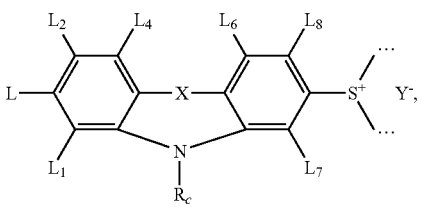

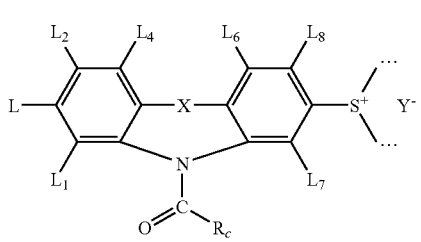

If $L_1$ and $L_3$, $L_1$ and L, $L_5$ and $L_7$, $L'_1$ and $L'_3$, $L'_1$ and L', $L'_5$ and $L'_7$, $L''_1$ and $L''_3$, $L''_1$ and L" or $L''_5$ and $L''_7$, together denote an organic linking group; said organic linking group is for example represented by $C_3$-$C_4$alkylene, $CR_1$=$CR_2$—$CR_3$=$CR_4$, $CR_1$=$CR_2$—O, $CR_1$=$CR_2$—S, $CR_1$=$CR_2$—$NR_1$, CO—O—CO, $CONR_1CO$, CO-(o-phenylene)-S, CO-(o-phenylene)-S substituted by one or more D, or are $C_1$-$C_3$alkylene interrupted by O, S, $NR_1$ or $NCOR_1$; and for example the following structural units are formed

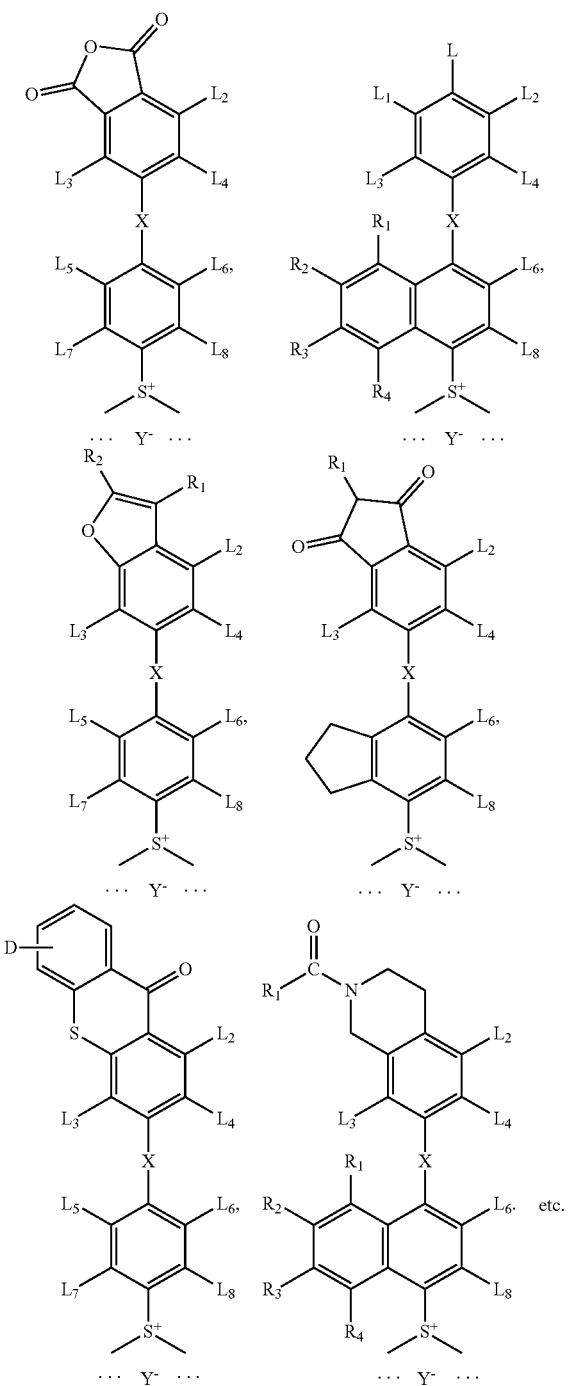

Examples for Y as an organic or inorganic anion are halogenide, ClO$_4$, CN, hydrogenosulfate, trifluoroacetate; or for example non-nucleophilic anions, selected from the group (BZ$_4$)$^-$, (SbZ$_6$)$^-$, (AsZ$_6$)$^-$, (PZ$_6$)$^-$, (B(C$_6$Z$_5$)$_4$)$^-$, with Z denoting a halogen, in particular F or Cl, preferably F; C$_1$-C$_{20}$alkylsulphonate, C$_1$-C$_{20}$haloalkylsulphonate, C$_1$-C$_{20}$ perfluoroalkylsulphonate, unsubstituted C$_6$-C$_{10}$arylsulphonate, camphorsulphonate, C$_1$-C$_{20}$-perfluoroalkylsulphonylmethide, C$_1$-C$_{20}$-perfluoroalkylsulphonylimide, and C$_6$-C$_{10}$arylsulphonate substituted by halogen, NO$_2$, SO$_3$M, C$_1$-C$_{12}$alkyl, C$_1$-C$_{12}$haloalkyl, C$_1$-C$_{12}$alkoxy, phenylsulphonyloxy, C$_1$-C$_4$alkylphenylsulphonyloxy or by COOR$_{100}$; wherein R$_{100}$ is C$_1$-C$_{20}$alkyl, phenyl, benzyl; or phenyl mono- or poly-substituted by C$_1$-C$_{12}$alkyl, C$_1$-C$_{12}$alkoxy or by halogen and M is as defined above.

C$_1$-C$_{20}$Alkylsulphonate is R$_x$SO$_3$$^-$ wherein R$_x$ is linear or branched C$_1$-C$_{20}$alkyl as described above. Examples thereof include methylsulphonate, ethylsulphonate, propylsulphonate, pentylsulphonate and hexylsulphonate.

C$_2$-C$_{20}$Haloalkylsulphonate is R$_x$SO$_3$$^-$ wherein R$_x$ is halo-substituted C$_2$-C$_{20}$alkyl, C$_2$-C$_{10}$-, C$_2$-C$_8$— or C$_4$-C$_8$-alkyl. Examples thereof include C$_2$F$_5$SO$_3$$^-$, C$_4$F$_9$SO$_3$$^-$ and C$_8$F$_{17}$SO$_3$$^-$.

C$_6$-C$_{10}$Arylsulphonate is R$_x$SO$_3$$^-$ wherein R$_x$ is C$_6$-C$_{10}$aryl, e.g. phenyl or naphthyl.

Alkyl-substituted arylsulphonates are, for example, toluenesulphonate, 2,4,6-trimethylbenzene-sulphonate, 2,4,6-tris(isopropyl)benzenesulphonate, 4-tert-butylbenzenesulphonate and 4-dodecylbenzenesulphonate.

Halo-substituted arylsulphonates are, for example, 4-chlorobenzenesulphonate, 4-fluorobenzenesulphonate, 2,4,6-trifluorobenzenesulphonate and pentafluorobenzenesulphonate.

Camphorsulphonate is

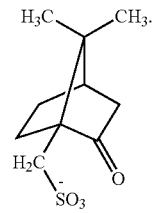

C$_1$-C$_{20}$-Perfluoroalkylsulphonylmethide is

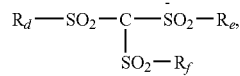

C$_1$-C$_{20}$-perfluoroalkylsulphonylimide is

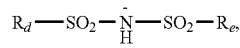

wherein R$_d$, R$_e$ and R$_f$ independently of one another are C$_1$-C$_{20}$ perfluoroalkyl which is unsubstituted or is substituted by N(R$_g$)(R$_h$), or R$_d$, R$_e$ and R$_f$ are phenyl substituted by CF$_3$; or R$_d$ and R$_e$ together are C$_1$-C$_6$-perfluoroalkylene, which optionally is interrupted by —O—; R$_g$ and R$_h$ independently of one another are C$_1$-C$_{12}$alkyl or R$_g$ and R$_h$ together are C$_1$-C$_6$ perfluoroalkylene, which optionally is interrupted by O or N(C$_1$-C$_{12}$-Alkyl).

Perfluoroalkyl is alkyl which is fully substituted by fluoro, i.e. the hydrogen atoms of the alkyl radical are replaced by fluoro. The same applies for the perfluoroalkylene.

Examples of such anions are (C$_2$F$_5$SO$_2$)$_2$N$^-$, (C$_4$F$_9$SO$_2$)$_2$N$^-$, (C$_8$F$_{17}$SO$_2$)$_3$C$^-$, (CF$_3$SO$_2$)$_3$C$^-$, (CF$_3$SO$_2$)$_2$N$^-$, (C$_4$F$_9$SO$_2$)$_3$C$^-$, (CF$_3$SO$_2$)$_2$(C$_4$F$_9$SO$_2$)C$^-$, (CF$_3$SO$_2$)(C$_4$F$_9$SO$_2$)N$^-$, [(3,5-bis(CF$_3$)—(C$_6$H$_3$)SO$_2$]$_2$N$^-$,

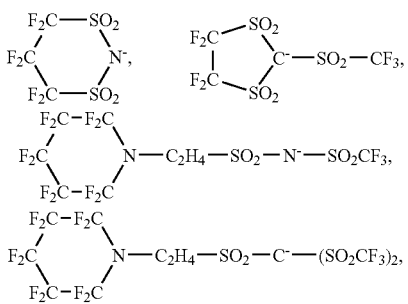

$C_6F_5SO_2C^-(SO_2CF_3)_2$, $C_6F_5SO_2N^-SO_2CF_3$. Such anions are known the person skilled in the art. The anions as well as their preparation are described e.g. in U.S. Pat. No. 5,554,664.

Y as organic or inorganic anion, for example is halogen or a non-nucleophilic anion, selected from the group $C_fF_{2f+1}SO_3^-$, $(BZ_4)^-$, $(SbZ_6)^-$, $(AsZ_6)^-$, $(PZ_6)^-$ and $(B(C_6Z_5)_4)^-$; wherein Z is a halogen; and f is an integer from 1 to 8.

Y in particular is halogen or a non-nucleophilic anion, selected from the group $C_fF_{2f+1}SO_3^-$, $(BF_4)^-$, $(SbF_6)^-$, $(AsF_6)^-$, $(PF_6)^-$ and $(B(C_6F_5)_4)^-$; wherein f is an integer from 1 to 8.

M as an organic or inorganic cation, for example is Li, Na, K, Cs, $N(R_a)_4$, $N(R_a)_3R_b$, $N(R_a)_2R_bR_c$, $P(R_a)_4$, $P(R_a)_3R_b$, $P(R_a)_2R_bR_c$, $S(R_a)_3$, $S(R_a)_2R_b$ or $SR_aR_bR_c$.

M preferably is Li, Na, K, $N(R_a)_4$, $N(R_a)_3R_b$, $N(R_a)_2R_bR_c$, $S(R_a)_3$, $S(R_a)_2R_b$, $SR_aR_bR_c$; in particular Na, K, $N(R_a)_4$, $N(R_a)_3R_b$, $S(R_a)_3$ or $S(R_a)_2R_b$.

The terms "and/or" or "or/and" in the present context are meant to express that not only one of the defined alternatives (substituents) may be present, but also several of the defined alternatives (substituents) together, namely mixtures of different alternatives (substituents).

The term "at least" is meant to define one or more than one, for example one or two or three, preferably one or two.

The term "optionally substituted" means that the radical to which it refers is either unsubstituted or substituted.

Throughout this specification and the claims which follow, unless the context requires otherwise, the word "comprise", or variations such as "comprises" or "comprising", will be understood to imply the inclusion of a stated integer or step or group of integers or steps but not the exclusion of any other integer or step or group of integers or steps.

Interesting are compounds of the formula I and Ia as defined above, wherein L, L', L", $L_1$, $L'_1$, $L"_1$, $L_2$, $L'_2$, $L"_2$, $L_3$, $L'_3$, $L"_3$, $L_4$, $L'_4$ and $L"_4$ independently of one another are hydrogen, $R_1$, $OR_1$, $SR_1$, halogen, $NO_2$, CN, $NR_1COR_2$, $COOR_1$, $OCOR_1$, $CONR_1R_2$, $OCOOR_1$, $OCONR_1R_2$, $NR_1COOR_2$, $SO_3H$, $SO_3M$, $SOR_1$, $SO_2R_1$ or COT;

$L_5$, $L'_5$, $L"_5$, $L_6$, $L'_6$, $L"_6$, $L_7$, $L'_7$, $L"_7$, $L_8$, $L'_8$ and $L"_8$ independently of one another are hydrogen, $R_1$, $OR_1$, $SR_1$, halogen; and/or one or more of the pairs $L_3$ and $L_5$, $L'_3$ and $L'_5$ or $L"_3$ and $L"_5$ together are a single bond, $CR_aR_b$, CO, O, S, $NR_c$ or $NCOR_c$; provided that $L_3$ and $L_5$, $L'_3$ and $L'_5$, $L"_3$ and $L"_5$ together are no single bond, when the respective X, X' or X" denotes a single bond; and/or one or more of the pairs $L_1$ and $L_3$, $L_1$ and L, $L_5$ and $L_7$, $L'_1$ and $L'_3$, $L'_1$ and L', $L'_5$ and $L'_7$, $L"_1$ and $L"_3$, $L"_1$ and L" or $L"_5$ and $L"_7$, together are $C_3$-$C_4$alkylene, $CR_1=CR_2$—$CR_3=CR_4$, $CR_1=CR_2$—O, $CR_1=CR_2$—S, $CR_1=CR_2$—$NR_1$, CO—O—CO, $CONR_1CO$, CO-(o-phenylene)-S, CO-(o-phenylene)-S substituted by one or more D, or are $C_1$-$C_3$alkylene interrupted by O, S, $NR_1$ or $NCOR_1$;

provided that at least one of L, L', L", $L_1$, $L'_1$, $L"_1$, $L_2$, $L'_2$, $L"_2$, $L_3$, $L'_3$, $L"_3$, $L_4$, $L'_4$, $L"_4$, $L_5$, $L'_5$, $L"_5$, $L_6$, $L'_6$, $L"_6$, $L_7$, $L'_7$, $L"_7$, $L_8$, $L'_8$, $L"_8$ is other than hydrogen;

$T_1$ and $T_2$ independently of one another are hydrogen, $C_1$-$C_{20}$alkyl, $C_5$-$C_{12}$cycloalkyl, $C_2$-$C_{20}$alkenyl, $C_6$-$C_{14}$aryl, $C_1$-$C_{20}$alkyl substituted by one or more D, $C_2$-$C_{20}$alkyl interrupted by one or more E, $C_2$-$C_{20}$alkyl substituted by one or more D and interrupted by one or more E, $C_5$-$C_{12}$cycloalkyl substituted by one or more D, $C_2$-$C_{12}$cycloalkyl interrupted by one or more E, $C_2$-$C_{12}$cycloalkyl substituted by one or more D and interrupted by one or more E, $C_2$-$C_{20}$alkenyl substituted by one or more D, $C_3$-$C_{20}$alkenyl interrupted by one or more E, $C_3$-$C_{20}$alkenyl substituted by one or more D and interrupted by one or more E, or $C_6$-$C_{14}$aryl substituted by one or more D;

X, X' and X" independently of one another are a single bond, $CR_aR_b$, O, S, $NR_c$ or $NCOR_c$;

$R_1$, $R_2$, $R_3$, $R_4$, $R_a$, $R_b$ and $R_c$ independently of one another have the meaning of $T_1$;

T is T, or O-$T_2$;

D is hydrogen, $R_5$, $OR_5$, $SR_5$, halogen, $NO_2$, CN, O-glycidyl, O-vinyl, O-allyl, $COR_5$, $NR_5COR_6$, $COOR_5$, $OCOR_5$, $CONR_5R_6$, $OCOOR_5$, $OCONR_5R_6$, $NR_5COOR_6$, $SO_3H$ or $SO_3M$;

E is O, S, COO, OCO, CO, $NCOR_5$, $NR_5CO$, $CONR_5$, OCOO, $OCONR_5$, $NR_5COO$, $SO_2$ or SO, $CR_5=CR_6$;

$R_5$ and $R_6$ independently of one another are hydrogen, $C_1$-$C_{12}$alkyl, phenyl;

Y is an inorganic or organic anion; and

M is an inorganic or organic cation.

Interesting are compounds of the formula I and Ia as defined above, wherein L, L', L", $L_1$, $L'_1$, $L"_1$, $L_2$, $L'_2$, $L"_2$, $L_3$, $L'_3$, $L"_3$, $L_4$, $L'_4$ and $L"_4$ independently of one another are hydrogen, $R_1$, $OR_1$, $SR_1$, halogen, $NO_2$, CN, $COOR_1$, $SO_3H$, $SO_3M$, $SOR_1$, $SO_2R_1$ or COT;

$L_5$, $L'_5$, $L"_5$, $L_6$, $L'_6$, $L"_6$, $L_7$, $L'_7$, $L"_7$, $L_8$, $L'_8$ and $L"_8$ independently of one another are hydrogen, $R_1$, $OR_1$, halogen; and/or one or more of the pairs $L_3$ and $L_5$, $L'_3$ and $L'_5$ or $L"_3$ and $L"_5$ together are a single bond, $CR_aR_b$, CO, O or S; provided that $L_3$ and $L_5$, $L'_3$ and $L'_5$, $L"_3$ and $L"_5$ together are no single bond, when the respective X, X' or X" denotes a single bond; and/or one or more of the pairs $L_1$ and $L_3$, $L_1$ and L, $L_5$ and $L_7$, $L'_1$ and $L'_3$, $L'_1$ and L', $L'_5$ and $L'_7$, $L"_1$ and $L"_3$, $L"_1$ and L" or $L"_5$ and $L"_7$, together are $C_3$-$C_4$alkylene, $CR_1=CR_2$—$CR_3=CR_4$, $CR_1=CR_2$—O, $CR_1=CR_2$—S, $CR_1=CR_2$—$NR_1$, CO—O—CO, $CONR_1CO$, CO-(o-phenylene)-S or CO-(o-phenylene)-S substituted by one or more D;

provided that at least one of L, L', L", $L_1$, $L'_1$, $L"_1$, $L_2$, $L'_2$, $L"_2$, $L_3$, $L'_3$, $L"_3$, $L_4$, $L'_4$, $L"_4$, $L_5$, $L'_5$, $L"_5$, $L_6$, $L'_6$, $L"_6$, $L_7$, $L'_7$, $L"_7$, $L_8$, $L'_8$, $L"_8$ is other than hydrogen;

$T_1$ and $T_2$ are independently of one another hydrogen, $C_1$-$C_{20}$alkyl, $C_5$-$C_{12}$cycloalkyl, $C_2$-$C_{20}$alkenyl, $C_6$-$C_{14}$aryl, $C_1$-$C_{20}$alkyl substituted by one or more D, $C_2$-$C_{20}$alkyl interrupted by one or more E, $C_2$-$C_{20}$alkyl substituted by one or more D and interrupted by one or more E, $C_5$-$C_{12}$cycloalkyl substituted by one or more D, $C_2$-$C_{12}$cycloalkyl interrupted by one or more E, $C_2$-$C_{12}$cycloalkyl substituted by one or more D and interrupted by one or more E, $C_2$-$C_{20}$alkenyl substituted by one or more D, $C_3$-$C_{20}$alkenyl interrupted by one or more E, $C_3$-$C_{20}$alkenyl substituted by one or more D and interrupted by one or more E, $C_6$-$C_{14}$aryl substituted by one or more D;

$R_1$, $R_2$, $R_3$, $R_4$, $R_a$, $R_b$ and $R_c$ independently of one another have the meaning of $T_1$;

T is $T_1$ or O-$T_2$;

X, X' and X" independently of one another are a single bond, $CR_aR_b$, O, S, $NR_c$ or $NCOR_c$;

D is hydrogen, $R_5$, $OR_5$, $SR_5$, halogen, $NO_2$, CN, O-glycidyl, O-vinyl, O-allyl, $COR_5$, $COOR_5$, $OCOR_5$, $SO_3H$ or $SO_3M$;

E is O, S, COO, OCO, CO, $SO_2$, SO or $CR_5$=$CR_6$;

$R_5$ and $R_6$ independently of one another are hydrogen, $C_1$-$C_{12}$alkyl or phenyl;

Y is an inorganic or organic anion; and

M is an inorganic or organic cation;

Interesting are compounds of the formula I and Ia as defined above, wherein L, L', L", $L_1$, $L'_1$, $L"_1$, $L_2$, $L'_2$, $L"_2$, $L_3$, $L'_3$, $L"_3$, $L_4$, $L'_4$ and $L"_4$ independently of one another are hydrogen, $R_1$, $OR_1$, halogen, $NO_2$, CN, $COOR_1$, $SO_3H$, $SO_3M$, $SOR_1$, $SO_2R_1$ or COT;

$L_5$, $L'_5$, $L"_5$, $L_6$, $L'_6$, $L"_6$, $L_7$, $L'_7$, $L"_7$, $L_8$, $L'_8$ and $L"_8$ independently of one another are hydrogen, $R_1$ or $OR_1$; and/or one or more of the pairs $L_3$ and $L_5$, $L'_3$ and $L'_5$ or $L"_3$ and $L"_5$ together are a single bond, $CR_aR_b$, CO, O or S; provided that $L_3$ and $L_5$, $L'_3$ and $L'_5$, $L"_3$ and $L"_5$ together are no single bond, when the respective X, X', X" denotes a single bond; and/or one or more of the pairs $L_1$ and $L_3$, $L_1$ and L, $L_5$ and $L_7$, $L'_1$ and $L'_3$, $L'_1$ and L', $L'_5$ and $L'_7$, $L"_1$ and $L"_3$, $L"_1$ and L" or $L"_5$ and $L"_7$, together are $C_3$-$C_4$alkylene, $CR_1$=$CR_2$—$CR_3$=$CR_4$, $CR_1$=$CR_2$—O, $CR_1$=$CR_2$—S, $CR_1$=$CR_2$—$NR_1$, CO—O—CO, $CONR_1CO$, CO-(o-phenylene)-S or CO-(o-phenylene)-S substituted by one or more D;

provided that at least one of L, L', L", $L_1$, $L'_1$, $L"_1$, $L_2$, $L'_2$, $L"_2$, $L_3$, $L'_3$, $L"_3$, $L_4$, $L'_4$, $L"_4$, $L_5$, $L'_5$, $L"_5$, $L_6$, $L'_6$, $L"_6$, $L_7$, $L'_7$, $L"_7$, $L_8$, $L'_8$, $L"_8$ is other than hydrogen;

$T_1$ and $T_2$ are independently of one another hydrogen, $C_1$-$C_{20}$alkyl, $C_5$-$C_{12}$cycloalkyl, $C_2$-$C_{20}$alkenyl, $C_6$-$C_{14}$aryl, $C_1$-$C_{20}$alkyl substituted by one or more D, $C_2$-$C_{20}$alkyl interrupted by one or more E, $C_2$-$C_{20}$alkyl substituted by one or more D and interrupted by one or more E, $C_5$-$C_{12}$cycloalkyl substituted by one or more D, $C_2$-$C_{12}$cycloalkyl interrupted by one or more E, $C_2$-$C_{12}$cycloalkyl substituted by one or more D and interrupted by one or more E, $C_2$-$C_{20}$alkenyl substituted by one or more D, $C_3$-$C_{20}$alkenyl interrupted by one or more E, $C_3$-$C_{20}$alkenyl substituted by one or more D and interrupted by one or more E, or $C_6$-$C_{14}$aryl substituted by one or more D;

$R_1$, $R_2$, $R_3$, $R_4$, $R_a$, $R_b$ and $R_c$ independently of one another have the meaning of $T_1$;

T is $T_1$ or O-$T_2$;

X, X' and X" independently of one another are a single bond, $CR_aR_b$, O, S, $NR_c$ or $NCOR_c$;

D is hydrogen, $R_5$, $OR_5$, $SR_5$, halogen, $NO_2$, CN, O-glycidyl, O-vinyl, O-allyl, $COR_5$, $COOR_5$ or $OCOR_5$;

E is O, S, COO, OCO, CO or $CR_5$=$CR_6$;

$R_5$ and $R_6$ independently of one another are hydrogen, $C_1$-$C_{12}$alkyl or phenyl;

Y is an inorganic or organic anion; and

M is an inorganic or organic cation.

Interesting further are compounds of the formula Ia, wherein

L, $L_1$, $L_2$, $L_3$, and $L_4$ independently of one another are hydrogen, $R_1$, $OR_1$, halogen, $SO_3H$, $SO_3M$, $SOR_1$, $SO_2R_1$, CN, $NO_2$ or COT;

$L_5$, $L_6$, $L_7$ and $L_8$ independently of one another are hydrogen, $R_1$ or $OR_1$;

provided that at least one of L, $L_1$, $L_2$, $L_3$, $L_4$ is $SO_3H$, $SO_3M$, $SO_2R_1$, CN, $NO_2$ or COT;

$T_1$ and $T_2$ independently of one another are hydrogen, $C_1$-$C_{20}$alkyl, $C_5$-$C_{12}$cycloalkyl, $C_2$-$C_{20}$alkenyl, $C_6$-$C_{14}$aryl, $C_1$-$C_{20}$alkyl substituted by one or more D, $C_2$-$C_{20}$alkyl interrupted by one or more E, $C_2$-$C_{20}$alkyl substituted by one or more D and interrupted by one or more E, $C_5$-$C_{12}$cycloalkyl substituted by one or more D, $C_2$-$C_{12}$cycloalkyl interrupted by one or more E, $C_2$-$C_{12}$cycloalkyl substituted by one or more D and interrupted by one or more E, $C_2$-$C_{20}$alkenyl substituted by one or more D, $C_3$-$C_{20}$alkenyl interrupted by one or more E, $C_3$-$C_{20}$alkenyl substituted by one or more D and interrupted by one or more E, $C_6$-$C_{14}$aryl substituted by one or more D;

$R_1$, $R_a$, $R_b$ and $R_c$ independently of one another have the meaning of $T_1$;

T is $T_1$ or O-$T_2$;

X, X' and X" independently of one another are a single bond, $CR_aR_b$, O, S, $NR_c$ or $NCOR_c$;

D is hydrogen, $R_5$, $OR_5$, $SR_5$, halogen, $NO_2$, CN, O-glycidyl, O-vinyl, O-allyl, $COR_5$, $COOR_5$ or $OCOR_5$;

E is O, S, COO, OCO, CO or $CR_5$=$CR_6$;

$R_5$ and $R_6$ independently of one another are hydrogen, $C_1$-$C_{12}$alkyl or phenyl;

Y is an inorganic or organic anion; and

M is an inorganic or organic cation.

Further interesting are compounds of the formula I or Ia, wherein

L, L', L", $L_1$, $L'_1$, $L"_1$, $L_2$, $L'_2$, $L"_2$, $L_3$, $L'_3$, $L"_3$, $L_4$, $L'_4$ and $L"4$ independently of one another are hydrogen, $R_1$, $OR_1$, $NO_2$ or COT;

$L_5$, $L'_5$, $L"_5$, $L_6$, $L'_6$, $L"_6$, $L_7$, $L'_7$, $L"_7$, $L_8$, $L'_8$ and $L"_8$ independently of one another are hydrogen, $R_1$ or $OR_1$;

provided that at least one of L, L', L", $L_1$, $L'_1$, $L"_1$, $L_2$, $L'_2$, $L"_2$, $L_3$, $L'_3$, $L"_3$, $L_4$, $L'_4$, $L"_4$ is $NO_2$ or COT;

$T_1$ and $T_2$ are independently of one another hydrogen, $C_1$-$C_{20}$alkyl, $C_5$-$C_{12}$cycloalkyl, $C_2$-$C_{20}$alkenyl, $C_6$-$C_{14}$aryl, $C_1$-$C_{20}$alkyl substituted by one or more D, $C_2$-$C_{20}$alkyl interrupted by one or more E, $C_2$-$C_{20}$alkyl substituted by one or more D and interrupted by one or more E, $C_5$-$C_{12}$cycloalkyl substituted by one or more D, $C_2$-$C_{12}$cycloalkyl interrupted by one or more E, $C_2$-$C_{12}$cycloalkyl substituted by one or more D and interrupted by one or more E, $C_2$-$C_{20}$alkenyl substituted by one or more D, $C_3$-$C_{20}$alkenyl interrupted by one or more E, $C_3$-$C_{20}$alkenyl substituted by one or more D and interrupted by one or more E, or $C_6$-$C_{14}$aryl substituted by one or more D;

$R_1$, $R_a$, $R_b$, $R_c$ independently of one another have the meaning of $T_1$;

T is $T_1$ or O-$T_2$;

X, X' and X" independently of one another are a single bond, $CR_aR_b$, O, S, $NR_c$ or $NCOR_c$;

D is hydrogen, $R_5$, $OR_5$, $SR_5$, halogen, $NO_2$, CN, O-glycidyl, O-vinyl, O-allyl, $COR_5$, $COOR_5$, or $OCOR_5$;

E is O, S, COO, OCO, CO, or $CR_5$=$CR_6$;

$R_5$ and $R_6$ independently of one another are hydrogen, $C_1$-$C_{12}$alkyl, phenyl; and Y is an inorganic or organic anion.

Most interesting are symmetrical compounds of the formula I, that is compounds of the formula I, wherein L, L' and L" are identical and $L_1$, $L'_1$ and $L"_1$ are identical and $L_2$, $L'_2$ and $L"_2$ are identical and $L_3$, $L'_3$ and $L"_3$ are identical and $L_4$, $L'_4$ and $L"_4$ are identical and $L_5$, $L'_5$ and $L"_5$ are identical and $L_6$, $L"_6$ and $L"_6$ are identical and $L_7$, $L'_7$ and $L"_7$ are identical and $L_8$, $L'_8$ and $L"_8$ are identical and X, X' and X" are identical, namely compounds of the formula Ia

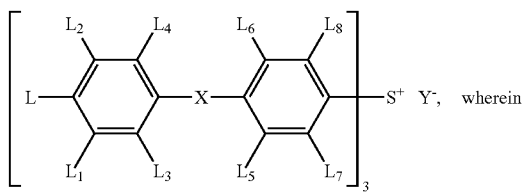

L, $L_1$, $L_2$, $L_3$, $L_4$, $L_5$, $L_6$, $L_7$, $L_8$, X and Y are as defined above.

Another embodiment of the invention is a compound of the formula Ia, wherein

L, $L_1$, $L_2$, $L_3$ and $L_4$ independently of one another are hydrogen, $NO_2$, $R_1$, $OR_1$ or COT;

$L_5$, $L_6$, $L_7$ and $L_8$ independently of one another are hydrogen, $R_1$ or $OR_1$;

provided that at least one of L, $L_1$, $L_2$, $L_3$, $L_4$ is $NO_2$ or COT;

$T_1$ is hydrogen, $C_1$-$C_{20}$alkyl, $C_5$-$C_{12}$cycloalkyl, $C_6$-$C_{14}$aryl, $C_6$-$C_{14}$aryl substituted by one or more $C_1$-$C_4$alkyl, halogen or $C_1$-$C_4$alkoxy;

T is $T_1$ or O-$T_2$;

$T_2$ is hydrogen, $C_1$-$C_{20}$alkyl, $C_5$-$C_{12}$cycloalkyl, $C_6$-$C_{14}$aryl, $C_1$-$C_{20}$alkyl substituted by one or more D, $C_2$-$C_{20}$alkyl interrupted by one or more E, $C_2$-$C_{20}$alkyl substituted by one or more D and interrupted by one or more E, $C_5$-$C_{12}$cycloalkyl substituted by one or more D, $C_2$-$C_{12}$cycloalkyl interrupted by one or more E, $C_2$-$C_{12}$cycloalkyl substituted by one or more D and interrupted by one or more E, or $C_6$-$C_{14}$aryl substituted by one or more D;

X is O or S;

D is hydrogen, $R_5$, $OR_5$, halogen, O-glycidyl, O-vinyl, O-allyl, $COR_5$, $COOR_5$ or $OCOR_5$;

E is O, COO, OCO or CO;

$R_1$, $R_2$, $R_5$ and $R_6$ independently of one another are hydrogen, $C_1$-$C_{12}$alkyl or phenyl; and Y is an inorganic or organic anion.

Preferred are compounds of the formula Ia, wherein

L, $L_1$, $L_2$, $L_3$ and $L_4$, independently of one another are hydrogen, $R_1$, $OR_1$ or COT;

$L_5$, $L_6$, $L_7$ and $L_8$ are hydrogen; provided that at least one of L, $L_1$, $L_2$, $L_3$, $L_4$ is COT;

$T_1$ is hydrogen, $C_1$-$C_{20}$alkyl, $C_5$-$C_{12}$cycloalkyl, $C_6$-$C_{14}$aryl, or is $C_6$-$C_{14}$aryl substituted by one or more $C_1$-$C_4$ alkyl, halogen or $C_1$-$C_4$ alkoxy;

T is $T_1$ or O-$T_2$;

$T_2$ is hydrogen, $C_1$-$C_{20}$alkyl, $C_5$-$C_{12}$cycloalkyl, $C_6$-$C_{14}$aryl, $C_1$-$C_{20}$alkyl substituted by one or more O-glycidyl, O-vinyl, O-allyl, $R_5$, $OR_5$, $COOR_5$ and/or optionally interrupted by one or more O, $C_2$-$C_{12}$cycloalkyl interrupted by one or more O, or is $C_6$-$C_{14}$aryl substituted by one or more $C_1$-$C_4$alkyl, halogen or $C_1$-$C_4$alkoxy;

X is O or S;

$R_1$ and $R_5$ independently of one another are hydrogen, $C_1$-$C_{12}$alkyl or phenyl; and Y is an inorganic or organic anion.

Further preferred are compounds of the formula Ia, wherein

L, $L_1$, $L_2$, $L_3$ and $L_4$, independently of one another are hydrogen or COT;

$L_5$, $L_6$, $L_7$ and $L_8$ are hydrogen; provided that at least one of L, $L_1$, $L_2$, $L_3$, $L_4$ is COT;

$T_1$ is hydrogen, $C_1$-$C_{20}$alkyl, $C_5$-$C_{12}$cycloalkyl, $C_6$-$C_{14}$aryl, or is $C_6$-$C_{14}$aryl substituted by one or more $C_1$-$C_4$ alkyl, halogen or $C_1$-$C_4$ alkoxy;

T is $T_1$ or O-$T_2$;

$T_2$ is hydrogen, $C_1$-$C_{20}$alkyl, $C_5$-$C_{12}$cycloalkyl, $C_6$-$C_{14}$aryl, $C_1$-$C_{20}$alkyl substituted by one or more O-glycidyl, O-vinyl, O-allyl, $R_5$, $OR_5$, $COOR_5$ and/or optionally interrupted by one or more O, $C_2$-$C_{12}$cycloalkyl interrupted by one or more O, or is $C_6$-$C_{14}$aryl substituted by one or more $C_1$-$C_4$ alkyl, halogen or $C_1$-$C_4$ alkoxy;

X is O or S;

$R_5$ is hydrogen, $C_1$-$C_{12}$alkyl or phenyl; and

Y is an inorganic or organic anion.

Other interesting compounds according to the invention are compounds of the formula I wherein L, $L_1$, $L_2$, $L_3$ and $L_4$, independently of one another are hydrogen or COT;

$L_5$, $L_6$, $L_7$ and $L_8$ are hydrogen; provided that at least one of L, $L_1$, $L_2$, $L_3$, $L_4$ is COT;

$T_1$ is hydrogen, $C_1$-$C_{20}$alkyl, $C_5$-$C_{12}$cycloalkyl, $C_6$-$C_{14}$aryl, or is $C_6$-$C_{14}$aryl substituted by one or more $C_1$-$C_4$alkyl, halogen or $C_1$-$C_4$alkoxy;

T is $T_1$ or O-$T_2$;

$T_2$ is hydrogen, $C_1$-$C_{20}$alkyl, or is $C_1$-$C_{20}$alkyl substituted by one or more $R_5$, $OR_5$ or $COOR_5$ and/or optionally interrupted by one or more O;

X is O or S;

$R_5$ is hydrogen, $C_1$-$C_{12}$alkyl or phenyl; and

Y is a halogen or a non-nucleophilic anion, selected from the group $C_1$-$C_{20}$-perfluoroalkylsulphonylmethide, $C_fF_{2f+1}SO_3^-$, $(BZ_4)^-$, $(SbZ_6)^-$, $(AsZ_6)^-$, $(PZ_6)^-$ and $(B(C_6Z_5)_4)^-$;

Z is a halogen; and f is an integer from 1 to 8.

Another embodiment of the invention are compounds of the formula I, wherein

L is COT;

$L_1$, $L_2$, $L_3$, $L_4$, $L_5$, $L_6$, $L_7$ and $L_8$ are hydrogen;

$T_1$ is hydrogen, $C_1$-$C_{20}$alkyl, $C_5$-$C_{12}$cycloalkyl, $C_6$-$C_{14}$aryl, or is $C_6$-$C_{14}$aryl substituted by one or more $C_1$-$C_4$ alkyl, halogen or $C_1$-$C_4$ alkoxy;

T is $T_1$ or O-$T_2$;

$T_2$ is hydrogen, $C_1$-$C_{20}$alkyl, or is $C_1$-$C_{20}$alkyl substituted by one or more $OR_5$, $COOR_5$ and/or optionally interrupted by one or more O;

X is O or S;

$R_5$ is hydrogen, $C_1$-$C_{12}$alkyl or phenyl;

Y is a halogen or a non-nucleophilic anion, selected from the group $C_fF_{2f+1}SO_3^-$, $C_1$-$C_{20}$-perfluoroalkylsulphonylmethide, $(BF_4)^-$, $(SbF_6)^-$, $(AsF_6)^-$, $(PF_6)^-$, $(B(C_6F_5)_4)^-$; and f is an integer from 1 to 8.

L, L', L", $L_1$, $L'_1$, $L"_1$, $L_2$, $L'_2$, $L"_2$, $L_3$, $L'_3$, $L"_3$, $L_4$, $L'_4$ and $L"_4$ independently of one another are hydrogen, $R_1$, $OR_1$, $SR_1$, halogen, $NO_2$, CN, $COR_1$, $NR_1COR_2$, $COOR_1$, $OCOR_1$, $CONR_1R_2$, $OCOOR_1$, $OCONR_1R_2$, $NR_1COOR_2$, $SO_3H$, $SO_3M$, $SOR_1$, $SO_2R_1$ or COT; or for example independently of one another are hydrogen, $R_1$, $OR_1$, $SR_1$, halogen, $NO_2$, CN, $COR_1$, $COOR_1$, $SO_3H$, $SO_3M$, $SOR_1$, $SO_2R_1$ or COT; or e.g. independently of one another are hydrogen, $R_1$, $OR_1$, halogen, $NO_2$, CN, $COR_1$, $COOR_1$, $SO_3H$, $SO_3M$, $SOR_1$, $SO_2R_1$ or COT; in particular L, L', L", $L_1$, $L'_1$, $L"_1$, $L_2$, $L'_2$, $L''_2$, $L_3$, $L'_3$, $L''_3$, $L_4$, $L'_4$ and $L''_4$ independently of one another are hydrogen, $R_1$, $OR_1$, halogen, $SO_3H$, $SO_3M$, $SOR_1$, $SO_2R_1$, CN, $NO_2$ or COT; or for example L, L', L'', $L_1$, $L'_1$, $L''_1$, $L_2$, $L'_2$, $L''_2$, $L_3$, $L'_3$, $L''_3$, $L_4$, $L'_4$ and $L''_4$ independently of one another are hydrogen, $R_1$, $OR_1$, $NO_2$ or COT; especially L, $L_1$, $L_2$, $L_3$ and $L_4$ independently of one another are hydrogen, $NO_2$, $R_1$, $OR_1$ or COT; preferably L, $L_1$, $L_2$, $L_3$ and $L_4$, independently of one another are hydrogen, $R_1$, $OR_1$ or COT; especially L, $L_1$, $L_2$, $L_3$ and $L_4$, independently of one another are hydrogen or COT.

$L_5$, $L'_5$, $L''_5$, $L_6$, $L'_6$, $L''_6$, $L_7$, $L'_7$, $L''_7$, $L_8$, $L'_8$ and $L''_8$ independently of one another are hydrogen, $R_1$, $OR_1$, $SR_1$, halogen, $NO_2$, CN, $COR_1$, $NR_1COR_2$, $COOR_1$, $OCOR_1$, $CONR_1R_2$, $OCOOR_1$, $OCONR_1R_2$, $NR_1COOR_2$, $SO_3H$, $SO_3M$, $SOR_1$, $SO_2R_1$ or COT (weil ja im ersten claim L5-L8 wie L1 ist); or for example independently of one another are hydrogen, $R_1$, $OR_1$, $SR_1$, halogen, O-glycidyl, O-vinyl or O-allyl; and/or one or more of the pairs $L_3$ and $L_5$, $L'_3$ and $L'_5$ or $L''_3$ and $L''_5$ together are a single bond, $CR_aR_b$, CO, O, S, $NR_c$ or $NCOR_c$; provided that $L_3$ and $L_5$, $L'_3$ and $L'_5$, $L''_3$ and $L''_5$ together are no single bond, when the respective X, X' or X'' denotes a single bond; and/or one or more of the pairs $L_1$ and $L_3$, $L_1$ and L, $L_5$ and $L_7$, $L'_1$ and $L'_3$, $L'_1$ and L', $L'_5$ and $L'_7$, $L''_1$ and $L''_3$, $L''_1$ and L'' or $L''_5$ and $L''_7$, together are $C_3$-$C_4$alkylene, $CR_1$=$CR_2$—$CR_3$=$CR_4$, $CR_1$=$CR_2$—O, $CR_1$=$CR_2$—S, $CR_1$=$CR_2$—$NR_1$, CO—O—CO, $CONR_1CO$, CO-(o-phenylene)-S, CO-(o-phenylene)-S substituted by one or more D, or are $C_1$-$C_3$alkylene interrupted by O, S, $NR_1$ or $NCOR_1$;

or for example one or more of the pairs $L_3$ and $L_5$, $L'_3$ and $L'_5$ or $L''_3$ and $L''_5$ together are a single bond, $CR_aR_b$, CO, O or S.

In particular $L_5$, $L'_5$, $L''_5$, $L_6$, $L'_6$, $L''_6$, $L_7$, $L'_7$, $L''_7$, $L_8$, $L'_8$ and $L''_8$ independently of one another are hydrogen, $R_1$ or $OR_1$; and/or one or more of the pairs $L_3$ and $L_5$, $L'_3$ and $L'_5$ or $L''_3$ and $L''_5$ together are a single bond, $CR_aR_b$, CO, O or S; provided that $L_3$ and $L_5$, $L'_3$ and $L'_5$, $L''_3$ and $L''_5$ together are no single bond, when the respective X, X', X'' denotes a single bond; and/or one or more of the pairs $L_1$ and $L_3$, $L_1$ and L, $L_5$ and $L_7$, $L'_1$ and $L'_3$, $L'_1$ and L', $L'_5$ and $L'_7$, $L''_1$ and $L''_3$, $L''_1$ and L'' or $L''_5$ and $L''_7$, together are $C_3$-$C_4$alkylene, $CR_1$=$CR_2$—$CR_3$=$CR_4$, $CR_1$=$CR_2$—O, $CR_1$=$CR_2$—S, $CR_1$=$CR_2$—$NR_1$, CO—O—CO, $CONR_1CO$, CO-(o-phenylene)-S or CO-(o-phenylene)-S substituted by one or more D;

provided that at least one of L, L', L'', $L_1$, $L'_1$, $L''_1$, $L_2$, $L'_2$, $L''_2$, $L_3$, $L'_3$, $L''_3$, $L_4$, $L'_4$, $L''_4$, $L_5$, $L'_5$, $L''_5$, $L_6$, $L'_6$, $L''_6$, $L_7$, $L'_7$, $L''_7$, $L_8$, $L'_8$, $L''_8$ is other than hydrogen;

or for example provided that at least one of L, L', L'', $L_1$, $L'_1$, $L''_1$, $L_2$, $L'_2$, $L''_2$, $L_3$, $L'_3$, $L''_3$, $L_4$, $L'_4$, $L''_4$ is $SO_3H$, $SO_3M$, $SO_2R_1$, CN, $NO_2$ or COT, in particular $NO_2$ or COT.

Preferably $L_5$, $L_6$, $L_7$ and $L_8$ independently of one another are hydrogen, $R_1$ or $OR_1$, in particular hydrogen, provided that at least one of L, $L_1$, $L_2$, $L_3$, $L_4$ is $NO_2$ or COT, in particular COT.

In particular preferred L is COT; and $L_1$, $L_2$, $L_3$, $L_4$, $L_5$, $L_6$, $L_7$ and $L_8$ are hydrogen.

D is for example hydrogen, $R_5$, $OR_5$, $SR_5$, halogen, $NO_2$, CN, O-glycidyl, O-vinyl, O-allyl, $COR_5$, $NR_5COR_6$, $COOR_5$, $OCOR_5$, $CONR_5R_6$, $OCOOR_5$, $OCONR_5R_6$, $NR_5COOR_6$, $SO_3H$ or $SO_3M$; especially D is hydrogen, $R_5$, $OR_5$, $SR_5$, halogen, $NO_2$, CN, O-glycidyl, O-vinyl, O-allyl, $COR_5$, $COOR_5$ or $OCOR_5$; and preferably D is hydrogen, $R_5$, $OR_5$, halogen, O-glycidyl, O-vinyl, O-allyl, $COR_5$, $COOR_5$ or $OCOR_5$.

E is for example O, S, COO, OCO, CO, $NCOR_5$, $NR_5CO$, $CONR_5$, OCOO, $OCONR_5$, $NR_5COO$, $SO_2$ or SO, $CR_5$=$CR_6$; or E is O, S, COO, OCO, CO, $SO_2$, SO or $CR_5$=$CR_6$; especially E is O, S, COO, OCO, CO or $CR_5$=$CR_6$; in particular E is O, COO, OCO or CO.

$T_1$ and $T_2$ for example independently of one another are hydrogen, $C_1$-$C_{20}$alkyl, $C_5$-$C_{12}$cycloalkyl, $C_2$-$C_{20}$alkenyl, $C_6$-$C_{14}$aryl, $C_1$-$C_{20}$alkyl substituted by one or more D, $C_2$-$C_{20}$alkyl interrupted by one or more E, $C_2$-$C_{20}$alkyl substituted by one or more D and interrupted by one or more E, $C_5$-$C_{12}$cycloalkyl substituted by one or more D, $C_2$-$C_{12}$cycloalkyl interrupted by one or more E, $C_2$-$C_{12}$cycloalkyl substituted by one or more D and interrupted by one or more E, $C_2$-$C_{20}$alkenyl substituted by one or more D, $C_3$-$C_{20}$alkenyl interrupted by one or more E, $C_3$-$C_{20}$alkenyl substituted by one or more D and interrupted by one or more E, or $C_6$-$C_{14}$aryl substituted by one or more D.

$T_1$ especially is hydrogen, $C_1$-$C_{20}$alkyl, $C_5$-$C_{12}$cycloalkyl, $C_6$-$C_{14}$aryl or $C_6$-$C_{14}$aryl substituted by one or more $C_1$-$C_4$alkyl, halogen or $C_1$-$C_4$alkoxy.

$T_2$ is for example hydrogen, $C_1$-$C_{20}$alkyl, $C_5$-$C_{12}$cycloalkyl, $C_6$-$C_{14}$aryl, $C_1$-$C_{20}$alkyl substituted by one or more D, $C_2$-$C_{20}$alkyl interrupted by one or more E, $C_2$-$C_{20}$alkyl substituted by one or more D and interrupted by one or more E, $C_5$-$C_{12}$cycloalkyl substituted by one or more D, $C_2$-$C_{12}$cycloalkyl interrupted by one or more E, $C_2$-$C_{12}$cycloalkyl substituted by one or more D and interrupted by one or more E, or $C_6$-$C_{14}$aryl substituted by one or more D; preferably $T_2$ is hydrogen, $C_1$-$C_{20}$alkyl, $C_5$-$C_{12}$cycloalkyl, $C_6$-$C_{14}$aryl, $C_1$-$C_{20}$alkyl substituted by one or more O-glycidyl, O-vinyl, O-allyl, $R_5$, $OR_5$, $COOR_5$ and/or optionally interrupted by one or more O, $C_2$-$C_{12}$cycloalkyl interrupted by one or more O, or is $C_6$-$C_{14}$aryl substituted by one or more $C_1$-$C_4$alkyl, halogen or $C_1$-$C_4$alkoxy; In particular $T_2$ is hydrogen, $C_1$-$C_{20}$alkyl, or is $C_1$-$C_{20}$alkyl substituted by one or more $R_5$, $OR_5$ or $COOR_5$ and/or optionally interrupted by one or more 0; especially preferred is $T_2$ as hydrogen, $C_1$-$C_{20}$alkyl, or is $C_1$-$C_{20}$alkyl substituted by one or more $OR_5$, $COOR_5$ and/or optionally interrupted by one or more O.

X, X' and X'' for example independently of one another are a single bond, $CR_aR_b$, O, S, $NR_c$ or $NCOR_c$; especially O, S, $NR_c$ or $NCOR_c$, preferably for example O, S, $NCOR_c$ or O or S, in particular O.

$R_1$, $R_2$, $R_3$, $R_4$, $R_a$, $R_b$ and $R_c$ for example independently of one another have one of the meanings given for $T_1$ above, including the corresponding preferences or for example independently of one another are hydrogen, $C_1$-$C_{12}$alkyl or phenyl.

In particular preferred are compounds of the formula I, wherein $L_1$, $L_2$, $L_3$, $L_4$, $L_5$, $L_6$, $L_7$ and $L_8$ are hydrogen L is COT, $COR_1$ or CN;

T is $C_1$-$C_{20}$alkyl or $C_6$-$C_{14}$aryl;

$R_1$ is $C_1$-$C_{20}$alkyl;

X is O or S;

Y is halogen or a non-nucleophilic anion, $C_fF_{2f+1}SO_3^-$, $C_1$-$C_{20}$-perfluoroalkylsulphonylmethide, $(BF_4)^-$, $(SbF_6)^-$, $(AsF_6)^-$, $(PF_6)^-$ and $(B(C_6F_5)_4)^-$; and f is an integer from 1 to 8.

The compounds according to the present invention can for example be prepared by reacting a compound of the formula II with a thionylhalogenide, especially thionylchloride in the presence of a Friedel-Crafts catalyst:

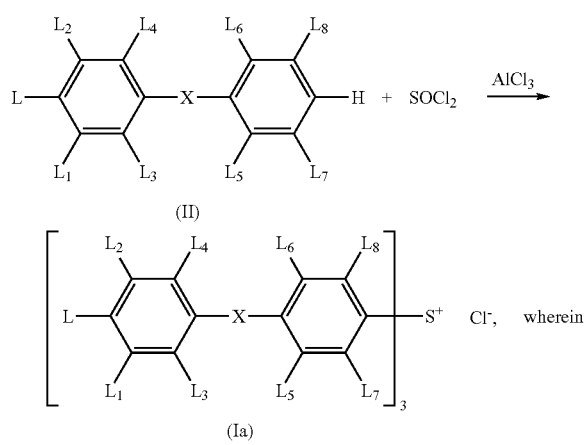

L, L$_1$, L$_2$, L$_3$, L$_4$, L$_5$, L$_6$, L$_7$, L$_8$ and X are as defined above. Mixtures of different starting compounds of formula II can be used, preferably only one kind of starting compound of formula II is used to get a tris-symmetrical product.

The reaction suitably is carried out in the presence of a Friedel-Crafts catalyst. Friedel-Crafts catalysts can be Lewis acids and/or strong Bronsted acids. Such catalysts are known to the person skilled in the art and published in textbooks of chemistry. The catalysts used for Friedel-Crafts reactions for example are described in George A. Olah, *Friedel-Crafts and Related Reactions, Vol. I*, 201 and 284-90 (1963). Aluminium trihalides such as AlBr$_3$ and AlCl$_3$ are particularly suitable, especially AlCl$_3$.

Other examples are SnCl$_4$, ZnCl$_2$, FeCl$_3$, HPF$_6$; rare earth metal trifluormethanesulfonates (published in *Bulletin of the Chemical Society of Japan*, 2000, 73(10), 2325); copper trifluormethanesulfonates (known from *Tetrahedron*, 2001, 57, 241); uranyl salts (disclosed in *Journal of Molecular Catalysis A: Chemical*, 2000, 164(1-2), 195). The use of HF is described in *Journal of Organic Chemistry*, 1991, 56(20), 5955, while in *Journal of Organic Chemistry*, 1996, 61(26), 9546 alumina/trifluoroacetic anhydride is employed under microwave conditions. ZnCl$_2$ as catalyst is known from *Indian Journal of Heterocyclic Chemistry*, 2002, 11, 229.

Zeolite catalysts in Friedel Crafts reactions are for example disclosed *J. Molecular Catalysis: Chemical* 1998, 134, 121, *Applied Catalysis A: General*, 2000, 201, 159, while the use of clays or exchanged clays is known from U.S. Pat. No. 4,304,941.

The application of heteropoly acids or heteropoly acid-containing solid supports is for example described in *Journal of Molecular Catalysis A: Chemical* 2004, 209(1-2), 189. Mixtures of Friedel-Crafts catalysts can be used and mixtures of Friedel-Crafts catalysts with salts like MY or more specifically MPF$_6$ or more interestingly with NaPF$_6$ or KPF$_6$ can be used.

Suitably the mol ratio of the compound of formula II to the Friedel-Crafts catalyst in the above reaction is for example from 100:1 to 1:5; 100:1 to 1:1; 10:1 to 1:1; oris 10:1, 5:1, 3:1, 2:1, 1:1, 1:2, 1:3, 1:5, preferably from 10:1 to 1:1.

Sulphination reactions are for example disclosed by S. Smiles and R. Le Rossignol in *JCS* 89 (1906), 696-708 and *JCS* 93 (1908), 745-762.

The preparation process conveniently is carried out in a solvent. However it is also possible, for example, to use the aromatic hydrocarbon of formula II itself, when liquid, as solvent, in which case it is used in excess. It will be readily understood that the process can also be carried out in inert solvents. Suitable solvents are, for example, the solvents described in George A. Olah, Friedel-Crafts and Related Reactions, Vol. I, 298-302 (1963). The choice of the respective solvent depends on the solubility of the educts and catalysts. Typical examples of solvents which may be used in the process are halogenated hydrocarbons such as chlorobenzene, dichlorobenzene, carbon tetrachloride, dichloromethane, tetrachloroethylene, bromobenzene, aromatic hydrocarbon derivatives such as nitrobenzene, dinitrobenzene, benzene and toluene, saturated aliphatic hydrocarbons such as pentane, hexane, heptane and the mixtures of isomers thereof, petroleum ether or cyclohexane, or further solvents, typically carbon disulfide, nitroalkanes such as nitromethane, diethyl ether, dimethyl sulfoxide or tetramethylene sulfone.

Dichloromethane, chlorobenzene and dichlorobenzene are preferred solvents.

The process is generally carried out by mixing the educt compound of formula II with the thionylchloride and reacting said educts in a suitable vessel, which is optionally provided with a heating means. The reaction optionally is carried out under inert conditions, i.e. the vessel should be equipped with appropriate means to create said atmosphere by for example working in an atmosphere of nitrogen. Other inert gases, as for example Ar or He, could also be employed. The person skilled in the art is familiar with these facts.

The reaction of the compound of the formula II with the thionylchloride can be carried out in different manner. Representative, but not exclusive examples are given below.

a) the compound of formula II is placed, together with the catalyst and the thionylchloride, in the reaction vessel and is immediately heated to the final reaction temperature, or b) the compound of formula II, together with the catalyst and the thionylchloride, is placed in the reaction vessel and heated slowly during the reaction to the final temperature, or c) the thionylchloride is added during the reaction, to the compound of formula II and the catalyst which have been previously heated to the reaction temperature, d) the catalyst is suspended in a minimum amount of either one or both of the starting materials and then the reactants are added subsequently in any order or are added together.

The reaction vessel also may for example consist of a column that is filled with the catalyst and the thionylchloride and the compound of formula II are pumped (e.g. continuously) over the catalyst through the column.

A further possibility is to bring the reactants together via a reactive distillation, which is a process in which a catalytic chemical reaction and distillation occur simultaneously in a single apparatus.

The mol ratio of the compound of formula II to the thionylhalogenide in the above reaction is for example from 10:1 to 1:1; 10:1 to 1:2; or is 10:1, 5:1, 4:1, 3.5:1, 3:2, 3:1, 1:1 or 1:2, preferably 3:1.

The reaction temperatures in principle depent on the boiling point of the educts and solvents that are employed in the reaction. Said temperature is conveniently in the range from –20° C. to about 200° C., for example from 0° C. to 140° C. or from 0° C. to 100° C., in particular from 0° C. to 80° C., preferably from 20° C. to 80° C., most preferably from 20 to 60° C.

To prepare compounds of the formula I, wherein Y is other than e.g. Cl, the chloride compound is reacted to the compound with the wanted anion by a conventional ion exchange reaction, known to the person skilled in the art. The anion Y may be already present during the Friedel-Crafts reaction.

To achieve asymmetrical compounds, i.e. compounds, wherein the meanings of for example L and L' are not the same a mixture of the corresponding educts is employed. In particular, a mixture of compounds of the formula II with II', or a mixture of compounds of the formula II with compounds of the formula II' and II":

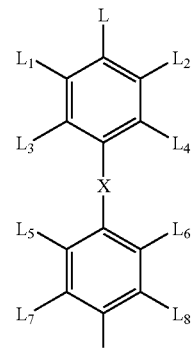

(II)

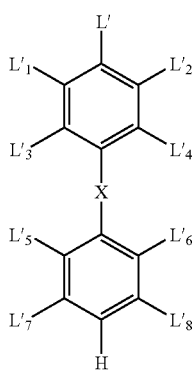

(II')

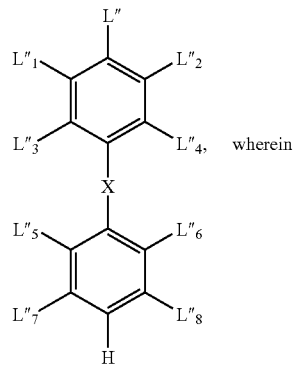

(II")

L, L', L", $L_1$, $L'_1$, $L"_1$, $L_2$, $L'_2$, $L"_2$, $L_3$, $L'_3$, $L"_3$, $L_4$, $L'_4$, $L"_4$, $L_5$, $L'_5$, $L"_5$, $L_6$, $L'_6$, $L"_6$, $L_7$, $L'_7$, $L"_7$, $L_8$, $L'_8$, $L"_8$, X, X' and X" are as defined above, is employed.

It is of course also possible to synthesize the compounds of formula I via a stepwise synthesis through a diaryl-sulfoxide intermediate (synthesis of diarylsulphoxides from arenes and thionylchloride: Oae and Zalut, *J. Am. Chem. Soc.* 82, 5359 (1960), synthesis of diarylsulphoxides from diarylsulfides via oxidation: Drabowicz and Mikolajczyk, *Org. Prep. Proced. Int.* 14, 45-89 (1982)), which is then further reacted under the following conditions with a third compound of formula (II') to get a compound of formula (I). Again, the anion can then be exchanged optionally to an anion Y:

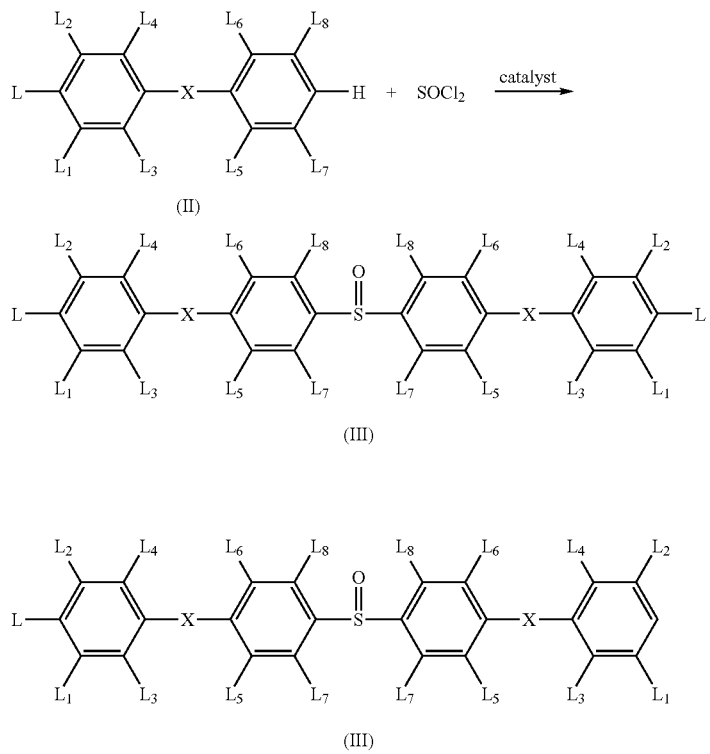

-continued

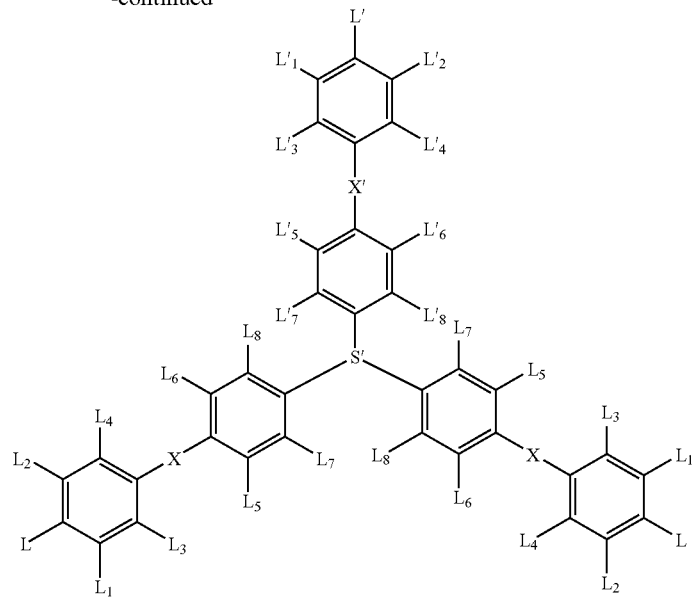

In such a stepwise reaction, three different compounds of formula (II) can be used, or two identical compounds or all identical compounds, The introduction of the third compound of formula (II) (II') or (II") in the reaction scheme depicted above can be done in a strongly acidic medium, followed my metathesis with a salt of the desired anion. Several strong acids are available as solvents, for example, sulfuric acid, polyphosphoric acid, methanesulfonic acid, or gaseous hydrogen chloride (U.S. Pat. No. 3,488,378). Mixtures of methanesulfonic acid and phosphorus pentoxide (J. Org. Chem. 1990, 55, 4222), or acetic anhydride and sulphuric acid, or methanesulfonic anhydride are also known. Typical conditions for these methods are temperatures between −50 and +100° C. Higher temperatures are usually not useful, because of secondary reactions, such as, for example, sulfonation of one aromatic ring. Lewis acids, such as aluminum chloride in terachloroethylene (WO 03/008404) can also be used. Usually, the sulfonium salt obtained by these methods has as counteranion the anion derived from one of the acids, for instance, a hydrogenosulfate, methanesulfonate, or trifluoromethanesulfonate.

Conditions without metathesis, such as arylation in acetic acid/acetic anhydride/sulfuric acid in the presence of potassium hexafluorophosphate or aqueous 75% HPF$_6$ are described for example in US 2004/0030158-A.

The starting compounds of formula (II) are for example synthesized e.g. by Friedel-Crafts (FC) reactions:

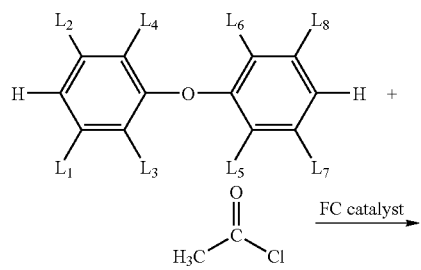

-continued

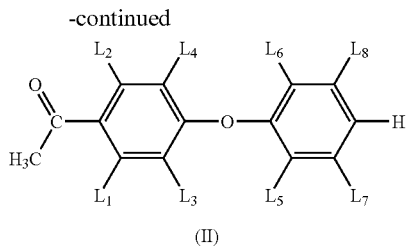

or for example by substitution reactions, where Hal is a leaving group, e.g. F, Cl, Br, I or triflate, preferably Cl or Br:

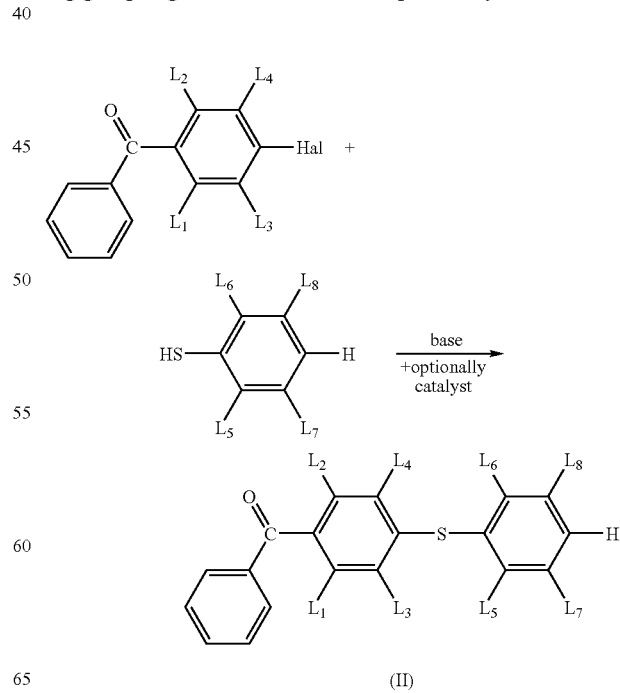

Other synthesis routes may be used in analogy to the manufacturing processes of [6317-73-3], [6317-78-8], [10169-55-8], [5031-78-7] described in the literature.

The compounds of the formula I are used as photolatent acids, i.e compounds that upon irradiation release an acid.

Accordingly, an object of the invention is a radiation-sensitive composition comprising
(a1) a cationically or acid-catalytically polymerisable or crosslinkable compound or
(a2) a compound that increases its solubility in a developer under the action of acid; and
(b) at least one compound of the formula I as described above.

The compositions according to the invention comprise as component (a1), for example, resins and compounds that can be cationically polymerised by alkyl- or aryl-containing cations or by protons. Examples thereof include cyclic ethers, especially epoxides and oxetanes, and also vinyl ethers and hydroxy-containing compounds. Lactone compounds and cyclic thioethers as well as vinyl thioethers can also be used. Further examples include aminoplastics or phenolic resole resins. These are especially melamine, urea, epoxy, phenolic, acrylic, polyester and alkyd resins, but especially mixtures of acrylic, polyester or alkyd resins with a melamine resin. These include also modified surface-coating resins, such as, for example, acrylic-modified polyester and alkyd resins. Examples of individual types of resins that are included under the terms acrylic, polyester and alkyd resins are described, for example, in Wagner, Sarx/Lackkunstharze (Munich, 1971), pages 86 to 123 and 229 to 238, or in U11-mann/Encyclopädie der techn. Chemie, 4$^{th}$ edition, volume 15 (1978), pages 613 to 628, or Ullmann's Encyclopedia of Industrial Chemistry, Verlag Chemie, 1991, Vol. 18, 360 ff., Vol. A19, 371 ff. The surface-coating preferably comprises an amino resin. Examples thereof include etherified and non-etherified melamine, urea, guanidine and biuret resins. Of special importance is acid catalysis for the curing of surface-coatings comprising etherified amino resins, such as, for example, methylated or butylated melamine resins (N-methoxymethyl- or N-butoxymethyl-melamine) or methylated/butylated glycolurils.

It is possible, for example, to use all customary epoxides, such as aromatic, aliphatic or cycloaliphatic epoxy resins. These are compounds having at least one, preferably at least two, epoxy group(s) in the molecule. Examples thereof are the glycidyl ethers and β-methyl glycidyl ethers of aliphatic or cycloaliphatic diols or polyols, e.g. those of ethylene glycol, propane-1,2-diol, propane-1,3-diol, butane-1,4-diol, diethylene glycol, polyethylene glycol, polypropylene glycol, glycerol, trimethylolpropane or 1,4-dimethylolcyclohexane or of 2,2-bis(4-hydroxycyclohexyl)propane and N,N-bis (2-hydroxyethyl)aniline; the glycidyl ethers of di- and polyphenols, for example of resorcinol, of 4,4'-dihydroxyphenyl-2,2-propane, of novolaks or of 1,1,2,2-tetrakis(4-hydroxyphenyl)ethane. Examples thereof include phenyl glycidyl ether, p-tert-butyl glycidyl ether, o-icresyl glycidyl ether, polytetrahydrofuran glycidyl ether, n-butyl glycidyl ether, 2-ethylhexylglycidylether, $C_{12/15}$alkyl glycidyl ether and cyclohexanedimethanol diglycidyl ether. Further examples include N-glycidyl compounds, for example the glycidyl compounds of ethyleneurea, 1,3-propyleneurea or 5-dimethyl-hydantoin or of 4,4'-methylene-5,5'-tetramethyldihydantoin, or compounds such as triglycidyl isocyanurate.

Further examples of glycidyl ether components (a1) that are used in the formulations according to the invention are, for example, glycidyl ethers of polyhydric phenols obtained by the reaction of polyhydric phenols with an excess of chlorohydrin, such as, for example, epichlorohydrin (e.g. glycidyl ethers of 2,2-bis(2,3-epoxypropoxyphenol)propane. Further examples of glycidyl ether epoxides that can be used in connection with the present invention are described, for example, in U.S. Pat. No. 3,018,262 and in "Handbook of Epoxy Resins" by Lee and Neville, McGraw-Hill Book Co., N.Y. (1967).

There is also a large number of commercially available glycidyl ether epoxides that are suitable as component (a1), such as, for example, glycidyl methacrylate, diglycidyl ethers of bisphenol A, for example those obtainable under the trade names EPON 828, EPON 825, EPON 1004 and EPON 1010 (Shell); DER-331, DER-332 and DER-334 (Dow Chemical); 1,4-butanediol diglycidyl ethers of phenolformaldehyde novolak, e.g. DEN-431, DEN-438 (Dow Chemical); and resorcinol diglycidyl ethers; alkyl glycidyl ethers, such as, for example, $C_8$-$C_{10}$glycidyl ethers, e.g. HELOXY Modifier 7, $C_{12}$-$C_{14}$glycidyl ethers, e.g. HELOXY Modifier 8, butyl glycidyl ethers, e.g. HELOXY Modifier 61, cresyl glycidyl ethers, e.g. HELOXY Modifier 62, p-tert-butylphenyl glycidyl ethers, e.g. HELOXY Modifier 65, polyfunctional glycidyl ethers, such as diglycidyl ethers of 1,4-butanediol, e.g. HELOXY Modifier 67, diglycidyl ethers of neopentyl glycol, e.g. HELOXY Modifier 68, diglycidyl ethers of cyclohexanedimethanol, e.g. HELOXY Modifier 107, trimethylolethane triglycidyl ethers, e.g. HELOXY Modifier 44, trimethylolpropane triglycidyl ethers, e.g. HELOXY Modifier 48, polyglycidyl ethers of aliphatic polyols, e.g. HELOXY Modifier 84 (all HELOXY glycidyl ethers are obtainable from Shell).

Also suitable are glycidyl ethers that comprise copolymers of acrylic esters, such as, for example, styrene-glycidyl methacrylate or methyl methacrylate-glycidyl acrylate. Examples thereof include 1:1 styrene/glycidyl methacrylate, 1:1 methyl methacrylate/glycidyl acrylate, 62.5:24:13.5 methyl methacrylate/ethyl acrylate/glycidyl methacrylate.

The polymers of the glycidyl ether compounds can, for example, also comprise other functionalities provided that these do not impair the cationic curing.

Other glycidyl ether compounds suitable as component (a1) that are commercially available are polyfunctional liquid and solid novolak glycidyl ether resins, e.g. PY 307, EPN 1179, EPN 1180, EPN 1182 and ECN 9699.

It will be understood that mixtures of different glycidyl ether compounds may also be used as component (a1).

The glycidyl ethers (a1) are, for example, compounds of formula XX

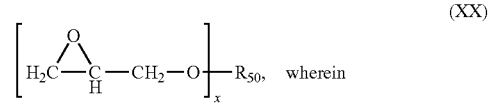

x is a number from 1 to 6; and
$R_{50}$ is a mono- to hexavalent alkyl or aryl radical.

Preference is given, for example, to glycidyl ether compounds of formula XX, wherein
x is the number 1, 2 or 3; and
$R_{50}$ when x=1, is unsubstituted or $C_1$-$C_{12}$alkyl-substituted phenyl, naphthyl, anthracyl, biphenylyl, $C_1$-$C_{20}$alkyl, or $C_2$-$C_{20}$alkyl interrupted by one or more oxygen atoms, or
$R_{50}$ when x=2, is 1,3-phenylene, 1,4-phenylene, $C_6$-$C_{10}$cycloalkylene, unsubstituted or halo-substituted $C_1$-$C_{40}$alkylene, $C_2$-$C_{40}$alkylene interrupted by one or more oxygen atoms, or a group

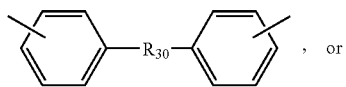, or $R_{50}$ when x=3, is a radical

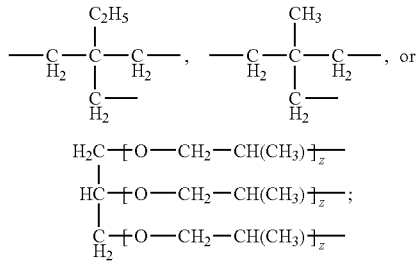

z is a number from 1 to 10; and
$R_{60}$ is $C_1$-$C_{20}$alkylene, oxygen or

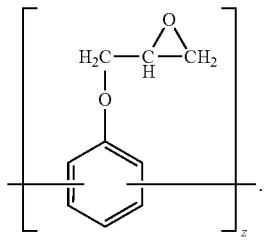

The glycidyl ethers (a1) are, for example, compounds of formula XXa

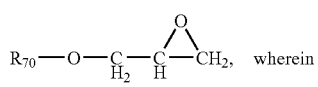 (XXa)

wherein $R_{70}$ is unsubstituted or $C_1$-$C_{12}$alkyl-substituted phenyl; naphthyl; anthracyl; biphenylyl;

$C_1$-$C_{20}$alkyl, $C_2$-$C_{20}$alkyl interrupted by one or more oxygen atoms; or a group of formula

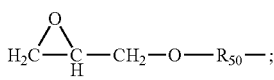

$R_{50}$ is phenylene, $C_1$-$C_{20}$alkylene, $C_2$-$C_{20}$alkylene interrupted by one or more oxygen atoms, or a group

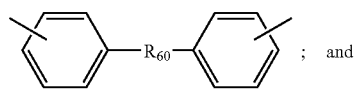; and $R_{60}$ is $C_1$-$C_{20}$alkylene or oxygen.

Preference is given to the glycidyl ether compounds of formula XXb

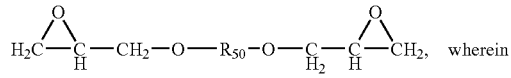 (XXb)

wherein $R_{50}$ is phenylene, $C_1$-$C_{20}$alkylene, $C_2$-$C_{20}$alkylene interrupted by one or more oxygen atoms, or a group

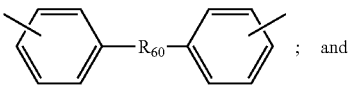; and $R_{60}$ is $C_1$-$C_{20}$alkylene or oxygen.

Further examples for component (a1) are polyglycidyl ethers and poly(β-methylglycidyl)ethers obtainable by the reaction of a compound containing at least two free alcoholic and/or phenolic hydroxy groups per molecule with the appropriate epichlorohydrin under alkaline conditions, or alternatively in the presence of an acid catalyst with subsequent alkali treatment. Mixtures of different polyols may also be used.

Such ethers can be prepared with poly(epichlorohydrin) from acyclic alcohols, such as ethylene glycol, diethylene glycol and higher poly(oxyethylene)glycols, propane-1,2-diol and poly(oxypropylene)glycols, propane-1,3-diol, butane-1,4-diol, poly(oxytetramethylene)glycols, pentane-1,5-diol, hexane-1,6-diol, hexane-2,4,6-triol, glycerol, 1,1,1-trimethylol-propane, pentaerythritol and sorbitol, from cycloaliphatic alcohols, such as resorcitol, quinitol, bis(4-hydroxycyclohexyl)methane, 2,2-bis(4-hydroxycyclohexyl)propane and 1,1-bis-(hydroxyymethyl)cyclohex-3-ene, and from alcohols having aromatic nuclei, such as N,N-bis(2-hydroxyethyl)aniline and p,p'-bis(2-hydroxyethylamino)diphenylmethane. They can also be prepared from mononuclear phenols, such as resorcinol and hydroquinone, and polynuclear phenols, such as bis(4-hydroxyphenyl)methane, 4,4-dihydroxydiphenyl, bis(4-hydroxyphenyl)sulphone, 1,1,2,2-tetrakis(4-hydroxyphenyl)ethane, 2,2-bis(4-hydroxyphenyl)-propane (bisphenol A) and 2,2-bis(3,5-dibromo-4-hydroxyphenyl)propane.

Further hydroxy compounds suitable for the preparation of polyglycidyl ethers and poly(β-methylglycidyl)ethers are the novolaks obtainable by the condensation of aldehydes, such as formaldehyde, acetaldehyde, chloral and furfural, with phenols, such as, for example, phenol, o-cresol, m-cresol, p-cresol, 3,5-dimethylphenol, 4-chlorophenol and 4-tert-butylphenol.

Poly(N-glycidyl) compounds can be obtained, for example, by dehydrochlorination of the reaction products of epichlorohydrin with amines containing at least two aminohydrogen atoms, such as aniline, n-butylamine, bis(4-aminophenyl)methane, bis(4-aminophenyl)-propane, bis(4-methylaminophenyl)methane and bis(4-aminophenyl)ether, sulphone and sulphoxide. Further suitable poly(N-glycidyl) compounds include triglycidyl isocyanurate, and N,N'-diglycidyl derivatives of cyclic alkyleneureas, such as ethyleneurea and 1,3-propyleneurea, and hydantoins, such as, for example, 5,5-dimethylhydantoin.

Poly(S-glycidyl) compounds are also suitable. Examples thereof include the di-S-glycidyl derivatives of dithiols, such as ethane-1,2-dithiol and bis(4-mercaptomethylphenyl)ether.

There also come into consideration as component (a1) epoxy resins in which the glycidyl groups or β-methyl glycidyl groups are bonded to hetero atoms of different types, for example the N,N,O-triglycidyl derivative of 4-aminophenol, the glycidyl ether/glycidyl ester of salicylic acid or p-hydroxybenzoic acid, N-glycidyl-N'-(2-glycidyloxypropyl)-5,5-dimethylhydantoin and 2-glycidyloxy-1,3-bis(5,5-dimethyl-1-glycidylhydantoin-3-yl)propane.

Preference is given to diglycidyl ethers of bisphenols. Examples thereof include diglycidyl ethers of bisphenol A, e.g. ARALDIT GY 250, diglycidyl ethers of bisphenol F and diglycidyl ethers of bisphenol S. Special preference is given to diglycidyl ethers of bisphenol A.

Further glycidyl compounds of technical importance are the glycidyl esters of carboxylic acids, especially di- and poly-carboxylic acids. Examples thereof are the glycidyl esters of succinic acid, adipic acid, azelaic acid, sebacic acid, phthalic acid, terephthalic acid, tetra- and hexa-hydrophthalic acid, isophthalic acid or trimellitic acid, or of dimerised fatty acids.

Examples of polyepoxides that are not glycidyl compounds are the epoxides of vinylcyclohexane and dicyclopentadiene, 3-(3',4'-epoxycyclohexyl)-8,9-epoxy-2,4-dioxaspiro-[5.5]undecane, the 3',4'-epoxycyclohexylmethyl esters of 3,4-epoxycyclohexanecarboxylic acid, (3,4-epoxycyclohexyl-methyl 3,4-epoxycyclohexanecarboxylate), butadiene diepoxide or isoprene diepoxide, epoxidised linoleic acid derivatives or epoxidised polybutadiene.

Further suitable epoxy compounds are, for example, limonene monoxide, epoxidised soybean oil, bisphenol-A and bisphenol-F epoxy resins, such as, for example, Araldit® GY 250 (A), ARALDIT® GY 282 (F), ARALDIT® GY 285 (F)), and photocurable siloxanes that contain epoxy groups.

Further suitable cationically polymerisable or crosslinkable components (a1) can be found, for example, also in U.S. Pat. No. 3,117,099, U.S. Pat. No. 4,299,938 and U.S. Pat. No. 4,339,567.

From the group of aliphatic epoxides there are suitable especially the monofunctional symbol α-olefin epoxides having an unbranched chain consisting of 10, 12, 14 or 16 carbon atoms.

Because nowadays a large number of different epoxy compounds are commercially available, the properties of the binder can vary widely. One possible variation, for example depending upon the intended use of the composition, is the use of mixtures of different epoxy compounds and the addition of flexibilisers and reactive diluents.

The epoxy resins can be diluted with a solvent to facilitate application, for example when application is effected by spraying, but the epoxy compound is preferably used in the solventless state. Resins that are viscous to solid at room temperature can be applied hot.

Also suitable as component (a1) are all customary vinyl ethers, such as aromatic, aliphatic or cycloaliphatic vinyl ethers and also silicon-containing vinyl ethers. These are compounds having at least one, preferably at least two, vinyl ether groups in the molecule. Examples of vinyl ethers suitable for use in the compositions according to the invention include triethylene glycol divinyl ether, 1,4-cyclohexanedimethanol divinyl ether, 4-hydroxybutyl vinyl ether, the propenyl ether of propylene carbonate, dodecyl vinyl ether, tert-butyl vinyl ether, tert-amyl ylnyl ether, cyclohexyl vinyl ether, 2-ethylhexyl vinyl ether, ethylene glycol monovinyl ether, butanediol monovinyl ether, hexanediol monovinyl ether, 1,4-cyclohexanedimethanol monovinyl ether, diethylene glycol monovinyl ether, ethylene glycol divinyl ether, ethylene glycol butylvinyl ether, butane-1,4-diol divinyl ether, hexanediol divinyl ether, diethylene glycol divinyl ether, triethylene glycol divinyl ether, triethylene glycol methylvinyl ether, tetra-ethylene glycol divinyl ether, pluriol-E-200 divinyl ether, polytetrahydrofuran divinyl ether-290, trimethylolpropane trivinyl ether, dipropylene glycol divinyl ether, octadecyl vinyl ether, (4-cyclohexylmethyleneoxyethene)-glutaric acid methyl ester and (4-butoxyethene)-isophthalic acid ester.

Examples of hydroxy-containing compounds include polyester polyols, such as, for example, polycaprolactones or polyester adipate polyols, glycols and polyether polyols, castor oil, hydroxy-functional vinyl and acrylic resins, cellulose esters, such as cellulose acetate butyrate, and phenoxy resins.

Further cationically curable formulations can be found, for example, in EP 119425.

As component (a1), preference is given to cycloaliphatic epoxides, or epoxides based on bisphenol A.

Accordingly, the invention relates also to a radiation-sensitive composition wherein component (a1) is at least one compound selected from the group of cycloaliphatic epoxy compounds, glycidyl ethers, oxetane compounds, vinyl ethers, acid-crosslinkable melamine resins, acid-crosslinkable hydroxymethylene compounds and acid-crosslinkable alkoxy-methylene compounds.

If desired, the composition according to the invention can also contain free-radically polymerisable components, such as ethylenically unsaturated monomers, oligomers or polymers. These radically polymerizable components may be added to either component (a1) or component (a2). Said radically curable components may, however, also be part of (a1) or (a2), see description of (A1), (A2) and (A3), components comprising both, radically crosslinking and cationically crosslinking groups, further below. Suitable materials contain at least one ethylenically unsaturated double bond and are capable of undergoing addition polymerisation.

Examples of suitable monomers that contain an ethylenic double bond include alkyl and hydroxyalkyl acrylates and methacrylates, such as methyl, ethyl, propyl, isopropyl, butyl, hexyl, 2-ethylhexyl and 2-hydroxyethyl (meth)acrylate, stearyl acrylate and isobornyl acrylates. Further suitable examples include acrylonitrile, acrylamide, methacrylamide, N-substituted (meth)acrylamides, vinyl esters, such as vinyl acetate, vinyl ethers, such as isobutylvinyl ether, styrene, alkyl- and halo-substituted styrene, N-vinylpyrrolidone, vinyl chloride and vinylidene chloride.

Examples of suitable monomers that contain at least two double bonds include glycerol diacrylates, glycerol triacrylates, ethylene glycol diacrylates, diethylene glycol diacrylates, diethylene glycol dimethacrylate, triethylene glycol dimethacrylates, 1,3-propanediol diacrylate, 1,3-propanediol dimethacrylate, neopentyl glycol diacrylates, hexamethylene glycol diacrylate, bisphenol-A diacrylates, 4,4'-bis(2-acryloyloxyethoxy)diphenylpropane, pentaerythritol triacrylate or tetraacrylate, pentaerythritol tetramethacrylate, trimethylolpropane triacrylate, 1,2,4-butanetriol trimethacrylate, 1,4-cyclohexanediol diacrylate, sorbitol hexaacrylate, bis[1-(2-acryloxy)]-p-ethoxyphenyldimethylmethane, bis[1-(3-acryloxy-2-hydroxy)]-p-propoxyphenyldimethylmethane and trishydroxyethyl isocyanurate trimethacrylate; the bisacrylates and bis-methacrylates of poly(ethylene glycol) having a molecular weight of from 200 to 500, diallyl phthalate, divinyl succinate, divinyl adipate and divinyl phthalate, vinyl acrylate, divinyl benzene, triallyl phosphate, triallyl isocyanurates and tris(2-acryloyl-ethyl) isocyanurate.

Examples of higher-molecular-weight (oligomeric) polyunsaturated compounds include acrylated epoxy resins, acrylated or vinyl ether- or epoxy-group-containing polyesters, polyurethanes and polyethers. Further examples of unsaturated oligomers are unsaturated polyester resins, which are usually prepared from maleic acid, phthalic acid and one or more diols and have molecular weights of approximately from 500 to 3000. Vinyl ether monomers and oligomers, and maleate-terminated oligomers having polyester, poly-urethane, polyether, polyvinyl ether and epoxy main chains can also be used. Also copolymers of vinyl ethers and monomers which are functionalised with maleic acid, as described in WO 90/01512, are also very suitable. Also suitable, however, are copolymers of monomers functionalised with vinyl ether and maleic acid. Such unsaturated oligomers can also be referred to as pre-polymers. Functionalised acrylates are also suitable. Examples of suitable monomers that are normally used to form the base polymer (the backbone) of the functionalised acrylate or methacrylate polymer are acrylate, methacrylate, methyl methacrylate, ethyl acrylate, ethyl methacrylate, n-butyl acrylate, n-butyl methacrylate, isobutyl acrylate, isobutyl methacrylate, 2-ethylhexyl acrylate, 2-ethylhexyl methacrylate, etc. In addition, suitable amounts of functional monomers are copolymerised during the polymerisation in order to obtain the functional polymers. Acid-functionalised acrylate or methacrylate polymers are obtained using acid-functional monomers, such as acrylic acid and methacrylic acid. Hydroxy-functional acrylate or methacrylate polymers are obtained from hydroxy-functional monomers, such as 2-hydroxyethyl methacrylate, 2-hydroxypropyl methacrylate and 3,4-dihydroxybutyl methacrylate. Epoxy-functionalised acrylate or methacrylate polymers are obtained using epoxy-functional monomers, such as glycidyl methacrylate, 2,3-epoxybutyl methacrylate, 3,4-epoxybutyl methacrylate, 2,3-epoxycyclohexyl methacrylate, 10,11-epoxyundecyl meth-acrylate, etc. It is also possible to obtain isocyanate-functional polymers from isocyanate-functionalised monomers, such as meta-isopropenyl-α,α-dimethyl-benzyl isocyanate.

Especially suitable are, for example, esters of ethylenically unsaturated mono- or polyfunctional carboxylic acids and polyols or polyepoxides, and polymers having ethylenically unsaturated groups in the chain or in side groups, such as unsaturated polyesters, polyamides and polyurethanes and copolymers thereof, alkyd resins, polybutadiene and butadiene copolymers, polyisoprene and isoprene copolymers, polymers and copolymers having (meth)acrylic groups in side chains, and mixtures of one or more such polymers.

Examples of suitable mono- or poly-functional unsaturated carboxylic acids are acrylic acid, methacrylic acid, crotonic acid, itaconic acid, cinnamic acid, maleic acid and fumaric acid and unsaturated fatty acids, such as linolenic acid or oleic acid. Preference is given to acrylic acid and methacrylic acid.

Mixtures of saturated di- or poly-carboxylic acids with unsaturated carboxylic acids may, however, also be used. Examples of suitable saturated di- or poly-carboxylic acids include, for example, tetrachlorophthalic acid, tetrabromophthalic acid, phthalic acid anhydride, adipic acid, tetrahydrophthalic acid, isophthalic acid, terephthalic acid, trimellitic acid, heptanedicarboxylic acid, sebacic acid, dodecanedicarboxylic acid, hexahydrophthalic acid, etc.

Suitable polyols are aromatic and especially aliphatic and cycloaliphatic polyols. Examples of aromatic polyols are hydroquinone, 4,4'-dihydroxydiphenyl, 2,2-di(4-hydroxyphenyl)-propane, and novolaks and resoles. Examples of polyepoxides are those based on the polyols mentioned, especially the aromatic polyols and epichlorohydrin. Also suitable as polyols are polymers and copolymers containing hydroxyl groups in the polymer chain or in side groups, such as polyvinyl alcohol and copolymers thereof or polymethacrylic acid hydroxyalkyl esters or copolymers thereof. Further suitable polyols are oligoesters having hydroxyl terminal groups.

Examples of aliphatic and cycloaliphatic polyols are alkylenediols having preferably from 2 to 12 carbon atoms, such as ethylene glycol, 1,2- or 1,3-propanediol, 1,2-, 1,3- or 1,4-butanediol, pentanediol, hexanediol, octanediol, dodecanediol, diethylene glycol, triethylene glycol, polyethylene glycols having molecular weights of preferably from 200 to 1500, 1,3-cyclopentanediol, 1,2-, 1,3- or 1,4-cyclohexanediol, 1,4-dihydroxymethylcyclohexane, glycerol, tris(β-hydroxyethyl)amine, trimethylolethane, trimethylolpropane, pentaerythritol, dipentaerythritol and sorbitol.

The polyols may be partially or fully esterified by one or by different unsaturated carboxylic acid(s), it being possible for the free hydroxyl groups in partial esters to have been modified, for example etherified, or esterified by other carboxylic acids.

Examples of esters are:
trimethylolpropane triacrylate, trimethylolethane triacrylate, trimethylolpropane trimethacrylate, trimethylolethane trimethacrylate, tetramethylene glycol dimethacrylate, triethylene glycol dimethacrylate, tetraethylene glycol diacrylate, pentaerythritol diacrylate, penta-erythritol triacrylate, pentaerythritol tetraacrylate, dipentaerythritol diacrylate, dipenta-erythritol triacrylate, dipentaerythritol tetraacrylate, dipentaerythritol pentaacrylate, dipenta-erythritol hexaacrylate, tripentaerythritol octaacrylate, pentaerythritol dimethacrylate, penta-erythritol trimethacrylate, dipentaerythritol dimethacrylate, dipentaerythritol tetrameth-acrylate, tripentaerythritol octamethacrylate, pentaerythritol diitaconate, dipentaerythritol trisitaconate, dipentaerythritol pentaitaconate, dipentaerythritol hexaitaconate, ethylene glycol diacrylate, 1,3-butanediol diacrylate, 1,3-butanediol dimethacrylate, 1,4-butanediol diitaconate, sorbitol triacrylate, sorbitol tetraacrylate, pentaerythritol-modified triacrylate, sorbitol tetramethacrylate, sorbitol pentaacrylate, sorbitol hexaacrylate, oligoester acrylates and methacrylates, glycerol di-and tri-acrylate, 1,4-cyclohexane diacrylate, bisacrylates and bismethacrylates of polyethylene glycol having a molecular weight of from 200 to 1500, and mixtures thereof.

Suitable unsaturated, free-radically polymerisable compounds are also the amides of the same or different unsaturated carboxylic acids and aromatic, cycloaliphatic and aliphatic polyamines having preferably from 2 to 6, especially from 2 to 4, amino groups. Examples of such polyamines are ethylenediamine, 1,2- or 1,3-propylenediamine, 1,2-, 1,3- or 1,4-butylenediamine, 1,5-pentylenediamine, 1,6-hexylenediamine, octylenediamine, dodecylenediamine, 1,4-diaminocyclohexane, isophoronediamine, phenylenediamine, bisphenylenediamine, di-β-aminoethyl ether, diethylenetriamine, triethylenetetraamine and di(β-aminoethoxy)- or di(β-aminopropoxy)-ethane. Further suitable polyamines are polymers and copolymers which may have additional amino groups in the side chain and oligoamides having amino terminal groups. Examples of such unsaturated amides are: methylene bisacrylamide, 1,6-hexamethylene bisacrylamide, bis(methacrylamidopropoxy)ethane, β-methacrylamidoethyl methacrylate and N-[(β-hydroxyethoxy)ethyl]-acrylamide.

Suitable unsaturated polyesters and polyamides are derived, for example, from maleic acid and diols or diamines. The maleic acid may have been partially replaced by other dicarboxylic acids. They can be used together with ethylenically unsaturated comonomers, for example styrene. The polyesters and polyamides can also be derived from dicarboxylic acids and ethylenically unsaturated diols or diamines, especially from those having longer chains of, for example, from 6 to 20 carbon atoms. Examples of polyurethanes are those composed of saturated or unsaturated diisocyanates and saturated or unsaturated diols.

Polybutadiene and polyisoprene and copolymers thereof are known. Suitable comonomers include, for example, olefins, such as ethylene, propene, butene, hexene, (meth)acrylates, acrylonitrile, styrene and vinyl chloride. Polymers having (meth)acrylate groups in the side chain are also known. They may be, for example, reaction products of novolak-based epoxy resins with (meth)acrylic acid; homo- or co-polymers of vinyl alcohol or hydroxyalkyl derivatives thereof that have been esterified with (meth)acrylic acid; or homo- and co-polymers of (meth)acrylates that have been esterified with hydroxyalkyl (meth)acrylates.

It is also possible to use compounds that can be crosslinked equally both free-radically and cationically. Such compounds contain, for example, both a vinyl group and a cycloaliphatic epoxy group. Examples thereof are described in JP 2-289611-A and U.S. Pat. No. 6,048,953.

Mixtures of two or more such free-radically polymerisable materials can also be used.

Binders may also be added to the compositions according to the invention, this being especially advantageous when the photopolymerisable compounds are liquid or viscous substances. The amount of binder may be, for example, from 5 to 95% by weight, preferably from 10 to 90% by weight and especially from 40 to 90% by weight, based on total solids. The binder will be selected according to the field of use and the properties required therefor, such as developability in aqueous and organic solvent systems, adhesion to substrates and sensitivity to oxygen.

Suitable binders are, for example, polymers having a molecular weight of approximately from 2000 to 2 000 000, preferably from 5000 to 1 000 000. Examples thereof are: homo- and copolymers of acrylates and methacrylates, for example copolymers of methyl methacrylate/ethyl acrylate/methacrylic acid, poly(methacrylic acid alkyl esters), poly(acrylic acid alkyl esters); phenolic resins, cellulose derivatives, such as cellulose esters and ethers, for example cellulose acetate, cellulose acetate butyrate, methyl cellulose, ethyl cellulose; polyvinyl butyral, polyvinylformal, polyolefins, cyclised rubber, polyethers, such as poly-ethylene oxide, polypropylene oxide, polytetrahydrofuran; polystyrene, polycarbonate, poly-urethane, chlorinated polyolefins, polyvinyl chloride, copolymers of vinyl chloride/vinylidene chloride, copolymers of vinylidene chloride with acrylonitrile, methyl methacrylate and vinyl acetate, polyvinyl acetate, copoly(ethylene/vinyl acetate), polymers such as polycaprolactam and poly(hexamethyleneadipamide), polyesters such as poly(ethylene glycol terephthalate) and poly(hexamethylene glycol succinate); and polyamides.

The resins mentioned below under (C1) may also be used as free-radically curable component. Of particular interest are, for example, unsaturated acrylates having reactive functional groups. The reactive functional group may be selected, for example, from a hydroxyl, thiol, isocyanate, epoxy, anhydride, carboxyl, amino or blocked amino group. Examples of OH-group-containing unsaturated acrylates are hydroxyethyl and hydroxybutyl acrylates and also glycidyl acrylates.

The unsaturated compounds may also be used in admixture with non-photopolymerisable film-forming components. These may be, for example, polymers that can be dried physically or solutions thereof in organic solvents, such as nitrocellulose or cellulose acetobutyrate. They may alternatively be chemically or thermally curable resins, such as polyisocyanates, polyepoxides or melamine resins. Drying oils, such as linseed oil, linseed-oil-modified alkyd resins, tung oil and soybean oil, can also be present. The concomitant use of thermally curable resins is important for use in so-called hybrid systems which are photopolymerised in a first step and crosslinked by thermal aftertreatment in a second step.

Thus, the radiation-curable compositions of the present invention may also comprise:

(A1) compounds having one or more free-radically polymerisable double bonds that additionally contain at least one further functional group that is reactive in addition and/or condensation reactions (examples are given above), (A2) compounds having one or more free-radically polymerisable double bonds that additionally contain at least one further functional group that is reactive in addition and/or condensation reactions, the additional functional group being complementary to or reactive towards the additional functional group of component (A1), (A3) at least one monomeric, oligomeric and/or polymeric compound having at least one functional group that is reactive in addition and/or condensation reactions towards the functional groups of component (A1) or (A2) that are present in addition to the free-radically polymerisable double bonds.

Component (A2) in each case carries the groups complementary to or reactive towards component (A1). Different types of functional groups may also be present in a component. Component (A3) provides a component that contains further functional groups that are reactive in addition and/or condensation reactions and that are able to react with the functional groups of (A1) or (A2) that are present in addition to the free-radically polymerisable double bonds. Component (A3) contains no free-radically polymerisable double bonds.

Examples of such combinations (A1), (A2), (A3) can be found in WO 99/55785.

Examples of suitable functional groups are hydroxyl, isocyanate, epoxy, anhydride, carboxyl and blocked amino groups. Examples have been described above.

Constituents of the thermally curable component (C) are, for example, thermally curable lacquer or coating system constituents customary in the art. Component (C) accordingly may consist of a large number of constituents.

Examples of component (C) include oligomers and/or polymers derived from α,β-unsaturated acids and derivatives thereof, for example polyacrylates and polymethacrylates, polymethyl methacrylates impact-resistant-modified with butyl acrylate, polyacrylamides and polyacrylonitriles. Further examples of component (C) are urethanes, polyurethanes derived on the one hand from polyethers, polyesters and polyacrylates having free hydroxyl groups and on the other hand from aliphatic or aromatic polyisocyanates, and educts thereof. Component (C) accordingly also includes, for example, crosslinkable acrylic resins derived from substituted acrylic acid esters, for example epoxy acrylates, urethane acrylates and polyester acrylates. Alkyd resins, polyester resins and acrylate resins and modifications thereof that are crosslinked with melamine resins, urea resins, isocyanates, isocyanurates, polyisocyanates, polyisocyanurates and epoxy resins, may also be a constituent of component (C).

Component (C) is, for example, generally a film-forming binder based on a thermoplastic or thermocurable resin, especially on a thermocurable resin. Examples thereof are alkyd, acrylic, polyester, phenolic, melamine, epoxy and polyurethane resins and mixtures thereof. Examples thereof can be found, for example, in Ullmann's Encyclopedia of Industrial Chemistry, 5th Ed., Vol. A18, pp. 368-426, VCH, Weinheim 1991.

Component (C) may also be a cold-curable or hot-curable binder, in which case the addition of a curing catalyst may be advantageous. Suitable catalysts that accelerate the full cure of the binder can be found, for example, in Ullmann's Encyclopedia of Industrial Chemistry, Vol. A18, page 469, VCH Verlagsgesellschaft, Weinheim 1991.

Specific examples of binders suitable as component (C) are:

1. surface-coatings based on cold- or hot-crosslinkable alkyd, acrylate, polyester, epoxy or melamine resins or mixtures of such resins, optionally with the addition of a curing catalyst;
2. two-component polyurethane surface-coatings based on hydroxyl-group-containing acrylate, polyester or polyether resins and aliphatic or aromatic isocyanates, isocyanurates or polyisocyanates;
3. one-component polyurethane surface-coatings based on blocked isocyanates, isocyanurates or polyisocyanates, which are de-blocked during heating; it is also possible to add melamine resins as appropriate;
4. one-component polyurethane surface-coatings based on aliphatic or aromatic urethanes or polyurethanes and hydroxyl-group-containing acrylate, polyester or polyether resins;
5. one-component polyurethane surface-coatings based on aliphatic or aromatic urethane acrylates or polyurethane acrylates having free amine groups in the urethane structure and melamine resins or polyether resins, optionally with the addition of a curing catalyst;
6. two-component surface-coatings based on (poly)ketimines and aliphatic or aromatic isocyanates, isocyanurates or polyisocyanates;
7. two-component surface-coatings based on (poly)ketimines and an unsaturated acrylate resin or a polyacetoacetate resin or a methacrylamidoglycolate methyl ester;
8. two-component surface-coatings based on carboxyl- or amino-group-containing polyacrylates and polyepoxides;
9. two-component surface-coatings based on anhydride-group-containing acrylate resins and a polyhydroxy or polyamino component;
10. two-component surface-coatings based on acrylate-containing anhydrides and polyepoxides;
11. two-component surface-coatings based on (poly)oxazolines and anhydride-group-containing acrylate resins or unsaturated acrylate resins or aliphatic or aromatic isocyanates, isocyanurates or polyisocyanates;
12. two-component surface-coatings based on unsaturated polyacrylates and polymalonates;
13. thermoplastic polyacrylate surface-coatings based on thermoplastic acrylate resins or extrinsically crosslinking acrylate resins in combination with etherified melamine resins;
14. surface-coating systems based on urethane (meth)acrylate having (meth)acryloyl groups and free isocyanate groups and on one or more compounds that react with iso-cyanates, for example free or esterified polyols. Such systems have been published, for example, in EP 928800.

Blocked isocyanates that can also be used as component (C) are described, for example, in Organischer Metallschutz Entwicklung und Anwendung von Beschichtungsstoffen, pages 159-160, Vincentz Verlag, Hanover (1993). These are compounds in which the highly reactive NCO group is "blocked" by reaction with specific radicals, for example a primary alcohol, phenol, acetic acid ethyl ester, ε-caprolactam, phthalimide, imidazole, oxime or amine. The blocked isocyanate is stable in liquid systems and also in the presence of hydroxy groups. Upon heating, the blocking group (protecting group) is removed again and the NCO group is freed.

1-Component (1C) and 2-component (2C) systems may be used as component (C). Examples of such systems are described in Ullmann's Encyclopedia of Industrial Chemistry, Vol. A18, Paints and Coatings, pages 404-407, VCH Verlagsgesellschaft mbH, Weinheim (1991). It is possible to optimise the composition by specific adaptation, for example by varying the binder/crosslinking agent ratios. Such measures will be known to the person skilled in the art and are customary in coating technology.

In the curing process according to the invention, component (C) is preferably a mixture based on acrylate/melamine (and melamine derivatives), 2-component polyurethane, 1-component polyurethane, 2-component epoxy/carboxy or 1-component epoxy/carboxy. Mixtures of such systems are also possible, for example the addition of melamine (or derivatives thereof) to 1-component polyurethanes.

Component (C) is preferably a binder based on a polyacrylate with melamine or on a melamine derivative or a system based on a polyacrylate and/or polyester polyol with an unblocked polyisocyanate or polyisocyanurate.

Component (C) may also comprise monomeric and/or oligomeric compounds having ethylenically unsaturated bonds (prepolymers) that additionally contain at least one or more OH, $NH_2$, COOH, epoxy or NCO group(s) (=C1) that are capable of reaction with the binder and/or the crosslinking agent constituent of component (C). After application and thermal curing, the ethylenically unsaturated bonds are converted to a crosslinked, high molecular weight form by irradiation with UV light. Examples of such components (C) are described, for example, in the above-mentioned publication, Ullmann's Encyclopedia of Industrial Chemistry, 5th Ed., Vol. A18, pages 451-453, or by S. Urano, K. Aoki, N. Tsuboniva and R. Mizuguchi in Progress in Organic Coatings, 20 (1992), 471-486, or by H. Terashima and O. Isozaki in JOCCA 1992 (6), 222.

(C1) may, for example, also be an OH-group-containing unsaturated acrylate, for example hydroxyethyl or hydroxybutyl acrylate or a glycidyl acrylate. Component (C1) may be of any desired structure (for example it may contain units of polyester, polyacrylate, polyether, etc.), provided that it contains an ethylenically unsaturated double bond and additionally free OH, COOH, $NH_2$, epoxy or NCO groups.

(C1) may, for example, also be obtained by reacting an epoxy-functional oligomer with acrylic acid or methacrylic acid. A typical example of an OH-functional oligomer having vinylic double bonds is

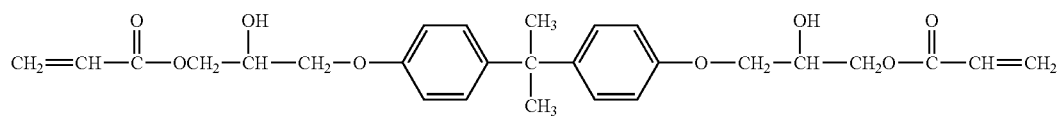

obtained by reaction of CH$_2$=CHCOOH with

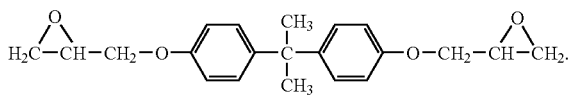

Another possible method of obtaining component (C1) is, for example, the reaction of an oligomer that contains only one epoxy group and has a free OH group at another position in the molecule.

The quantity ratio of the free-radically radiation-curable-polymerisable components to the thermally polymerisable component (C) in the UV- and thermally-crosslinkable formulations is not critical. "Dual-cure" systems are known to the person skilled in the art, who will therefore be familiar with the optimum mixing ratios of the free-radically- and thermally-crosslinkable components according to the intended use. For example, the ratio can be in the range from 5:95 to 95:5, from 20:80 to 80:20 or from 30:70 to 70:30, for example from 40:60 to 60:40.

Examples of "dual-cure" systems, that is to say systems comprising both radiation-curable and thermally curable components, can be found inter alia in U.S. Pat. No. 5,922,473, columns 6 to 10.

The formulations according to the invention can further comprise as component (a1) non-aqueous coating compositions based on an oxidatively drying alkyd resin which contains at least one, preferably two or more, functional group(s) capable of undergoing polymerisation or polycondensation reactions in the presence of an acid. Examples of such resins are vinyl-ether-functionalised alkyd resins, acetal-functionalised alkyd resins, and/or alkoxysilane-functionalised alkyd resins, as proposed, e.g., in WO 99/47617. Those modified alkyd resins may be used alone or in combination with other alkyd resins. At least some of the alkyd resin composition in the non-aqueous coating is oxidatively drying as a result of the incorporation of a large number of unsaturated, aliphatic compounds, at least some of which are polyunsaturated.

Formulations containing those modified alkyd resins as component (a1) may optionally contain, in addition to the photoinitiator (b), an oxidative dryer. Suitable oxidative dryers are, for example, metal siccatives. There may be mentioned as suitable siccatives, for example, the metal salts of (cyclo)aliphatic acids, such as octanoic acid and naphthenic acid, the metals to be used being, for example, cobalt, manganese, lead, zirconium, calcium, zinc and rare earth metals. Mixtures of siccatives may be used. Preference is given to metal salts of cobalt, zirconium and calcium, or mixtures thereof. The siccatives (calculated as metal) are usually used in an amount of from 0.001 to 3% by weight.

Under certain conditions it may also be advantageous, when using the modified alkyd resins as component (a1), to use one or more mono- or bis-acylphosphine oxide photoinitiators in addition to the sulphonium salt of formula (I). Suitable monoacyl- or bisacyl-phosphine oxide photoinitiators include, for example, monoacylphosphine oxides such as (2,4,6-trimethylbenzoyl)-diphenylphosphine oxide (DAROCUR®TPO) or (2,4,6-trimethylbenzoylphenyl-ethoxy-phosphine oxide, or bisacylphosphine oxide photoinitiators such as bis(2,6-dimethoxybenzoyl)-2,4,4-trimethylpentyl-phosphine oxide, bis(2,4,6-trimethylbenzoyl)-(2,4-dipentyloxyphenyl)-phosphine oxide and bis(2,4,6-trimethylbenzoyl)phenyl-phosphine oxide (IRGACURE®819). Those monoacyl- or bisacylphosphine oxides are advantageously used in an amount of from 0.5 to 5%.

When component (a1) contains modified alkyd resins, in addition to the photoinitiator (b) it is also possible to use an oxidative dryer and suitable monoacyl- or bisacyl-phosphine oxide photoinitiators.

The alkyd resins used as component (a1) contain a large number of unsaturated, aliphatic compounds, at least some of which are polyunsaturated. The unsaturated aliphatic compounds preferably used for the preparation of those alkyd resins are unsaturated aliphatic monocarboxylic acids, especially polyunsaturated aliphatic monocarboxylic acids.

Examples of mono-unsaturated fatty acids are myristoleic acid, palmitic acid, oleic acid, gadoleic acid, erucic acid and ricinoleic acid. Preferably fatty acids containing conjugated double bonds, such as dehydrogenated castor oil fatty acid and/or tung oil fatty acid, are used. Other suitable monocarboxylic acids include tetrahydrobenzoic acid and hydrogenated or non-hydrogenated abietic acid or the isomers thereof. If desired, the monocarboxylic acid in question may be used wholly or in part in the form of a triglyceride, e.g. as vegetable oil, in the preparation of the alkyd resin. If desired, mixtures of two or more such mono-carboxylic acids or triglycerides may be used, optionally in the presence of one or more saturated, (cyclo)aliphatic or aromatic monocarboxylic acids, e.g. pivalic acid, 2-ethyl-hexanoic acid, lauric acid, palmitic acid, stearic acid, 4-tert-butyl-benzoic acid, cyclopentanecarboxylic acid, naphthenic acid, cyclohexanecarboxylic acid, 2,4-dimethylbenzoic acid, 2-methylbenzoic acid and benzoic acid.

If desired, polycarboxylic acids may also be incorporated into the alkyd resin, such as phthalic acid, isophthalic acid, terephthalic acid, 5-tert-butylisophthalic acid, trimellitic acid, pyromellitic acid, succinic acid, adipic acid, 2,2,4-trimethyladipic acid, azelaic acid, sebacic acid, dimerised fatty acids, cyclopentane-1,2-dicarboxylic acid, cyclohexane-1,2-dicarboxylic acid, 4-methylcyclohexane-1,2-dicarboxylic acid, tetrahydrophthalic acid, endomethylenecyclohexane-1,2-dicarboxylic acid, butane-1,2,3,4-tetracarboxylic acid, endoisopropylidenecyclohexane-1,2-dicarboxylic acid, cyclohexane-1,2,4,5-tetracarboxylic acid and butane-1,2,3,4-tetracarboxylic acid. If desired, the carboxylic acid in question may be used as an anhydride or in the form of an ester, for example an ester of an alcohol having from 1 to 4 carbon atoms.

In addition, the alkyd resin can be composed of di- or poly-valent hydroxyl compounds. Examples of suitable divalent hydroxyl compounds are ethylene glycol, 1,3-propanediol, 1,6-hexanediol, 1,12-dodecanediol, 3-methyl-1,5-pentanediol, 2,2,4-trimethyl-1,6-hexane-diol, 2,2-dimethyl-1,3-propanediol and 2-methyl-2-cyclohexyl-1,3-propanediol. Examples of suitable triols are glycerol, trimethylolethane and trimethylolpropane. Suitable polyols having more than 3 hydroxyl groups are pentaerythritol, sorbitol and etherified products of the compounds in question, such as ditrimethylolpropane and di-, tri- and tetra-pentaerythritol. Preferably, compounds having from 3 to 12 carbon atoms, e.g. glycerol, pentaerythritol and/or dipentaerythritol, are used.

The alkyd resins can be obtained by direct esterification of the constituents, with the option that some of those components may already have been converted into ester diols or polyester diols. The unsaturated fatty acids can also be used in the form of a drying oil, such as linseed oil, tuna fish oil, dehydrogenated castor oil, coconut oil and dehydrogenated coconut oil. The final alkyd resin is then obtained by transesterification with the other acids and diols added. The transesterification is advantageously carried out at a temperature in the range of from 115 to 250° C., optionally in the presence of solvents such as toluene and/or xylene. The reaction is advantageously carried out in the presence of a catalytic amount of a transesterification catalyst. Examples of suitable transesterification catalysts include acids, such as p-toluenesulphonic acid, basic compounds, such as an amine, or compounds such as calcium oxide, zinc oxide, tetraisopropyl orthotitanate, dibutyltin oxide and tri-phenylbenzylphosphonium chloride.

The vinyl ether, acetal and/or alkoxysilane compounds used as part of component (a1) preferably contain at least two vinyl ether, acetal and/or alkoxysilane groups and have a molecular weight of 150 or more. Those vinyl ether, acetal and/or alkoxysilane compounds can be obtained, for example, by the reaction of a commercially available vinyl ether, acetal and/or alkoxysilane compound containing a vinyl ether, acetal and/or alkoxysilane group and in addition a maximum of one functional amino, epoxy, thiol, isocyanate, acrylic, hydride or hydroxyl group, with a compound having at least two groups capable of reacting with an amino, epoxy, thiol, isocyanate, acrylic, hydride or hydroxyl group. As examples thereof there may be mentioned compounds having at least two epoxy, isocyanate, hydroxyl and/or ester groups or compounds having at least two ethylenically or ethynylenically unsaturated groups. As component (a1), preference is given to a composition in which the vinyl ether, acetal and/or alkoxysilane compounds are covalently bonded to the alkyd resin by addition via a reactive group such as an amino, hydroxyl, thiol, hydride, epoxy and/or isocyanate group. For that purpose, the compounds must have at least one group capable of forming an adduct with the reactive groups present in the alkyd resin.

To incorporate vinyl ether groups into the alkyd resin, use is made of a vinyloxyalkyl compound, the alkyl group of which is substituted by a reactive group, such as a hydroxyl, amino, epoxy or isocyanate group, that is capable of forming an adduct with one or more of the reactive groups present in the alkyd resin.

As component (a1), preference is given to compositions in which the ratio of the number of oxidatively drying groups present in the alkyd resin to the number of groups that are reactive in the presence of an acid is in the range of from 1/10 to 15/1, especially from 1/3 to 5/1. Instead of a single modified alkyd resin, it is also possible to use a plurality of alkyd resins, with one alkyd resin being highly modified and the others being less modified or not modified at all.

Examples of vinyl ether compounds capable of being covalently bonded to the alkyd resin are ethylene glycol monovinyl ether, butanediol monovinyl ether, hexanediol monovinyl ether, triethylene glycol monovinyl ether, cyclohexanedimethanol monovinyl ether, 2-ethylhexanediol monovinyl ether, polytetrahydrofuran monovinyl ether, tetraethylene glycol monovinyl ether, trimethylolpropane divinyl ether and aminopropyl vinyl ether.

Adducts can be formed, for example, by reacting the vinyl ether compounds containing a hydroxyl group or amino group with an excess of a diisocyanate, followed by the reaction of that free-isocyanate-group-containing adduct with the free hydroxyl groups of the alkyd resin. Preferably, a process is used in which first the free hydroxyl groups of the alkyd resin react with an excess of a polyisocyanate, and then the free isocyanate groups react with an amino-group- or hydroxyl-group-containing vinyl ether compound. Instead of a diisocyanate, it is also possible to use a diester. Transesterification of the hydroxyl groups present in the alkyd resin with an excess of the diester, followed by transesterification or transamidation of the remaining ester groups with hydroxy-functional vinyl ether compounds or amino-functional vinyl ether compounds, respectively, yields vinyl-ether-functional alkyd resins. It is also possible to incorporate (meth)acrylate groups into the alkyd resin during preparation of the alkyd resin, by carrying out the preparation in the presence of a hydroxy-functional (meth)acrylate ester, such as hydroxyethyl methacrylate (HEMA), and then reacting the thus functionalised alkyd resin by means of a Michael reaction with a vinyl-ether-group-containing compound and a primary-amino-group-containing compound, followed by reaction with e.g. an isocyanate compound, in order to obtain a non-basic nitrogen atom.

An example of such a reaction is described, for example, in WO 99/47617. Esterification of ricinine fatty acid with dipentaerythritol, followed by transesterification of the free hydroxyl groups with diethyl malonate and 4-hydroxybutyl vinyl ether in a suitable ratio, yields a vinyl-ether-functional alkyd resin suitable for use as component (a1).

For the preparation of acetal-functional alkyd resins, use is generally made of dialkyl acetal functionalised with an amino group. Examples of suitable acetal compounds include 4-aminobutyraldehyde dimethyl acetal and 4-aminobutyraldehyde diethyl acetal. The alkyd resin is modified by the addition of the aminoacetal monomer to an alkyd resin functionalised with isocyanate groups, with ester groups of a low-boiling alcohol or with (meth)acrylate groups. The resulting dialkyl-acetal-modified alkyd resin can be incorporated into the coating composition having a high solids content and low viscosity. The preparation of acetal-functional alkyd resins can also be carried out by reacting hydroxyacetal with the carboxyl groups of the alkyd resin or by reacting a diisocyanate or diester compound with the hydroxyl groups of the alkyd resin.

An example of this preparative method is described in WO 99/47617, for example the esterification of a hydroxy-functional alkyd resin with diethyl malonate, followed by transamidation of the free ester group with 4-aminobutyraldehyde dimethyl acetal in a suitable ratio. The resulting acetal-modified alkyd resin is suitable as component (a1).

For the incorporation of alkoxysilane groups into the alkyd resin, use is made of a siloxane compound having one or more reactive group(s) which are subsequently reacted with one or more of the constituents making up the alkyd resin. These are, for example, alkoxy-silanes of the formula: $(E)_a\text{-Si}(R_{10})_b(R_{20})_c$, wherein $R_{10}$ is alkoxy or oxyalkylenealkoxy or, when E is hydrogen, $R_{10}$ is halogen, $R_{20}$ is an aliphatic, cycloaliphatic or aromatic group, and E is hydrogen or an alkyl group substituted by an amino, isocyanate, mercapto or epoxy group; a is from 1 to 3, b is from 1 to 3, c is from 0 to 2, and a+b+c=4.

$R_{10}$ is preferably an alkoxy group having from 1 to 4 carbon atoms in the alkoxy group, and $R_{20}$ is preferably a group having not more than 18 carbon atoms.

Examples of suitable siloxane compounds are 3-aminopropyl-triethoxysilane, polyglycol-ether-modified aminosilane, 3-aminopropyl-trimethoxysilane, 3-aminopropyltris-methoxy-ethoxyethoxysilane, 3-aminopropyl-methyl-diethoxysilane, N-2-aminoethyl-3-aminopropyl-trimethoxy-silane, N-2-aminoethyl-3-aminopropyl-methyldimethoxy-silane, N-methyl-3-aminopropyl-trimethoxysilane, 3-ureidopropyl-triethoxysilane, 3,4,5-dihydroimidazol-1-yl-propyltriethoxysilane, 3-methacryloxypropyl-trimethoxysilane, 3-glycidyloxypropyl-trimethoxysilane, 3-mercaptopropyltrimethoxysilane and 3-mercaptopropyl-methyl-dimethoxysilane, triethoxysilane, diethoxymethylsilane, dimethoxymethylsilane, tri-methoxysilane, trichlorosilane, triiodosilane, tribromosilane, dichloromethylsilane and dibromomethylsilane.

The alkyd resin can be modified, for example, by the insertion of an amino-group-modified alkoxysilane into an alkyd resin modified with a polyisocyanate or a polyester of a low-boiling alcohol. Hydride-functional alkoxysilanes can be bonded directly to the alkyd, i.e. without modification with a binding molecule such as a diisocyanate or diester, by adding a compound containing a silylhydride group to an ethylenically unsaturated group in the alkyd resin. That addition is catalysed by a transition metal. In that process, use is preferably made of a halogenated silylhydride and, in order to terminate the addition reaction, conversion into an alkoxysilane compound with a low-boiling alcohol. The addition reaction is advantageously carried out in the absence of sterically hindering groups and proceeds in optimum manner when the ethylenically unsaturated groups are terminal groups, as is the case, for example, with esters of 10-undecenecarboxylic acid.

Examples of the preparation of alkoxysiloxane-modified alkyd resins are described in WO 99/47617. Esterification of a hydroxy-functional alkyd resin with diethyl malonate, followed by transamidation of the free ester group with 3-aminopropyltriethoxysilane in a suitable ratio yields an alkoxysilane-modified alkyd resin. Hydroxy-modified alkyd resin can also be reacted with an excess of isophorone diisocyanate, followed by reaction of the free isocyanate groups with 3-aminopropyltriethoxysilane. Both alkoxysiloxane-modified alkyd resins obtained by the processes described are suitable for use in component (a1).

When free-radically polymerisable components are added to the formulation according to the invention, it may be advantageous to add also a suitable free-radical photoinitiator or a mixture of such photoinitiators, e.g. benzophenone and derivatives thereof, ESACURE TZT® available from Lamberti, a mixture of 2,4,6-trimethylbenzophenone and 4-methylbenzophenone, Darocur®BP, benzophenone, 4-methyl benzophenone, 2,4,6-trimethylbenzophenone, 3-methyl-4'-phenyl-benzophenone, 2,4,6-trimethyl-4'-phenyl-benzophenone, etc., acetophenone and derivatives thereof, e.g. 1-hydroxy-cyclohexyl-phenyl-ketone (IRGACURE® 184) or IRGACURE®500 (a mixture of IRGACURE®184 with benzophenone); or 2-hydroxy-2-methyl-1-phenyl-propanone (DAROCUR® 1173), 2-hydroxy-1-[3-[4-(2-hydroxy-2-methyl-propionyl)-phenyl]-1,1,3-trimethyl-indan-5-yl]-2-methyl-propan-1-one, 4-aroyl-1,3-dioxolane, α-hydroxy- or α-amino-acetophenone, such as, for example, 2-methyl-1[4-(methylthio)phenyl]-2-morpholinopropan-1-one (IRGACURE®907), 2-benzyl-2-dimethylamino-1-(4-morpholinophenyl)-butanone-1 (IRGACURE®369), 2-dimethylamino-2-(4-methyl-benzyl)-1-(4-morpholin-4-yl-phenyl)-butan-1-one(IRGACURE®379), 1-[4-(2-hydroxyethoxy)-phenyl]-2-hydroxy-2-methyl-1-propan-1-one (IRGACURE®2959), 2,2-dimethoxy-1,2-diphenylethan-1-one (IRGACURE®651), 2-hydroxy-1-{4-[4-(2-hydroxy-2-methyl-propionyl)-benzyl]-phenyl}-2-methyl-propan-1-one (IRGACURE® 127), 2-benzyl-1-(3,4-dimethoxy-phenyl)-2-dimethylamino-butan-1-one, 2-hydroxy-1-{4-[4-(2-hydroxy-2-methyl-propionyl)-phenoxy]-phenyl}-2-methyl-propan-1-one, ESACURE®KIP provided by F. Lamberti, 2-hydroxy-1-{1-[4-(2-hydroxy-2-methyl-propionyl)-phenyl]-1,3,3-trimethyl-indan-5-yl}-2-methyl-propan-1-one; benzoin alkyl ethers and benzil ketal, such as, for example, benzil dimethyl ketal, phenyl glyoxalate and derivatives thereof, e.g. oxo-phenyl-acetic acid 2-[2-(2-oxo-2-phenyl-acetoxy)-ethoxy]-ethyl ester (IRGACURE®754), mono- or bis-acylphosphine oxide, such as, for example, (2,4,6-trimethyl-benzoyl)-phenyl-phosphine oxide (DAROCUR®TPO), bis(2,6-dimethoxybenzoyl)-(2,4,4-trimethyl-pent-1-yl)phosphine oxide, bis(2,4,6-trimethylbenzoyl)-phenyl-phosphine oxide (IRGACURE®819) or bis(2,4,6-trimethylbenzoyl)-(2,4-dipentyloxyphenyl)phosphine oxide.

The DAROCUR and IRGACURE compounds are available from Ciba Specialty Chemicals.

Other additional components can be, for example, hydroxy-functional components, such as alcohols, polyester polyols, polyether polyols, hydroxy-group-containing polyurethanes, castor oil, etc. Examples thereof include aliphatic and cycloaliphatic polyols, such as alkylene diols having preferably from 2 to 12 carbon atoms, e.g. ethylene glycol, 1,2- or 1,3-propanediol, 1,2-, 1,3- or 1,4-butanediol, pentanediol, hexanediol, octanediol, dodecanediol, diethylene glycol, triethylene glycol, polyethylene glycols having molecular weights of preferably from 200 to 1500, 1,3-cyclopentanediol, 1,2-, 1,3- or 1,4-cyclohexanediol, 1,4-di-hydroxymethylcyclohexane, glycerol, tris(β-hydroxy-ethyl) amine, trimethylolethane, tri-methylolpropane, pentaerythritol, dipentaerythritol and sorbitol. The polyols can be partially or fully esterified by one or by different unsaturated carboxylic acids, it being possible for the free hydroxyl groups in partial esters to have been modified, e.g. etherified, or esterified by other carboxylic acids. Examples of esters include: trimethylolpropane triacrylate, trimethylolethane triacrylate, trimethylolpropane trimethacrylate, trimethylolethane trimeth-acrylate, tetramethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentaacrylate, dipentaerythritol hexaacrylate, tripentaerythritol octaacrylate, pentaerythritol dimethacrylate, pentaerythritol trimethacrylate, dipentaerythritol dimethacrylate, dipentaerythritol tetramethacrylate, tripentaerythritol octamethacrylate, pentaerythritol diitaconate, dipentaerythritol trisitaconate, dipentaerythritol pentaitaconate, dipentaerythritol hexaitaconate, ethylene glycol diacrylate, 1,3-butanediol diacrylate, 1,3-butanediol dimethacrylate, 1,4-butanediol diacrylate, sorbitol triacrylate, sorbitol tetraacrylate, pentaerythritol-modified triacrylate, sorbitol tetramethacrylate, sorbitol pentaacrylate, sorbitol hexaacrylate, oligoester acrylates and methacrylates, glycerol di- and tri-acrylate, 1,4-cyclohexane diacrylate, bisacrylates and bismethacrylates of polyethylene glycol having a molecular weight of from 200 to 1500, or mixtures thereof.

The sulphonium salt compounds of formula I can also be used, for example, as photoactivatable hardeners for siloxane-group-containing resins. Those resins can, for example, either undergo self-condensation by way of acid-catalysed hydrolysis or can be crosslinked with a second resin component, such as, for example, a polyfunctional alcohol, a hydroxygroup-containing acrylic or polyester resin, a partially hydrolysed polyvinylacetal or a polyvinyl alcohol. That type of polycondensation of polysiloxanes is described, for example, in J. J. Lebrun, H. Pode, Comprehensive Polymer Science Vol. 5, page 593, Pergamon Press, Oxford, 1989.

Examples of compounds whose solubility increases in a developer under the action of acid, i.e., component (a2) include oligomers, polymers and copolymers that can be obtained by co-polymerisation of, for example, the following monomers: non-cyclic or cyclic secondary and tertiary alkyl (meth)acrylates, such as tert-butyl acrylate, tert-butyl methacrylate, 3-oxocyclohexyl (meth)acrylate, tetrahydropyranyl (meth)acrylate, 2-methyl-2-adamantyl (meth)acrylate, cyclohexyl (meth)acrylate, norbornyl (meth)acrylate, isobornyl methacrylate, 5-norbornene-2-tert-butyl ester, 8-ethyl-8-tricyclodecanyl (meth)acrylate, (2-tetrahydropyranyl)oxy-norbornylalcohol acrylates, (2-tetrahydropyranyl) oxymethyltricyclododecanemethanol methacrylates, trimethylsilylmethyl (meth)acrylates, (2-tetrahydropyranyl) oxynorbornylalcohol acrylates, (2-tetrahydropyranyl) oxymethyltricyclododecanemethanol methacrylates, trimethylsilylmethyl (meth)acrylate, o-/m-/p-(3-oxocyclohexyloxy)styrene, o-/m-/p-(1-methyl-1-phenylethoxy)styrene, o-/m-/p-tetrahydropyranyloxystyrene, o-1m-1p-adamantyloxystyrene, o-/m-/p-cyclohexyloxystyrene, o-/m-/p-norbornyloxystyrene, non-cyclic or cyclic alkoxycarbonylstyrenes, such as o-/m-/p-tert-butoxycarbonylstyrene, o-1m-1p-(3-oxocyclohexyloxycarbonyl)styrene, o-/m-/p-(1-methyl-1-phenylethoxycarbonyl)styrene, o-/m/p-tetrahydropyranyloxycarbonylstyrene, o-/m-/p-adamantyloxycarbonylstyrene, o-1m-1p-cyclohexyloxycarbonylstyrene, o-/m-/p-norbornyloxycarbonylstyrene, non-cyclic or cyclic alkoxycarbonyloxystyrenes, such as o-/m-/p-tert-butoxycarbonyloxystyrene, o-1m-1p-(3-oxocyclohexyloxycarbonyloxy)styrene, o-/m-/p-(1-methyl-1-phenylethoxycarbonyloxy)styrene, o-/m-/p-tetrahydropyranyloxycarbonyloxystyrene, o-/m-/p-adamantyloxycarbonyloxystyrene, o-/m-/p-cyclohexyloxycarbonyloxystyrene, o-/m-/p-norbornyloxycarbonyloxystyrene, non-cyclic or cyclic alkoxycarbonylalkoxystyrenes, such as o-/m-/p-butoxycarbonylmethoxystyrene, p-tert-butoxycarbonylmethoxystyrene, o-/m-/p-(3-oxocyclohexyloxycarbonylmethoxy)styrene, o-/m-/p-(1-methyl-1-phenylethoxycarbonylmethoxy)styrene, o-1m-1p-tetrahydropyranyloxycarbonyl methoxystyrene, o-/m-/p-adamantyloxycarbonylmethoxystyrene, o-/m-/p-cyclohexyloxycarbonylmethoxystyrene, o-1m-1p-norbornyloxycarbonylmethoxystyrene, trimethylsiloxystyrene, dimethyl(butyl)siloxystyrene, unsaturated alkyl acetates, such as isopropenyl acetate and derivatives thereof, 5-norbornenyl-2-tert-butyl ester; also monomers that carry acid-labile groups having low activation energy, such as, for example, p- or m-(1-methoxy-1-methylethoxy)styrene, p- or m-(1-methoxy-1-methylethoxy)methylstyrene, p- or m-(1-methoxy-1-methylpropoxy)styrene, p- or m-(1-methoxy-1-methylpropoxy)methylstyrene, p- or m-(1-methoxyethoxy)styrene, p- or m-(1-methoxyethoxy)methylstyrene, p- or m-(1-ethoxy-1-methylethoxy)styrenes, p- or m-(1-ethoxy-1-methylethoxy)methylstyrene, p- or m-(1-ethoxy-1-methylpropoxy)styrene, p- or m-(1-ethoxy-1-methylpropoxy)methylstyrene, p- or m-(1-ethoxyethoxy) styrene, p- or m-(1-ethoxyethoxy)methylstyrene, p-(1-ethoxyphenylethoxy)styrene, p- or m-(1-n-propoxy-1-methylethoxy)-styrene, p- or m-(1-n-propoxy-1-methylethoxy)methylstyrene, p- or m-(1-n-propoxyethoxy) styrene, p- or m-(1-n-propoxyethoxy)methylstyrene, p- or m-(1-isopropoxy-1-methylethoxy)styrene, p- or m-(1-isopropoxy-1-methylethoxy)methylstyrene, p- or m-(1-isopropoxyethoxy)styrene, p- or m-(1-isopropoxyethoxy)methylstyrene, p- or m-(1-isopropoxy-1-methyl-propoxy)styrene, p- or m-(1-isopropoxy-1-methylpropoxy)-methylstyrene, p- or m-(1-iso-propoxypropoxy)styrene, p- or m-(1-isopropoxypropoxy)-methylstyrene, p- or m-(1-n-butoxy-1-methylethoxy)styrene, p- or m-(1-n-butoxyethoxy)styrene, p- or m-(1-isobutoxy-1-methyl-ethoxy)styrene, p- or m-(1-tert-butoxy-1-methylethoxy)styrene, p- or m-(1-n-pentyloxy-1-methylethoxy)styrene, p- or m-(1-isoamyloxy-1-methylethoxy)styrene, p- or m-(1-n-hexyloxy-1-methylethoxy) styrene, p- or m-(1-cyclohexyloxy-1-methylethoxy)styrene, p- or m-(1-trimethylsilyloxy-1-methylethoxy)styrene, p- or m-(1-trimethylsilyloxy-1-methylethoxy)-methylstyrene, p- or m-(1-benzyloxy-1-methylethoxy)styrene, p- or m-(1-benzyloxy-1-methylethoxy)methylstyrene, p- or m-(1-methoxy-1-methylethoxy)styrene, p- or m-(1-methoxy-1-methylethoxy)-methylstyrene, p- or m-(1-trimethylsilyloxy-1-methylethoxy)-styrene, p- or m-(1-trimethylsilyloxy-1-methylethoxy)methylstyrene. Further examples of polymers having alkoxyalkyl ester acid-labile groups can be found in U.S. Pat. No. 5,225,316 and EP 829766. Examples of polymers having acetal protecting groups are described, for example, in U.S. Pat. No. 5,670,299, EP 780 732, U.S. Pat. Nos. 5,627,006, 5,558,976, 5,558,971, 5,468,589, EP 704762, EP 762206, EP 342498, EP 553737 and in ACS Symp. Ser. 614, Microelectronics Technology, pp. 35-55 (1995), J. Photopolymer Sci. Technol. Vol. 10, No. 4 (1997), pp. 571-578, J. Photopolymer Sci. Technol. Vol. 12, no. 4 (1999) pp. 591-599 and in "Proceedings of SPIE", Advances in Resist Technology and Processing XVII, Vol. 3999, Part One, pp. 579-590, 28. Feb.-1. Mar. 2000. The polymers suitable in the composition according to the invention are not, however, limited thereto.

The monomers having an acid-labile group can, where appropriate, also be co-polymerised with other free-radically polymerisable monomers that do not carry acid-labile groups, such as, for example, styrene, acrylonitrile, methyl (meth) acrylate, (meth)acrylic acid, 4-hydroxystyrene, 4-acetoxystyrene, 4-methoxystyrene, 4-vinylcyclohexanol, norbornene, ethylnorbornene and maleic acid anhydride, in order to establish specific solubility properties and adhesive properties. Alternatively, the acid-labile groups can be introduced only subsequently in a polymer-analogous reaction. It is also known to the person skilled in the art that the prepolymer can be modified in targeted manner before such a polymer-analogous reaction, for example by partial hydrogenation, partial alkylation, partial acetylation. That is to say, that the polymer having acid-labile groups does not, in every case, have to be synthesised from monomers by copolymerisation.

It is also possible to introduce acid-labile crosslinking, as described, for example, in H.-T. Schacht, P. Falcigno, N. Muenzel, R. Schulz and A. Medina, ACS Symp. Ser. 706 (Micro- and Nanopatterning Polymers), pp. 78-94, 1997; H.-T. Schacht, N. Muenzel, P. Falcigno, H. Holzwarth and J. Schneider, J. Photopolymer Science and Technology, Vol. 9, (1996), 573-586. Such acid-crosslinked systems are preferred in resist applications from the standpoint of heat stability. Such acid-labile crosslinking can also be obtained by the reaction of phenol-group-containing polymers, such as, for example, 4-hydroxystyrene co-polymers, with di- and polyfunctional vinyl ethers.

Other examples of component (a2) that increase their solubility in an alkaline developer upon reaction with acid are monomeric compounds, such as, for example, carboxylic acids and phenol-group-containing compounds, in which the carboxylic acid group or phenolic OH group, respectively, has been blocked by acid-labile protecting groups. Such acid-labile blocking can be effected, for example, by conversion of the carboxyl group into a tert-butyl ester group, a 2-methyl-2-adamantyl ester group, an 8-ethyl-8-tricyclodecanyl ester group, a tetrahydropyranyl ester group or some other acid-cleavable ester group. Phenolic OH groups can be blocked according to known processes by conversion, e.g. into acid-cleavable tert-butylcarbonate groups, silyl ethers, acetal groups and ketal groups.

The invention relates also to a radiation-sensitive composition wherein component (a2) is at least one compound selected from the group of cycloaliphatic copolymers, 4-hydroxy-phenyl-group-containing copolymers, maleic acid anhydride-containing copolymers and acrylic acid-, acrylic acid ester- and methacrylic acid ester-containing copolymers, with the proviso that those copolymers carry functional groups that increase the solubility of the polymer in an alkaline developer after reaction with an acid.

In the compositions according to the invention, the photoinitiator (b) is advantageously used in an amount of from 0.05% to 15%, e.g. from 0.5% to 10%, preferably from 1% to 5%, based on the composition.

The compositions according to the invention can be used in numerous applications, for example in cationically radiation-curable printing inks, in cationically radiation-curable coating compounds which may or may not be pigmented, in cationically radiation-curable adhesives, coatings and mouldings, including glass fibre-reinforced and carbon fibre-reinforced composites and inner and outer layers of printed circuit boards.

The compositions according to the invention include also adhesives, as used, for example, for adhesive bonding (DVD bonding) in the manufacture of digital versatile disks (DVD) and as described, for example, in: WO 99/66506, WO 99/63017, JP 11241055 A2 Heisei, JP 11181391 A2 Heisei, WO 98/31765, and also as radiation-curable laminating adhesives for flexible packaging (see, e.g., U.S. Pat. No. 5,328,940), optical adhesives (e.g. German Patent Application DD 225985) and pressure-sensitive adhesives (e.g. U.S. Pat. No. 4,988,741 and EP 115870).

The compositions according to the invention are advantageously used where there is a need for hard coatings, adhesive bonds or photopolymerised dimensionally stable three-dimensional mouldings (e.g. for rapid prototyping) having good adhesion to paper, glass, metal, silicon, polycarbonate, acrylate polymers and other polymer substrates, and that exhibit only slight shrinkage during curing.

Depending on the kind of application of the compounds of formula I according to the present invention it may be advantageous to add appropriate further additives, sensitzers and/or photoinitiators. Such additives, sensitizers and photoinitiators are customary in the art and known to the person skilled in the art.

Preference therefore is also given to a composition as described above that comprises in addition to components (a1) or (a2) and (b), additional additives (c) and/or sensitiser compounds (d) and optionally further photoinitiators (e).

The photopolymerisable mixtures can comprise various additives (c) in addition to the photoinitiator. Examples thereof include thermal inhibitors, light stabilisers, optical brighteners, fillers and pigments, as well as white and coloured pigments, dyes, antistatics, adhesion promoters, wetting agents, flow auxiliaries, lubricants, waxes, anti-adhesive agents, dispersants, emulsifiers, anti-oxidants; fillers, e.g. talcum, gypsum, silicic acid, rutile, carbon black, zinc oxide, iron oxides; reaction accelerators, thickeners, matting agents, antifoams, and other adjuvants customary, for example, in lacquer and coating technology.

The formulations can also comprise dyes and/or white or coloured pigments as additional additives (c). Depending upon the intended use, it is possible to use both inorganic and organic pigments. Such additives are known to the person skilled in the art; some examples thereof are titanium dioxide pigments, for example of the rutile or anatase type, carbon black, zinc oxide, such as zinc white, iron oxides, such as iron oxide yellow, iron oxide red, chromium yellow, chromium green, nickel titanium yellow, ultramarine blue, cobalt blue, bismuth vanadate, cadmium yellow and cadmium red. Examples of organic pigments are mono- or bis-azo pigments, and metal complexes thereof, phthalocyanine pigments, polycyclic pigments, such as, for example, perylene, anthraquinone, thioindigo, quinacridone and triphenylmethane pigments, and diketo-pyrrolo-pyrrole, isoindolinone, e.g. tetrachloro-isoindolinone, isoindoline, dioxazine, benzimidazolone and quinophthalone pigments.

The pigments can be used individually or in admixture in the formulations. Depending upon the intended use, the pigments are added to the formulations in amounts customary in the art, for example in an amount of from 1 to 60% by weight, or from 10 to 30% by weight, based on the total weight.

The formulations may, for example, also comprise organic dyes of a wide variety of classes. Examples thereof include azo dyes, methine dyes, anthraquinone dyes and metal complex dyes. Customary concentrations are, for example, from 0.1 to 20%, especially from 1 to 5%, based on the total weight.

The pigments, latent pigments or dyes or differently coloured precursors of such pigments and dyes that are added may be so selected that they undergo a colour change in the presence of the acid formed from the iodonium salt as a result of irradiation. Such compositions then show, by the colour change, that they have been irradiated and can be used, for example, as irradiation dose indicators, e.g. for UV radiation, electron beams, X-rays, etc.

The choice of additives will depend upon the field of use in question and upon the properties desired for that field. The additives (c) described above are customary in the art and are accordingly used in amounts customary in the art.

The compositions according to the present invention as component (c) also may comprise a stabilizer for the compounds of the formula I, e.g. from the hindered nitroxyl or phosphite type as are for example described as stabilizers for iodonium salts in WO 05/070989.

Examples for said stabilizer compounds are organic phosphorus stabilizers as disclosed for example in U.S. Pat. No. 6,444,733, the disclosure of which is hereby incorporated by reference. Organic phosphorus stabilizers are known and many are commercially available. Other examples for said stabilizer compounds are hindered nitroxyl stabilizers, or hindered nitroxides, as are well known in the art and are disclosed for example in U.S. Pat. No. 6,337,426 and, U.S. Pat. No. 5,254,760, the relevant disclosures of which are hereby incorporated by reference. Other suitable stabilizers (c) for the sulphonium salts of the formula I are for example disclosed in WO 99/35188. Examples are tertiary and sterically hindered amines, such as the TINUVIN® products, provided by Ciba Specialty Chemicals, in particular TINUVIN® 144 and TINUVIN® 292. Other possibilities for stabilization of the cationic formulations are e.g. disclosed in EP Patent Application No. 06122783.1, the disclosure is incorporated herein by reference.

Acceleration of the photopolymerisation can also be effected by adding as further additives (d) photosensitisers that shift or broaden the spectral sensitivity. These are especially aromatic carbonyl compounds, such as, for example, benzophenone, thioxanthone, and especially also isopropylthioxanthone, phenothiazine derivatives, anthraquinone and 3-acylcoumarin derivatives, terphenyls, styryl ketones, and 3-(aroylmethylene)-thiazolines, camphorquinone, and also eosin, rhodamine and erythrosin dyes, and anthracene derivatives, such as, for example, 9-methylanthracene, 9,10-dimethylanthracene, 9,10-diethoxyanthracene, 9,10-dibutyloxyanthracene, 9-methoxyanthracene, 9-anthracenemethanol, especially 9,10-dimethoxy-2-ethyl-anthracene, 9,10-dibutyloxyanthracene and 9,10-diethoxyanthracene. Further suitable photosensitisers are mentioned, for example, in WO 98/47046. Subject of the invention also are radiation-sensitive compositions as described above, additionally to components (a1) or (a2) and (b) comprising at least one sensitizer compound (d), in particular benzophenone, thioxanthone, anthracene or derivatives thereof.

Further examples of suitable photosensitisers (d) are disclosed in WO 06/008251, page 36, line 30 to page 38, line 8, the disclosure of which is hereby incorporated by reference.

It is also possible to use electron donor compounds, such as, for example, alkyl- and arylamine donor compounds, in the composition. Such compounds are, for example, 4-dimethylaminobenzoic acid, ethyl 4-dimethylaminobenzoate, 3-dimethylaminobenzoic acid, 4-dimethylaminobenzoin, 4-dimethylaminobenzaldehyde, 4-dimethylaminobenzonitrile and 1,2,4-trimethoxybenzene. Such donor compounds are preferably used in a concentration of from 0.01 to 5%, especially in a concentration of from 0.05 to 0.50%, based on the formulation.

The sensitisers (d) described above are customary in the art and are accordingly used in amounts customary in the art, preferably in a concentration of from 0.05 to 5%, especially in a concentration of from 0.1 to 2%, based on the composition.

The compositions according to the invention may additionally comprise further photo-initiators (e), such as, for example, cationic photoinitiators, photo acid-formers and free-radical photoinitiators as co-initiators in amounts of from 0.01 to 15%, preferably from 0.1 to 5%.

Examples of cationic photoinitiators and acid-formers are phosphonium salts, diazonium salts, pyridinium salts, iodonium salts, such as for example tolylcumyliodonium tetrakis (pentafluorophenyl)borate, 4-[(2-hydroxy-tetradecyloxy) phenyl]phenyliodonium hexafluoroantimonate or hexafluorophosphate (SarCat® CD 1012; Sartomer), tolylcumyliodonium hexafluorophosphate, 4-isobutylphenyl-4'-methylphenyliodonium hexafluorophosphate (IRGACURE®250, Ciba Specialty Chemicals), 4-octyloxyphenyl-phenyliodonium hexafluorophosphate or hexafluoroantimonate, bis(dodecylphenyl)iodonium hexafluoroantimonate or hexafluorophosphate, bis(4-methylphenyl)iodonium hexafluorophosphate, bis(4-methoxyphenyl)iodonium hexafluorophosphate, 4-methylphenyl-4'-ethoxyphenyliodonium hexafluorophosphate, 4-methylphenyl-4'-dodecylphenyliodonium hexafluorophosphate, 4-methylphenyl-4'-phenoxyphenyliodonium hexafluorophosphate. Of all the iodonium salts mentioned, compounds with other anions are, of course, also suitable; further sulphonium salts, obtainable, for example, under the trade names CYRACURE® UVI-6990, CYRACURE® UVI-6974 (Union Carbide), DEGACURE® KI 85 (Degussa), SP-55, SP-150, SP-170 (Asahi Denka), GE UVE 1014 (General Electric), SarCat® KI-85 (=triarylsulphonium hexafluorophosphate; Sartomer), SarCat® CD 1010 (=mixed triarylsulphonium hexafluoroantimonate; Sartomer); SarCat® CD 1011 (=mixed triarylsulphonium hexafluorophosphate; Sartomer); ferrocenium salts, e.g. ($\eta^6$-isopropylbenzene)($\eta^5$-cyclopentadienyl)-iron-II hexafluorophosphate, nitrobenzylsulphonates, alkyl- and aryl-N-sulphonyloxyimides and further known alkylsulphonic acid esters, haloalkylsulphonic acid esters, 1,2-disulphones, oxime sulphonates, benzoin tosylate, tolylsulphonyloxy-2-hydroxy-2-methyl-1-phenyl-1-propanone and further known betaketosulphones, beta-sulphonylsulphones, bis(alkylsulphonyl)diazomethane, bis(4-tert-butylphenyl-sulphonyl)-diazomethane, benzoyl-tosyl-diazomethane, iminosulphonates and imidosulphonates and trichloromethyl-s-triazines and other haloalkyl-group-containing compounds. Examples of further suitable additional photolatent acids (b1) include the examples of cationic photoinitiators and acid-formers as given in WO 04/074242, page 38, line 10 to page 41, line 14, as well as the compounds disclosed in the examples of WO 04/074242, the relevant disclosure of which is incorporated herein by reference.

Examples of free-radical photoinitiators as co-initiators are compounds as described above.

The compositions according to the invention may be used for a variety of purposes, for example as printing inks, such as screen-printing inks, flexo printing inks or offset printing inks, as clear lacquer, as coloured surface-coating compositions, as white surface-coating compositions, e.g. for wood or metal, as powder coating compositions, as paint, inter alia for paper, wood, metal or plastics, as daylight-curable paint for marking structures and roads, for photographic reproduction processes, for holographic recording materials, for image-recording processes or for the production of printing plates that are to be developed with organic solvents or using aqueous-alkaline media, in the production of masks for screen-printing, as dental filling compounds, as radiation-curable adhesives, as pressure-sensitive adhesives, as anti-adhesive coatings, as laminating resins, as photoresists, e.g. galvano-resists, etch resists or permanent resists, liquid films and dry films, as photostructurable dielectrics, and as solder masks for electronic circuits, as resists in the manufacture of colour filters for any type of screen or for producing structures in the manufacture of plasma displays and electroluminescent displays, in the manufacture of optical switches, optical gratings (interference gratings), in the coating or sealing of electronic components, e.g. as electroinsulating compounds, or as coatings for optical fibres, for coil coating, as indicator systems for UV radiation, X-rays and electron beams, and in the manufacture of three-dimensional articles, e.g. for stereolithography and for composites, e.g. for composites reinforced with glass or carbon or graphite fibres. The compositions are also suitable for the manufacture of optical lenses, e.g. contact lenses or Fresnel lenses, and also in the manufacture of medical apparatus, aids or implants.

The photocurable compositions according to the invention are suitable, for example, as coating materials for all kinds of substrates, for example wood, textiles, paper, ceramics, glass, marble, plastics, such as polyester, polyethylene terephthalate, polyolefins or cellulose acetate, especially in the form of films, and metals, such as Al, Cu, Ni, Fe, Zn, Mg or Co and GaAs, Si or $SiO_2$, to which a coating is to be applied or an image is to be applied by image-wise exposure, or to which a structured resist layer is to be applied.

The coating of the substrates can be effected by applying a liquid composition, a solution or suspension to the substrate. The choice of solvent in a solution and the concentration are governed chiefly by the nature of the composition and by the coating method. The solvent should be inert, that is to say it should not enter into any chemical reaction with the components and it should be capable of being removed again upon drying after the coating operation.

Examples of suitable solvents are ketones, ethers and esters, such as methyl ethyl ketone, isobutyl methyl ketone, cyclopentanone, cyclohexanone, 2-heptanone, methyl amyl ketone, N-methylpyrrolidone, gamma-butyrolactone, dioxane, tetrahydrofuran, 2-methoxyethanol, 2-ethoxyethanol, 1-methoxy-2-propanol, 1,2-dimethoxyethane, acetic acid ethyl ester, acetic acid n-butyl ester, propylene glycol monomethyl ether acetate, lactic acid ethyl ester, propylene carbonate and 3-ethoxy-propionic acid ethyl ester.

After coating of the substrates, the solvent is generally removed by drying.

The formulation is applied uniformly to a substrate by known coating methods, for example by spin-coating, immersion, knife coating, curtain pouring, brush application or spraying, especially by electrostatic spraying and reverse-roll coating, and by electrophoretic deposition. It is also possible to apply the photosensitive layer to a temporary flexible support and then coat the final substrate, e.g. a copper-laminated printed circuit board, by transferring the layer by lamination.

The amount applied (layer thickness) and the type of substrate (layer support) are dependent upon the desired field of use. The layer thickness range generally includes values from about 0.1 µm to more than 100 µm, preferably from 0.5 micrometre to 50 micrometres. In the manufacture of three-dimensional articles, e.g. by stereolithography, the dimensions of the articles that can be obtained are limited only by the size of the exposure apparatus.

The radiation-sensitive compositions according to the invention are used, for example, as negative resists that have very high photosensitivity and that can be developed in an aqueous-alkaline medium without swelling. They are suitable as photoresists for electronics, such as galvanoresists, etch resists, and in liquid and dry films, solder resists, as resists in the production of colour filters for any type of screen, or to form structures in the manufacture of plasma displays and electroluminescent displays, in the manufacture of printing plates, e.g. offset printing plates, in the manufacture of printing moulds for letterpress printing, flatbed printing, intaglio printing, flexo printing or screen-printing moulds, the production of relief copies, e.g. for the production of texts in braille, for the production of stamps, for use in the etching of mouldings or for use as a microresist in the manufacture of integrated switching circuits. The compositions can also be used as photostructurable dielectrics, for encapsulating materials or as an insulating coating in the manufacture of computer chips, printed circuits and other electrical or electronic components. The possible layer supports and processing conditions for the coated substrates vary accordingly.

The compounds according to the invention are also used in the manufacture of single- or multi-layer materials for image recording or image reproduction (copies, reprography), which may be monochromatic or polychromatic. Included therein are materials for holographic storage of information, e.g. for holographic images or 3-dimensional holographic data storage. Such materials can also be used in colour test systems. In that technology it is also possible to use formulations that comprise microcapsules and, to produce the image, a thermal step can be carried out after the exposure step. Such systems and technologies and their use are described, e.g., in U.S. Pat. No. 5,376,459.

For photographic recordings of information there are used, for example, films of polyester, cellulose acetate or plastics-coated papers; for offset printing moulds there is used specially treated aluminium; for the production of printed circuits there are used copper-coated laminates; and for the production of integrated switching circuits there are used silicon wafers. The layer thicknesses for photographic materials and offset printing moulds are generally from about 0.5 µm to 10 µm, and for printed circuits from 1.0 µm to about 100 µm.

The invention relates also to the use of compounds of formula I as radiation-sensitive acid donors in the manufacture of surface-coating compositions, printing inks, printing plates, dental compounds, stereolithography resins, adhesives, anti-adhesive coatings, colour filters, resist materials or image-recording materials.

The invention relates also to a coated substrate that is coated on at least one surface with a composition according to the invention, and to a method for the production of relief images, wherein a composition according to the invention is applied to a substrate and is then exposed image-wise.

The expression "image-wise exposure" includes irradiation through a mask that contains a predetermined pattern, for example a diapositive, a metal mask, a chrome mask on a trans-parent support, exposure by means of a laser beam that is moved, for example controlled by a computer, over the surface of the coated substrate and in that manner produces an image, and irradiation with computer-controlled electron beams (CTP). Images can also be produced by interference between two beams or images, for example for holographic uses. It is also possible to use liquid crystal masks that can be actuated pixel by pixel to produce digital images, as described, for example, by A. Bertsch, J. Y. Jezequel, J. C. Andre in Journal of Photochemistry and Photobiology A: Chemistry 1997, 107, pp. 275-281 and by K.-P. Nicolay in Offset Printing 1997, 6, pp. 34-37.

As already mentioned, the compounds of formula I can be used especially also as acid donors in photoresists. Resist systems can be obtained by image-wise exposure of formulations comprising compounds of formula I and a subsequent development step. The term "photoresist" is not limited to the chemically enhanced resists, but includes all resist materials in which reactions are initiated by the radiation-chemical production of acid and that, in a development step, result in a difference in solubility between exposed and non-exposed regions. For example, also included are resists that can be processed in an aqueous medium, as described, for example, in U.S. Pat. No. 5,998,092 and in SPIE, Vol. 3999, pp. 569-578 (2000) as well as resists based on a Pinacol rearrangement, as described, for example, in SPIE, Vol. 3999, pp. 62-73 (2000).

Accordingly, the invention relates also to a photoresist that comprises a compound of formula I as radiation-sensitive acid donor.

A chemically enhanced photoresist is to be understood as being a resist formulation in which the radiation-sensitive component provides a catalytic amount of acid, which in turn catalyses a chemical reaction of at least one acid-sensitive component of the resist. This results in a difference in the solubility of the irradiated and non-irradiated portions of the resist. As a result of the catalytic nature of that process, an acid molecule can initiate reactions at many sites because it diffuses through the reactive polymer matrix from one reaction site to the next, provided it is not captured or destroyed by secondary reactions. Even a low acid concentration is therefore sufficient to obtain large differences in solubility between irradiated and non-irradiated portions of the resist. It is therefore generally sufficient to add only a small amount of latent acid compound. It is necessary, however, for the latent acid donors to be chemically and thermally stable until they are being irradiated. It is also necessary for the latent catalysts to be readily soluble in the liquid resist formulation and in the solid resist film in order to avoid the formation of particles which would adversely affect the use of the resists in microelectronic processing processes.

It will be clear from the above remarks that chemical and thermal stability of the latent acid donor is essential for its use in chemically enhanced photoresists.

The difference in solubility between exposed and non-exposed areas in the resist, which results from the action of the acid-catalysed reaction, depends upon the other components in the resist. If the compositions according to the invention comprise components that increase the solubility of the composition in the developer after irradiation and optionally after thermal aftertreatment, then it is a positive photoresist.

The invention accordingly relates also to a positive photoresist.

If, however, the components of the composition lower the solubility in the developer after irradiation and optionally after thermal aftertreatment, then it is a negative photoresist.

The invention accordingly relates also to a negative photoresist.

An overview of chemically enhanced photoresists can be found, for example, in: H. Ito, IBM Journal of Research and Development, Vol. 41, No. 1/2, page 69 (1997); H. Ito, SPIE Vol. 3678, page 2 (1999); for negative resists in: J. M. Shaw et al. IBM Journal of Research and Development, Vol. 41, No. 1/2, page 81 (1997).

Suitable negative and positive, e.g. chemically amplified, resist formulations, in which the compounds of the formula I according to the present invention can be employed as photolatent acid donors are disclosed in WO 04/074242, page 19, last paragraph to page 38, line 7. Said disclosure is hereby incorporated by reference.

It is evident, that also additives (c), customary in resist formulations may be added to corresponding formulations comprising a compound of the formula I according to the present invention. Examples of such additives are used in photoresists in the customary amounts known to a person skilled in the art, and are for example, dyes, pigments, plasticizers, surfactants, flow improvers, wetting agents, adhesion promoters, thixotropic agents, colourants, fillers, solubility accelerators, spectral sensitizers, acid-amplifiers, photosensitizers and organic basic compounds. Further, solvents and surfactants may be added. A thorough disclosure is given in WO 04/074242, page 41, line 15 to page 45, line 4. Said disclosure is hereby incorporated by reference.

To prepare a photoresist, the compositions according to the present invention, suitably in a solvent, is applied to a substrate, the solvent is evaporated by heating and the coated substrate is exposed to electromagnetic radiation, e.g. a laser.

After exposure and, if necessary after the thermal treatment, the exposed sites of the composition (in the case of the positive resist) or the non-exposed sites of the composition (in the case of the negative resist) are removed using a developer in a manner generally known to a person skilled in the art. Optionally prior to the development step a further heating step is performed. A thorough disclosure is given in WO 04/074242, page 45, line 5 to page 47, line 8. Said disclosure is hereby incorporated by reference.

Thus, the invention relates also to a method of manufacturing a photoresist by
(1) applying a composition as described above to a substrate;
(2) heating the composition to a temperature of from 60° C. to 160° C.;
(3) carrying out image-wise exposure with light of a wavelength of from 150 nm to 1500 nm;
(4) optionally heating the composition to temperatures of from 60° C. to 160° C.; and
(5) subsequently developing with a solvent or an aqueous alkaline developer.

The invention relates also to the use of compounds of formula I as described above as photolatent acid donors in the polymerisation or crosslinking of cationically or acid-catalytically polymerisable or crosslinkable compounds or to increase the solubility of compounds that increase their solubility in a developer under the action of acid, and also to a method for the photopolymerisation or crosslinking of cationically or acid-catalytically polymerisable or crosslinkable compounds under the action of electromagnetic radiation, in which method a compound of formula I is used as photolatent acid donor.

A further subject of the invention is a method as described above in the manufacture of surface-coating compositions including scratch-resistant coatings, stain-resistant coatings, anti-fog coatings, stain resistant coatings, anticorrosion coatings, powder coating compositions, printing inks, non impact printing inks including ink jet printing inksprinting plates, dental compounds including composites, stereolithography resins, adhesives, anti-adhesive coatings (release coatings, especially silicon release coatings), conformal coatings, optical fiber coatings, colour filters, resist materials or image-recording materials including holography resins.

The composition according to the present invention, comprising a cationic photoinitiator of the formula I may also be employed in a vacuum deposition process as described in WO 02/064268. That is, the photoinitiators are suitable to be flash-evaporated vacuum-deposited. Accordingly, in a process for forming a solid poylmeric structure from flash-evaporated vacuum-deposited cationically curable monomeric material, comprising the steps (i) preparing a mixture of a cationically-curable monomer with a thermally stable, chemically inactive at room temperature, cationic photoinitiator;

(ii) flash-evaporating said mixture in a vacuum to produce a vapor;

(iii) condensing the vapor to produce a film; and (iv) exposing said film to a radiation source to produce a polymeric solid film, said photoinitiator is of the formula I as described above.

Suitable apparatus for said procedure, as wel as details concerning the monomers are described in WO 02/064268, the teachings of which are incorporated by reference.

The UV irradiation to release the acid is generally effected with light of a wavelength of from 157 to 600 nm. Suitable radiation is present, for example, in sunlight or light from artificial light sources. A large number of widely varying types of light source may be used. Point sources and also planiform radiators (lamp carpets) are suitable. Examples thereof include: carbon arc lamps, xenon arc lamps, medium-, high- and low-pressure mercury lamps, doped where appropriate with metal halides (metal halide lamps), microwave-excited metal vapour lamps, excimer lamps, superactinic fluorescent tubes, fluorescent lamps, argon incandescent lamps, flashlamps, photographic flood lights, light emitting diodes (LED), electron beams and X-rays. Further, exposure to a plasma or corona is suitable as radiation for activating the photoinitiator compounds according to the present invention. The distance between the lamp and the substrate to be exposed can vary according to the intended use and the type and strength of the lamp and may be, for example, from 0 cm to 150 cm, or from 0.5 cm to 150 cm, preferably from 2 cm to 150 cm. Laser light sources, for example excimer lasers, are also suitable. Lasers in the visible range can also be used.

The examples which follow illustrate the invention in more detail. Parts and percentages are, as in the remainder of the description and in the claims, by weight, unless stated otherwise. Where alkyl radicals having more than three carbon atoms are referred to without any mention of specific isomers, the n-isomers are meant in each case

EXAMPLE 1

Preparation of

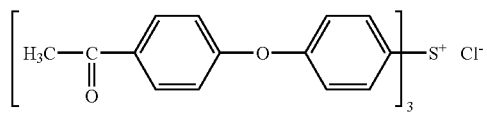

In a 200 ml reactor 1.54 g of thionyl chloride, 10.36 g of aluminium chloride and 9.62 g of 4-phenoxy-acetophenone [5031-78-7] are slowly added to 30 ml of o-dichlorobenzene at room temperature, and the reaction mixture is stirred for 3 hours at room temperature, and then for 3 hours at 50° C. The reaction mixture is poured on a water-ice mixture and well stirred. The product is extracted with dichloromethane and purified.

$^1$H-NMR data (δ ppm, DMSO-d$_6$): 8.05 6H d, 7.92 6H d, 7.43 6H d, 7.28 6H d, 2.59 9H s.

EXAMPLE 2

Preparation of

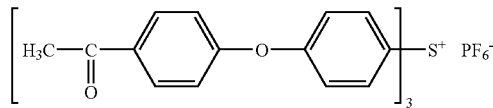

10.8 g of the compound of example 1 is dissolved in 30 ml of dichloromethane and 14.17 g of potassium hexafluorophosphate is dissolved in 150 ml of water. The two solutions are brought together and are stirred vigorously for 3 hours at room temperature. The phases are separated and the product is then isolated by evaporating the solvent. The product is purified by column chromatography.

$^1$H-NMR data (δ ppm, CDCl$_3$): 8.00 6H d, 7.70 6H d, 7.28 6H d, 7.13 6H d, 2.59 9H s.

EXAMPLE 3

Preparation of

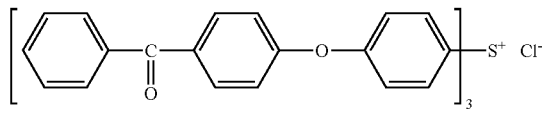

The compound is prepared according to the method as described in example 1, by employing 4-phenoxybenzophenone [6317-73-3] instead of 4-phenoxyacetophenone.

$^1$H-NMR data (δ ppm, CDCl$_3$): 8.02 6H d, 7.87 6H d, 7.79 6H d, 7.61 3H dxd, 7.50 6H dxd, 7.29 6H d, 7.17 6H d.

EXAMPLE 4

Preparation of

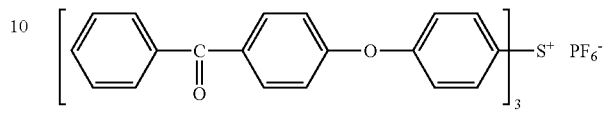

The compound is prepared from the compound of example 3 according to the method as described in example 2.

$^1$H-NMR data (δ ppm, CDCl$_3$): 7.88 6H d, 7.80 6H d, 7.71 6H d, 7.60 3H dxd, 7.51 6H dxd, 7.32 6H d, 7.18 6H d.

EXAMPLE 5

Preparation of

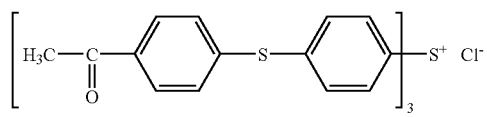

The compound is prepared according to the method as described in example 1, by employing 4-phenylthioacetophenone [10169-55-8] instead of 4-phenoxyacetophenone.

$^1$H-NMR data (δ ppm, CDCl$_3$): 7.98 6H d, 7.78 6H d, 7.57 6H d, 7.35 6H d, 2.63 9H s;

EXAMPLE 6

Preparation of

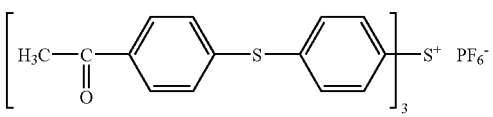

The compound is prepared from the compound of example 5 according to the method as described in example 2.

$^1$H-NMR data (δ ppm, CDCl$_3$): 8.00 6H d, 7.56 6H d, 7.52 6H d, 7.41 6H d, 2.63 9H s.

EXAMPLE 7

Preparation of

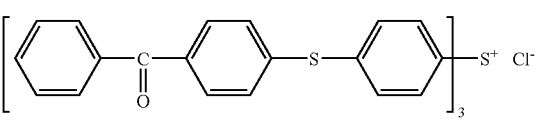

The compound is prepared according to the method as described in example 1, by employing 4-phenylthiobenzophenone [6317-78-8] instead of 4-phenoxyacetophenone.

$^1$H-NMR data (δ ppm, CDCl$_3$): 7.83-7.77 18H m, 7.64 3H dxd, 7.58 6H d, 7.52 6H dxd, 7.41 6H d.

EXAMPLE 8

Preparation of

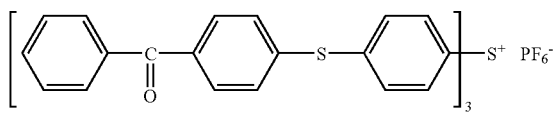

The compound is prepared from the compound of example 7 according to the method as described in example 2.

$^1$H-NMR data (δ ppm, CDCl$_3$): 7.86 6H d, 7.84 6H d, 7.65 3H dxd, 7.62 6H d, 7.54 6H d, 7.52 6H dxd, 7.45 6H d.

EXAMPLE 9

Preparation of

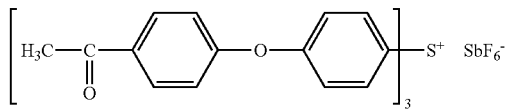

The compound is prepared from the compound of example 1 according to the method as described in example 2 with NaSbF$_6$ instead of KPF$_6$.

$^1$H-NMR data (δ ppm, CDCl$_3$): 8.03 6H d, 7.65 6H d, 7.31 6H d, 7.16 6H d, 2.62 9H s.

EXAMPLE 10

Preparation of

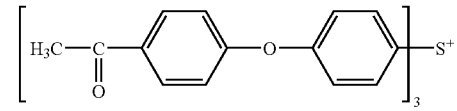

The compound is prepared from the compound of example 1 according to the method as described in example 2 with lithium[tris(trifluoromethylsulfonyl)methide] instead of KPF$_6$.

$^1$H-NMR data (δ ppm, CDCl$_3$): 8.03 6H d, 7.61 6H d, 7.28 6H d, 7.16 6H d, 2.61 9H s.

EXAMPLE 11

Preparation of

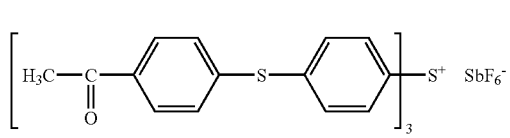

The compound is prepared from the compound of example 5 according to the method as described in example 2 with NaSbF$_6$ instead of KPF$_6$.

$^1$H-NMR data (δ ppm, CDCl$_3$): 7.98 6H d, 7.56 6H d, 7.52 6H d, 7.41 6H d, 2.61 9H s.

EXAMPLE 12

Preparation of

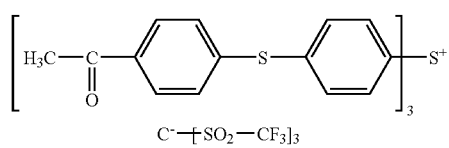

The compound is prepared from the compound of example 5 according to the method as described in example 2 with lithium[tris(trifluoromethylsulfonyl)methide] instead of KPF$_6$.

$^1$H-NMR data (δ ppm, CDCl$_3$): 8.01 6H d, 7.59 6H d, 7.45 6H d, 7.39 6H d, 2.63 9H s.

EXAMPLE 13

Preparation of

The compound is prepared according to the method as described in example 1, by employing 1-[4-(phenylthio)phenyl]-1-propanone [96187-78-9] instead of 4-phenoxyacetophenone.

¹H-NMR data (δ ppm, CDCl₃): 7.98 6H d, 7.78 6H d, 7.56 6H d, 7.36 6H d, 3.00 6H q, 1.24 9H t;

EXAMPLE 14

Preparation of

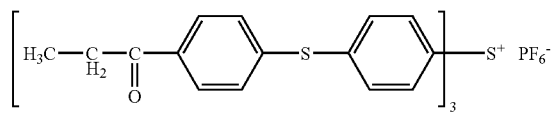

The compound is prepared from the compound of example 13 according to the method described in example 2.

¹H-NMR data (δ ppm, CDCl₃): 8.01 6H d, 7.58 6H d, 7.51 6H d, 7.41 6H d, 3.02 6H q, 1.24 9H t.

EXAMPLE 15

Preparation of

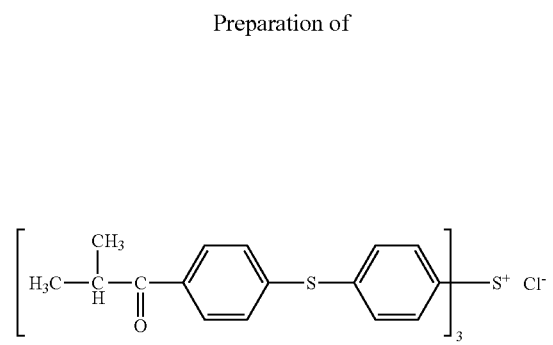

The compound is prepared according to the method as described in example 1, by employing 1-(4-phenylsulfanyl-phenyl)-propan-1-one [10130-82-2] instead of 4-phenoxyacetophenone.

¹H-NMR data (δ ppm, DMSO-d₆): 7.94 6H d, 7.84 6H d, 7.52 6H d, 7.37 6H d, 3.49 3H sept., 1.18 18H d.

EXAMPLE 16

Preparation of

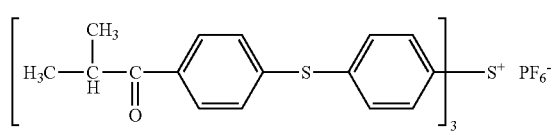

The compound is prepared from the compound of example 15 according to the method described in example 2.

¹H-NMR data (δ ppm, CDCl₃): 8.00 6H d, 7.58 6H d, 7.51 6H d, 7.41 6H d, 3.56 3H sept., 1.25 18H d;

EXAMPLE 17

Preparation of

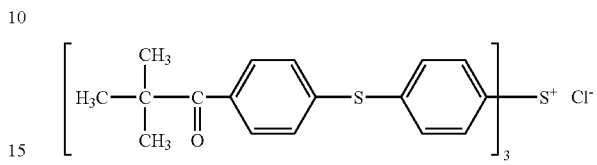

The compound is prepared according to the method as described in example 1, by employing 4-pivaloyl-diphenyl-sulfide (=the compound of example 21) instead of 4-phenoxyacetophenone.

¹H-NMR data (δ ppm, CDCl₃): 7.94 6H d, 7.84 6H d, 7.52 6H d, 7.37 6H d, 1.35 27H s.

EXAMPLE 18

Preparation of

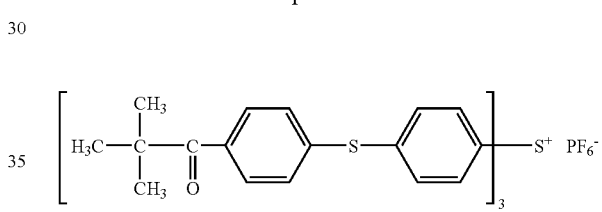

The compound is prepared from the compound of example 17 according to the method described in example 2.

¹H-NMR data (δ ppm, CDCl₃): 7.73 6H d, 7.52 6H d, 7.48 6H d, 7.37 6H d, 1.36 27H s.

EXAMPLE 19

Preparation of

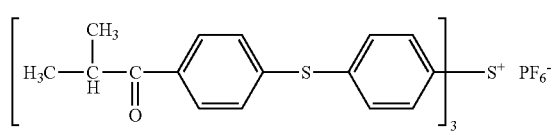

The compound is prepared according to the method as described in example 1, by employing 1-(4-phenylsulfanyl-phenyl)-octan-1-one [17792-67-5] instead of 4-phenoxyacetophenone.

$^1$H-NMR data (ppm, CDCl$_3$): 7.95 6H d, 7.76 6H d, 7.53 6H d, 7.34 6H d, 2.94 6H t, 1.76-1.69 6H m, 1.36-1.16 24H m, 0.87 9H t.

EXAMPLE 20

Preparation of

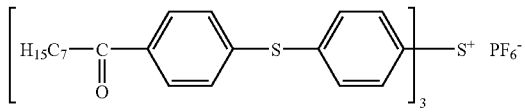

The compound is prepared from the compound of example 19 according to the method described in example 2.

$^1$H-NMR data (δ ppm, CDCl$_3$): 7.99 6H d, 7.57 6H d, 7.53 6H d, 7.40 6H d, 2.95 6H t, 1.78-1.69 6H m, 1.36-1.29 24H m, 0.89 9H t;

EXAMPLE 21

Preparation of

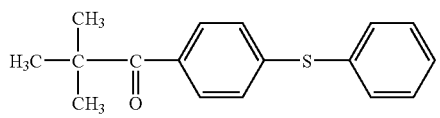

26.67 g of aluminum chloride are suspended in 100 ml dichloromethane, and 37.25 g of diphenylsulfide are added. Then 24.12 g of pivalic acid chloride are added slowly at 0° C., and the mixture is stirred for 1 hour at a temperature between 0° C. and 5° C. The mixture is poured on ice, the phases are separated and the organic phase is dried over MgSO$_4$. After evaporation of the solvent, the crude product is chromatographed over silica gel and the desired compound is obtained.

$^1$H-NMR data (δ ppm, CDCl$_3$): 7.69 2H d, 7.51-7.46 2H m, 7.42-7.36 3H m, 7.22 2H d, 1.36 9H s.

EXAMPLE 22

Preparation of

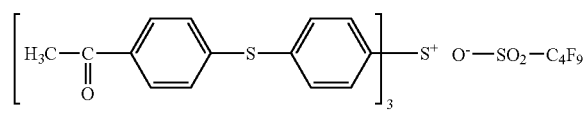

The compound is prepared from the compound of example 5 according to the method as described in example 2 with NaC$_4$F$_9$SO$_3$ (sodium nonaflate) instead of KPF$_6$.

$^1$H-NMR data (δ ppm, CDCl$_3$): 7.99 6H d, 7.61 6H d, 7.56 6H d, 7.40 6H d, 2.63 9H s.

EXAMPLE 23

Preparation of

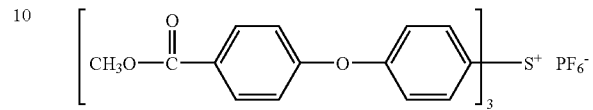

The compound is prepared according to the method as described in example 1, by employing 4-phenoxy-benzoicacidmethylester [21218-94-0] instead of 4-phenoxyacetophenone. The product then is directly transformed to the PF$_6$ salt according to the method as described in example 2.

$^1$H-NMR data (δ ppm, CDCl$_3$): 8.08 6H d, 7.70 6H d, 7.27 6H d, 7.12 6H d, 3.91 9H s.

EXAMPLE 24

Preparation of

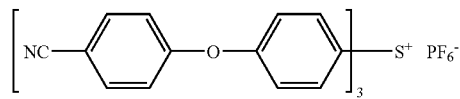

The compound is prepared according to the method as described in example 1, by employing 4-phenoxy-benzonitrile [3096-81-9] instead of 4-phenoxyacetophenone. The product then is directly transformed to the PF$_6$ salt according to the method as described in example 2.

$^1$H-NMR data (δ ppm, CDCl$_3$): 7.74 6H d, 7.60 6H d, 7.27 6H d, 7.12 6H d.

EXAMPLE 25

A composition is prepared by mixing the following components:
- 81.80 parts of 3,4-epoxycyclohexylmethyl carboxylate (CYRACURE® UVR 6105, provided by Dow Chemical)
- 11.73 parts of 3-ethyl-3-hydroxymethyl-oxetane (CYRACURE® UVR 6000, provided by Dow Chemical)
- 5.92 parts of ε-caprolactane triol (Tone Polyol 301, provided by Dow Chemical)
- 0.56 parts of a silicon surface additive (Byk 307, provided by BYK)
- 100.0 parts overprint varnish, felxo ink basic formulation The compound to be tested is stirred into said formulation, which then is applied with a 4 μm wire bar onto an aluminum film of 85 μm thickness.

Curing is effected by moving the sample on a conveyor belt under a 1×120 W/cm medium pressure mercury lamp (IST) fitted with an aluminum reflector.

The highest speed of the conveyor belt, which is used to cure the respective formulation is a measure for the reactivity of the tested photoinitiator compound. The results are collected in table 1.

TABLE 1

| Photoinitiator | concentration [%] | Cure speed [m/min] |
|---|---|---|
| of example 6 | 3 | 170 |
| of example 14 | 4 | 200 |
| of example 2 | 4 | 200 |

The invention claimed is:

1. A compound of the formula Ia $$\left[ L \underset{L_1}{\overset{L_2}{\bigotimes}} \underset{L_3}{\overset{L_4}{\bigotimes}} X \underset{L_5}{\overset{L_6}{\bigotimes}} \underset{L_7}{\overset{L_8}{\bigotimes}} \right]_3 S^+ \ Y^-, \text{ wherein}$$

(Ia)

$L$, $L_1$, $L_2$, $L_3$, $L_4$, $L_5$, $L_6$, $L_7$ and $L_8$ independently of one another are hydrogen, $R_1$, $OR_1$, $SR_1$, $NR_1R_2$, halogen, $NO_2$, $CN$, $NR_1COR_2$, $COOR_1$, $OCOR_1$, $CONR_1R_2$, $OCOOR_1$, $OCONR_1R_2$, $NR_1COOR_2$, $SO_3H$, $SO_3M$, $SOR_1$, $SO_2R_1$ or are COT; and/or the pairs $L_3$ and $L_5$ together are a single bond, $CR_aR_b$, CO, O, S, $NR_c$ or $NCOR_c$;

provided that $L_3$ and $L_5$ together are not a single bond, when X denotes a single bond; and/or the pairs $L_1$ and $L_3$, $L_1$ and $L$, $L_5$ and $L_7$ together are $C_1$-$C_3$alkylene, $CR_1$=$CR_2$-$CR_3$=$CR_4$, $CR_1$=$CR_2$—O, $CR_1$=$CR_2$—S, $CR_1$=$CR_2$—$NR_1$, CO—O—CO CONR$_1$CO, CO-(o-phenylene)-S, CO-(o-phenylene)-S substituted by one or more D, or are $C_1$-$C_3$alkylene interrupted by O, S, $NR_1$ or $NCOR_1$;

provided that at least one of L, $L_1$, $L_2$, $L_3$, $L_4$, $L_5$, $L_6$, $L_7$, $L_8$ is other than hydrogen;

$T_1$ and $T_2$ independently of one another are hydrogen, $C_1$-$C_{20}$alkyl, $C_5$-$C_{12}$cycloalkyl, $C_2$-$C_{20}$alkenyl, $C_5$-$C_{12}$cycloalkenyl, $C_6$-$C_{14}$aryl, $C_1$-$C_{20}$alkyl substituted by one or more D, $C_2$-$C_{20}$alkyl interrupted by one or more E, $C_2$-$C_{20}$alkyl substituted by one or more D and interrupted by one or more E, $C_5$-$C_{12}$cycloalkyl substituted by one or more D, $C_2$-$C_{12}$cycloalkyl interrupted by one or more E, $C_2$-$C_{12}$cycloalkyl substituted by one or more D and interrupted by one or more E, $C_2$-$C_{20}$alkenyl substituted by one or more D, $C_3$-$C_{20}$alkenyl interrupted by one or more E, $C_3$-$C_{20}$alkenyl substituted by one or more D and interrupted by one or more E, $C_5$-$C_{12}$cycloalkenyl substituted by one or more D, $C_3$-$C_{12}$cycloalkenyl interrupted by one or more E, $C_3$-$C_{12}$cycloalkenyl substituted by one or more D and interrupted by one or more E, or $C_6$-$C_{14}$aryl substituted by one or more D;

$R_1$, $R_2$, $R_3$, $R_4$, $R_a$, $R_b$ and $R_c$ independently of one another have the meaning of $T_1$;

T denotes $T_1$ or O-$T_2$;

X is a single bond, $CR_aR_b$, O, S, $NR_c$ or $NCOR_c$;

D is hydrogen, $R_5$, $OR_5$, $SR_5$, $NR_5R_6$, halogen, $NO_2$, CN, O-glycidyl, O-vinyl, O-allyl, $COR_5$, $NR_5COR_6$, $COOR_5$, $OCOR_5$, $CONR_5R_6$, $OCOOR_5$, $OCONR_5R_6$, $NR_5COOR_6$, $SO_3H$ or $SO_3M$;

E is O, S, COO, OCO, CO, $NR_5$, $NCOR_5$, $NR_5CO$, $CONR_5$, $OCOO$, $OCONR_5$, $NR_5COO$, $SO_2$, SO, $CR_5$=$CR_6$ or

<br>

$$\underset{R_5}{\overset{O}{\underset{|}{C}}} \underset{R_6}{\overset{}{\underset{|}{C}}} ;$$

$R_5$ and $R_6$ independently of one another are hydrogen, $C_1$-$C_{12}$alkyl or phenyl;

Y is an inorganic or organic anion; and

M is an inorganic or organic cation.

2. A compound of the formula Ia according to claim 1, wherein

L, $L_1$, $L_2$, $L_3$ and $L_4$ independently of one another are hydrogen, $R_1$, $OR_1$, halogen, $SO_3H$, $SO_3M$, $SOR_1$, $SO_2R_1$, CN, $NO_2$ or COT;

$L_5$, $L_6$, $L_7$ and $L_8$ independently of one another are hydrogen, $R_1$ or $OR_1$;

provided that at least one of L, $L_1$, $L_2$, $L_3$, $L_4$ is $SO_3H$, $SO_3M$, $SO_2R_1$, CN, $NO_2$ or COT;

$T_1$ and $T_2$ independently of one another are hydrogen, $C_1$-$C_{20}$alkyl, $C_5$-$C_{12}$cycloalkyl, $C_2$-$C_{20}$alkenyl, $C_6$-$C_{14}$aryl, $C_1$-$C_{20}$alkyl substituted by one or more D, $C_2$-$C_{20}$alkyl interrupted by one or more E, $C_2$-$C_{20}$alkyl substituted by one or more D and interrupted by one or more E, $C_5$-$C_{12}$cycloalkyl substituted by one or more D, $C_2$-$C_{12}$cycloalkyl interrupted by one or more E, $C_2$-$C_{12}$cycloalkyl substituted by one or more D and interrupted by one or more E, $C_2$-$C_{20}$alkenyl substituted by one or more D, $C_3$-$C_{20}$alkenyl interrupted by one or more E, $C_3$-$C_{20}$alkenyl substituted by one or more D and interrupted by one or more E, $C_6$-$C_{14}$aryl substituted by one or more D;

$R_1$, $R_a$, $R_b$ and $R_c$ independently of one another have the meaning of $T_1$;

T is $T_1$ or O—$T_2$;

X is a single bond, $CR_aR_b$, O, S, $NR_c$ or $NCOR_c$;

D is hydrogen, $R_5$, $OR_5$, $SR_5$, halogen, $NO_2$, CN, O-glycidyl, O-vinyl, O-allyl, $COR_5$, $COOR_5$ or $OCOR_5$;

E is O, S, COO, OCO, CO or $CR_5$=$CR_6$;

$R_5$ and $R_6$ independently of one another are hydrogen, $C_1$-$C_{12}$alkyl or phenyl;

Y is an inorganic or organic anion; and

M is an inorganic or organic cation.

3. A compound of the formula Ia according to claim 1, wherein $L_1$, $L_2$, $L_3$, $L_4$, $L_5$, $L_6$, $L_7$ and $L_8$ are hydrogen L is COT, $COOR_1$ or CN;

T is $T_1$;

$T_1$ is $C_1$-$C_{20}$alkyl or $C_6$-$C_{14}$aryl;

$R_1$ is $C_1$-$C_{20}$alkyl;

X is O or S;

Y is halogen or a non-nucleophilic anion, selected from the group $C_fF_{2f+1}SO_3^-$, $C_1$-$C_{20}$-perfluoroalkylsulphonyl-methide, $(BF_4)^-$, $(SbF_6)^-$, $(AsF_6)^-$, $(PF_6)^-$ and $(B(C_6F_5)_4)^-$; and f is an integer from 1 to 8.

4. Process for the preparation of a compound of the formula Ia, by reacting a compound of the formula II,

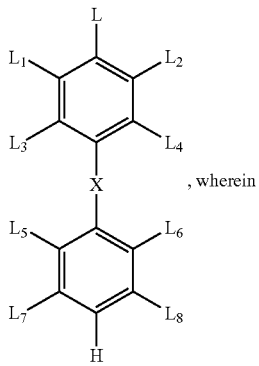

(II)

L, L₁, L₂, L₃, L₄, L₅, L₆, L₇, L₈ and X are as defined in claim 1;

with thionylchloride in the presence of a Friedel-Crafts catalyst, optionally followed by an exchange of the anion Y.

5. A radiation-sensitive composition comprising
(a1) a cationically or acid-catalytically polymerisable or crosslinkable compound or
(a2) a compound that increases its solubility in a developer under the action of acid; and
(b) at least one compound of the formula Ia according to claim 1.

6. A radiation-sensitive composition according to claim 5, additionally to components (a1) or (a2) and (b), comprising additional additives (c) and/or sensitiser compounds (d) and optionally further photoinitiators (e).

7. Surface-coating compositions, powder coating compositions, printing inks, printing plates, dental compounds, stereolithography resins, adhesives, anti-adhesive coatings, colour filters, resist materials or image-recording materials comprising at least one compound of the formula Ia according to claim 1.

8. A coated substrate that is coated on at least one surface with a composition according to claim 5.

9. A method for the photopolymerisation or crosslinking of cationically or acid-catalytically polymerisable or crosslinkable compounds under the action of electromagnetic radiation or an electron beam, in which method a compound of formula Ia according to claim 1 is used as photolatent acid donor.

10. Method according to claim 9 in the manufacture of surface-coating compositions, scratch-resistant coatings, stain-resistant coatings, antifog coatings, anticorrosion coatings, powder coating compositions, printing inks, non impact printing inks, ink jet printing inks, printing plates, dental compounds, composites for dental, composites, stereolithography resins, adhesives, anti-adhesive coatings, conformal coatings, optical fiber coatings, colour filters, resist materials or image-recording materials, holography resins.

* * * * *